(12) United States Patent
Karaborni et al.

(10) Patent No.: US 11,304,906 B2
(45) Date of Patent: Apr. 19, 2022

(54) CONTROLLED RELEASE GRANULATIONS OF WATER-SOLUBLE ACTIVE PHARMACEUTICAL INGREDIENTS

(71) Applicant: XWPHARMA LTD., Grand Cayman (KY)

(72) Inventors: Sami Karaborni, Cupertino, CA (US); Daniel M. Canafax, Half Moon Bay, CA (US); Jia-Ning Xiang, Fremont, CA (US); William W. Xiang, Fremont, CA (US); James Tien, Taoyuan (TW); Nicolas D. Kirkland, Norristown, PA (US)

(73) Assignee: XWPHARMA LTD., Grand Cayman (KY)

(*) Notice: Subject to any disclaimer, the term of this patent is extended or adjusted under 35 U.S.C. 154(b) by 0 days.

(21) Appl. No.: 17/350,939

(22) Filed: Jun. 17, 2021

(65) Prior Publication Data

US 2021/0393529 A1    Dec. 23, 2021

Related U.S. Application Data

(60) Provisional application No. 63/040,780, filed on Jun. 18, 2020, provisional application No. 63/059,514, filed on Jul. 31, 2020.

(51) Int. Cl.
*A61K 9/16*     (2006.01)
*A61K 31/225*   (2006.01)
*A61K 31/19*    (2006.01)

(52) U.S. Cl.
CPC .......... *A61K 9/1652* (2013.01); *A61K 9/1611* (2013.01); *A61K 9/1617* (2013.01); *A61K 31/19* (2013.01); *A61K 31/225* (2013.01)

(58) Field of Classification Search
None
See application file for complete search history.

(56) References Cited

U.S. PATENT DOCUMENTS

| | | | |
|---|---|---|---|
| 4,370,338 A | 1/1983 | Mizoule | |
| 5,110,797 A | 5/1992 | Ienaga et al. | |
| 6,489,350 B1 | 12/2002 | Benedyk et al. | |
| 7,482,429 B2 | 1/2009 | Albericio et al. | |
| 7,521,455 B2 | 4/2009 | Nagase et al. | |
| 7,960,561 B2 | 6/2011 | Sorensen et al. | |
| 8,529,954 B2 | 9/2013 | Lebon et al. | |
| 9,309,182 B2 | 4/2016 | Tung et al. | |
| 10,457,627 B2 * | 10/2019 | Xiang | A61P 25/16 |
| 10,501,401 B2 | 12/2019 | Xiang et al. | |
| 10,640,451 B2 | 5/2020 | Xiang et al. | |
| 10,774,031 B2 | 9/2020 | Xiang et al. | |
| 2004/0214755 A1 | 10/2004 | Albericio et al. | |
| 2005/0182045 A1 | 8/2005 | Nagase et al. | |
| 2006/0122383 A1 | 6/2006 | Zhou et al. | |
| 2006/0210630 A1 * | 9/2006 | Liang | A61K 9/5031 424/468 |
| 2008/0175873 A1 * | 7/2008 | Zhou | A61K 9/284 424/400 |
| 2010/0144869 A1 | 6/2010 | Nudelman et al. | |
| 2011/0111027 A1 | 5/2011 | Rourke et al. | |
| 2011/0178068 A1 | 7/2011 | Almarsson et al. | |
| 2011/0293729 A1 | 12/2011 | Lebon et al. | |
| 2012/0283300 A1 | 11/2012 | Kim et al. | |
| 2016/0052862 A1 | 2/2016 | Frost et al. | |
| 2019/0183806 A1 | 6/2019 | Guillard | |
| 2020/0009076 A1 * | 1/2020 | Patel | A61K 9/4816 |
| 2020/0276142 A1 * | 9/2020 | Grassot | A61P 43/00 |

FOREIGN PATENT DOCUMENTS

| | | |
|---|---|---|
| CN | 1422278 | 6/2003 |
| CN | 101511388 | 8/2009 |
| CN | 102076342 | 5/2011 |
| CN | 102834098 | 12/2012 |
| CN | 103370289 | 10/2013 |
| DE | 852392 | 10/1952 |
| EP | 0635265 | 1/1995 |
| EP | 2566462 | 3/2013 |
| FR | 2662695 | 12/1991 |
| JP | 62-270552 | 11/1987 |
| JP | 2002-503673 | 2/2002 |
| JP | 2003-522198 | 7/2003 |
| JP | 2004059452 | 2/2004 |
| JP | 2008-526713 | 7/2008 |
| JP | 2013-516465 | 5/2013 |
| RU | 2142800 | 12/1999 |
| WO | 1999/041275 | 8/1999 |
| WO | 1999/051613 | 10/1999 |
| WO | 2004/087169 | 10/2004 |

(Continued)

OTHER PUBLICATIONS

International Search Report and Written Opinion for International Application No. PCT/CN2016/099763, dated Jan. 3, 2017, 15 pages.
International Search Report and Written Opinion for International Application No. PCT/CN2017/078873, dated Jan. 9, 2018, 12 pages.
International Search Report and Written Opinion for International Application No. PCT/CN2018/090151, dated Feb. 20, 2019, 14 pages.
International Search Report and Written Opinion for International Application No. PCT/CN2018/097241, dated Apr. 28, 2019, 11 pages.
International Search Report and Written Opinion for International Application No. PCT/CN2018/109115, dated Jul. 8, 2019, 11 pages.
International Search Report and Written Opinion for International Application No. PCT/CN2018/118565, dated Jul. 8, 2019, Apr. 28, 2019, 13 pages.

(Continued)

*Primary Examiner* — Susan T Tran

(57) ABSTRACT

Pharmaceutical granulations having a functional coating surrounding a core containing a water-soluble active pharmaceutical ingredient are disclosed. The functional coating provides for immediate release or controlled release of the active pharmaceutical ingredient. The pharmaceutical granulations can be used in oral pharmaceutical compositions.

16 Claims, 23 Drawing Sheets

(56) References Cited

FOREIGN PATENT DOCUMENTS

| WO | 2005/123731 | | 12/2005 | |
|----|----|----|----|----|
| WO | 2006/038226 | | 4/2006 | |
| WO | 2009/040331 | | 4/2009 | |
| WO | 2009/102462 | | 8/2009 | |
| WO | 2009/137717 | | 11/2009 | |
| WO | 2010/124046 | | 10/2010 | |
| WO | 2011/119839 | | 9/2011 | |
| WO | WO-2011119839 | A1 * | 9/2011 | ............. A61P 25/20 |
| WO | 2013/019561 | | 2/2013 | |
| WO | 2013/163244 | | 10/2013 | |
| WO | 2014/031840 | | 2/2014 | |
| WO | 2014/078014 | | 5/2014 | |
| WO | 2014/152263 | | 9/2014 | |
| WO | 2014/205393 | | 12/2014 | |
| WO | 2015/057884 | | 4/2015 | |
| WO | 2015/083129 | | 6/2015 | |
| WO | 2017/049470 | | 3/2017 | |
| WO | 2017/050259 | | 3/2017 | |
| WO | 2018/098472 | | 5/2018 | |

OTHER PUBLICATIONS

International Search Report and Written Opinion for PCT Application No. PCT/US2020/066047, dated Mar. 23, 2021, 11 pages.

Non-Final Office Action for U.S. Appl. No. 16/831,086, dated Apr. 13, 2020, 8 pages.

Non-Final Office Action for U.S. Appl. No. 16/791,243, dated Apr. 8, 2020, 20 pages.

Ahn et al., "Hapten and Antibody Production for a Sensitive Immunoassay Determining a Human Urinary Metabolite of the Pyrethroid Insecticide Permethrin," Journal of Agricultural and Food Chemistry, Jun. 2004, vol. 52, No. 15, p. 4583-4594.

Search Report for Australia Application No. 2017406159, dated Feb. 28, 2020, 6 pages.

Search Report for Australia Application No. 2016328150, dated Mar. 27, 2020, 4 pages.

Search Report for Russia Application No. 2019134607, dated Feb. 11, 2020, 7 pages (translation).

Jiang, et al., Copper-Catalyzed Aerobic Oxidative Regioselective Thiocyanation of Aromatics and Heteroaromatics. J. Org. Chem. 2017, 82, 18, 9312-9320.

Jimonet et al., "Riluzole series. Synthesis and in vivo "antiglutamate" activity of 6-substituted-2-benzothiazolamines and 3-substituted-2-imino-benzothiazolines", Journal of Medical Chemistry, 1999, vol. 42, p. 2828-2843.

Jordan, et al., Efficient Conversion of Substituted Aryl Thioureas to 2-Aminobenzothiazoles Using Benzyltrimethylammonium Tribromide. J. Org. Chem. 2003, 68, 22, 8693-8696.

Kaname et al., "One-pot copper-catalyzed tandem addition-cyclization of 2-iodoanilines with isoselenocyanates for the practical preparation of 2-aminobenzoselenazoles," Tetrahedron Letters, Jan. 2011, vol. 52, Issue 4, p. 505-508.

Lee et al., "Development of an Immunoassay for the Residues of the Herbicide Bensulfuron-Methyl," Journal of Agricultural and Food Chemistry, Mar. 2002, vol. 50, No. 7, p. 1791-1803.

Luengo et al., "Synthesis and Structure-Activity Relationships of Macrocyclic FKBP Ligands", Bioorganic & Medicinal Chemistry Letters, 1994, vol. 4, No. 2, p. 321-324.

McGeer et al., "Pharmacologic Approaches to the Treatment of Amyotrophic Lateral Sclerosis", Drug Mechanisms and Targets, 2006, vol. 19, No. 1, p. 31-37.

RN 1243631-58-4, STN entry date Sep. 29, 2010.

STN Columbus, Registry Jul. 21, 1990, 128321-03-09, 81055-72-3.

STN Columbus, Registry Dec. 4, 2015, CAS No. 1822708-15-5.

RN 142229-71-8, STN entry date Jul. 3, 1992.

RN 1211588-05-4, STN REG, Mar. 19, 2010.

RN 1354448-66-0, STN REG, Jan. 25, 2012.

RN 1206250-52-3, STN REG, Feb. 12, 2010.

RN 1206250-51-2, STN REG, Feb. 12, 2010.

RN 1206250-54-5, STN REG, Feb. 12, 2010.

RN 1206248-58-9, STN REG, Feb. 12, 2010.

RN 1744-22-5, STN entry date Nov. 16, 1984.

RN 326-45-4, STN entry date Nov. 16, 1984.

RN 747353-64-6, STN REG, Sep. 17, 2004.

RN 60176-62-7, STN entry date Nov. 16, 1984.

RN 60176-63-8, STN REG, Nov. 16, 1984.

RN 60388-38-7, STN entry date Nov. 16, 1984.

CAS Registry No. 238401-16-6 entry date Sep. 10, 1999.

Rothweiler, et al., Probing the ATP-Binding Pocket of Protein Kinase DYRK1A with Benzothiazole Fragment Molecules. J. Med. Chem. 2016, 59, 21, 9814-9824.

Rynearson et al., "2-Aminobenzoxazole ligands of the hepatitis C virus internal ribosome entry site," Bioorganic & Medicinal Chemistry Letters, Aug. 2014, vol. 24, No. 15, p. 3521-3525.

Sankaranarayanan et al., "Naphtho[1,2-d]thiazol-2-ylamine (SKA-31), a new activator of KCa2 and KCa3.1 potassium channels, potentiates the endothelium-derived hyperpolarizing factor response and lowers blood pressure", Molecular Pharmacology, 2009, vol. 75, p. 281-295.

Staldweiser et al., "Combinatorial Solid-Phase Synthesis of Structurally Complex Thiazolylhydantoines," Angewandte Chemie Int. Ed., A Journal of the German Chemical Society, Jun. 1998, vol. 37, No. 10, p. 1402-1404.

Ward et al., "Discovery of an Orally Bioavailable Nki Receptor Antagonist, (2S, 3S)-(2-Methoxy-5-tetrazol-1-ylbenzyl)(2-phenylpiperidin-3-yl)amine (GR203040), with Potent Antiemetic Activity," Journal of Med. Chem., 1995, vol. 38, p. 4985-4992.

Partial International Search Report and Written Opinion for PCT Application No. PCT/US2021/037830, dated Oct. 6, 2021, 14 pages.

Partial International Search Report and Written Opinion for PCT Application No. PCT/US2021/037909, dated Oct. 4, 2021, 26 pages.

Cameo Chemicals, ethyl-3-hydroxybutyrate, retrieved from https://web.archive.org/web/20170209085248/ https://cameochemicals.noaa.gov/chemical/20385, 2017, 5 pages.

During et al., "Pharmaceutical Technology Report: Water-Soluble Cellulose Ethers as Release Modulators for Ethylcellulose Coatings on Multiparticulates", Annual Meeting of the American Association of Pharmaceutical Scientists, Nov. 2011, 9 pages.

International Search Report and Written Opinion for PCT Application No. PCT/US2021/037830, dated Dec. 7, 2021, 20 pages.

International Search Report and Written Opinion for PCT Application No. PCT/US2021/037909, dated Dec. 2, 2021, 27 pages.

International Search Report and Written Opinion for PCT Application No. PCT/US2021/042818, dated Nov. 12, 2021, 13 pages.

* cited by examiner

| Parameter | Example | | | | | | | | |
|---|---|---|---|---|---|---|---|---|---|
| | 2 | 3 | 4 | 5 | 6 | 7 | 8 | 9A | 9B |
| Spray Time (min) | 123 | 74 | 98 | 114 | 126 | 295 | 295 | 70 | 280 |
| Spray Rate (g/min) | 5-11 | 13-15 | 11-12 | 13-16 | 13.7-14.6 | 5.5-6.7 | 6.1-7.2 | 4.3-.9 | 5.0-5.7 |
| Exhaust Temp (°C) | 22-25 | 27-29 | 22-24 | 25-26 | 24-25 | 32-33 | 32-33 | 32-34 | 33-34 |
| Inlet Temp (°C) | 28-32 | 38-40 | 29-34 | 35-36 | 35-38 | 40-43 | 40-43 | 41-44 | 40-44 |
| Atomizing Air (psi) | 25 | 26 | 16-18 | 20-22 | 26 | 25 | 25 | 25 | 25 |
| Process Air (cfm) | 55-62 | 54-60 | 58-63 | 55-59 | 58-60 | 45-49 | 47-48 | 46-47 | 46-48 |
| Accelerator Air (psi) | 15 | 15 | 10 | 10-20 | 15-25 | 15 | 15 | 15 | 15 |
| Dew Point (°C) | 2.8-4.8 | 5.6-.3 | 3.5-5.0 | -0/2-0.1 | 5.5-7.0 | 9.4-13.0 | 12.4-15.0 | 8.5-9.7 | 10.6-13.3 |
| Weight Gain (%wg) | 10 | 10 | — | — | — | — | — | — | — |
| PAI, actual (wt%) | 85.2 | 87.8 | 16.9 | — | — | — | — | — | — |
| Weight Gain (%wg) | 20 | 20 | 20 | 20 | — | 20 | 20 | 20 | 20 |
| PAI, actual (wt%) | 73.9 | 78.8 | — | 79.9 | — | 79.4 | 81.8 | — | 80.7 |
| Weight Gain (%wg) | — | — | — | 30 | — | 30 | 30 | — | 30 |
| PAI, actual (wt%) | — | — | — | 74.5 | — | 75.2 | 75.3 | — | 76.0 |
| Weight Gain (%wg) | — | — | — | — | — | 35 | 35 | — | 35 |
| PAI, actual (wt%) | — | — | — | — | — | 71.9 | 72.4 | — | 72.9 |

FIG. 21

CONTROLLED RELEASE GRANULATIONS OF WATER-SOLUBLE ACTIVE PHARMACEUTICAL INGREDIENTS

This application claims the benefit under 35 U.S.C. § 119(e) of U.S. Provisional Application No. 63/059,514 filed on Jul. 31, 2020; and U.S. Provisional Application No. 63/040,780 filed on Jun. 18, 2020, each of which is incorporated by reference in its entirety.

FIELD

The disclosure relates to pharmaceutical granulations of water soluble active pharmaceutical ingredients having functional coating. The coated pharmaceutical granulations can be used in controlled release oral formulations.

BACKGROUND

In certain methods of treatment, it is necessary to administer a high dose of an active pharmaceutical ingredient. To minimize the amount of an oral pharmaceutical composition administered to a patient in such treatments, it is desirable that the pharmaceutical composition contains a high content of the active pharmaceutical ingredient and that the amount of pharmaceutical excipients be minimized.

Oral controlled-release dosage forms can contain granules coated with a functional coating that provides a desired release profile in the gastrointestinal tract.

Controlled release formulations containing pharmaceutical granulations having a high bulk density of an active pharmaceutical ingredient, suitable for dosing from once or two times a day are desired. To improve palatability, it is desirable that the pharmaceutical granulations have a low average particle size such as less than 500 μm.

SUMMARY

According to the present invention, pharmaceutical granulations comprise a plurality of coated granules, wherein, the coated granules comprise a core and a functional coating surrounding the core; the core comprises not less than 90 wt % of an active pharmaceutical ingredient, wherein, the active pharmaceutical ingredient has an aqueous solubility greater than 100 mg/mL; and wt % is based on the total weight of the core; and the functional coating comprises a plasticizer.

According to the present invention, pharmaceutical compositions comprise a pharmaceutical granulation according to the present invention.

According to the present invention, methods of providing a therapeutically effective amount of γ-hydroxybutyric acid in the systemic circulation of a patent for treating a disease comprise administering to a patient in need of such treatment a therapeutically effective amount of a pharmaceutical composition according to the present invention, for treating the disease.

According to the present invention, methods of treating a disease in a patient, wherein the disease is known to be treated by administering γ-hydroxybutyric acid, comprise administering to a patient in need of such treatment a therapeutically effective amount of a pharmaceutical composition according to the present invention, for treating the disease.

According to the present invention, methods of coating a pharmaceutical granulation comprise applying a coating composition to a pharmaceutical granulation comprising a plurality of granules, wherein the coating composition comprises: from 4 wt % to 12 wt % solids; greater than 10 wt % water; and from 75 wt % to 92 wt % ethanol; wherein wt % is based on the total weight of the coating composition; and the granules comprise: a core comprising no less than 90 wt % of an active pharmaceutical ingredient; and the active pharmaceutical ingredient has an aqueous solubility greater than 100 mg/mL, wherein wt % is based on the total weight of the core.

BRIEF DESCRIPTION OF THE DRAWINGS

Those skilled in the art will understand that the drawings described herein are for illustration purposes only. The drawings are not intended to limit the scope of the present disclosure.

FIG. 21 shows the process conditions used to apply the functional coatings described in Examples 2-9 to the uncoated pharmaceutical granulation described in Example 1.

DETAILED DESCRIPTION

Figure 1:
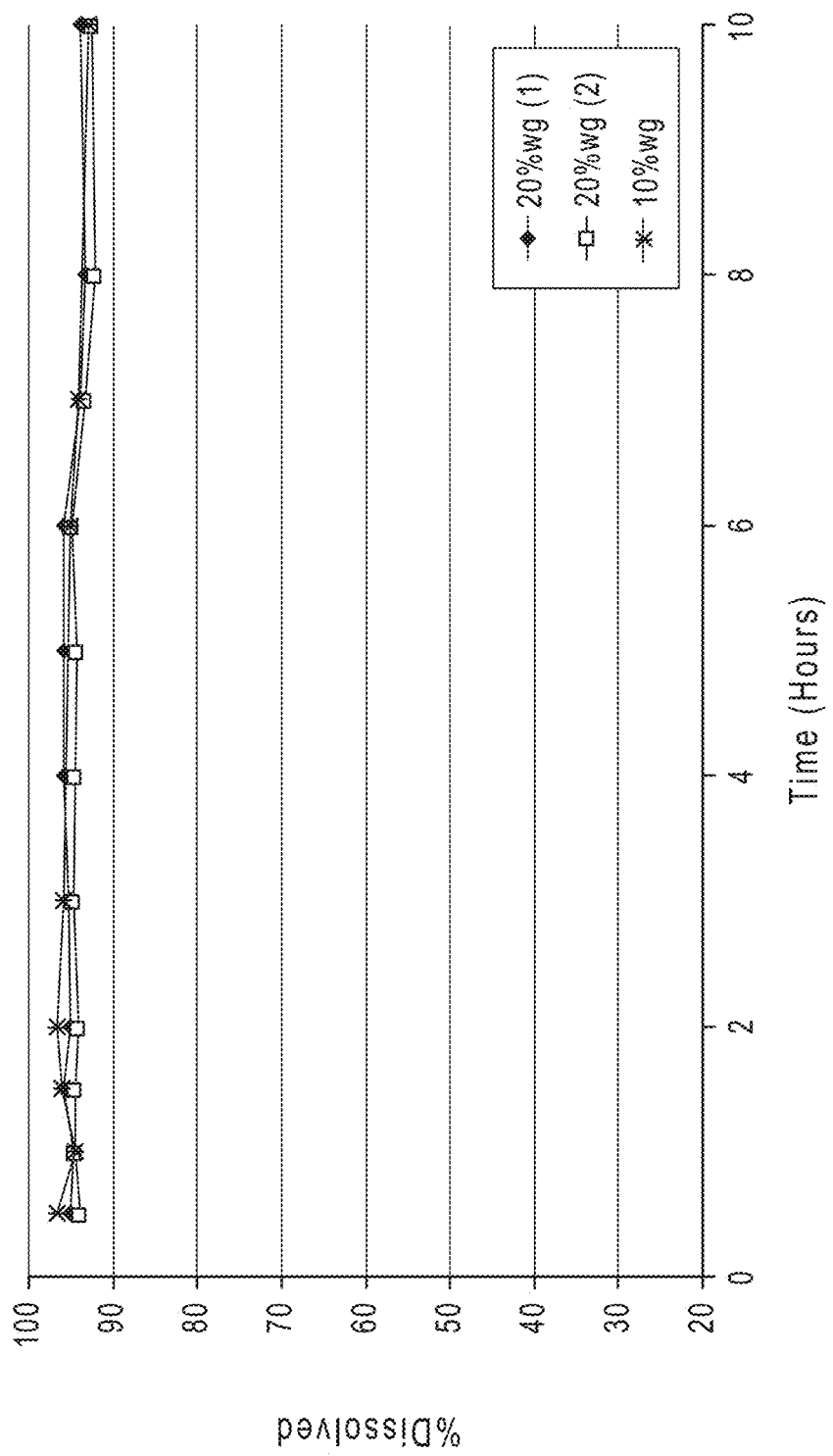
FIG. 1 shows dissolution profiles of an active pharmaceutical ingredient from granules having a coating of a methacrylic acid-methyl acrylate copolymer as described in Example 1.

For purposes of the following detailed description, it is to be understood that embodiments provided by the present disclosure may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about."

Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

"Immediate release" refers to a pharmaceutical composition that releases substantially all of an active pharmaceutical ingredient into the gastrointestinal tract of a patient within less than 1 hour following oral administration, such as within less than 50 minutes, within less than 40 minutes, within less than 30 minutes, within less than 20 minutes, or within less than 10 minutes following oral administration. For example, an immediate release dosage form can release greater than 90%, greater than 95%, or greater than 98% of the active pharmaceutical ingredient in the pharmaceutical composition into the gastrointestinal tract within less than 1 hour such as within less than 50 minutes, less than 40 minutes, less than 30 minutes, less than 20 minutes, or less than 10 minutes, following oral administration. Immediate release pharmaceutical compositions can be appropriate to administer active pharmaceutical ingredients that are absorbed into the systemic circulation from the upper portion of the gastrointestinal tract.

"Controlled release" pharmaceutical compositions include modified release formulations, delayed release formulations, extended release formulations, sustained release formulations, timed release formulations, pulsatile release formulations, and pH-dependent release formulations. These formulations are intended to release an active pharmaceutical ingredient from the pharmaceutical composition at a desired rate and/or at a desired time following oral administration by a patient and/or at a certain location or locations within the gastrointestinal tract and/or at a certain pH within the gastrointestinal tract. The United States Pharmacopeia defines a modified release system as one in which the time course or location of drug release or both, are chosen to accomplish objectives of therapeutic effectiveness or convenience not fulfilled by immediate release dosage forms. A controlled release pharmaceutical composition can include extended release and delayed-release components. A delayed release pharmaceutical composition is one that releases a drug all at once at a time other than immediately after oral administration. A modified release formulation can include delayed-release using enteric coatings, site-specific or timed release such as for colonic delivery, extended-release including, for example, formulations capable of providing zero-order, first-order, or biphasic release profiles, and programmed release such as pulsatile and delayed extended release.

"Alkoxy" refers to a radical —OR where R is alkyl. Examples of alkoxy groups include methoxy, ethoxy, propoxy, and butoxy. An alkoxy group can be, for example, $C_{1-6}$ alkoxy, $C_{1-5}$ alkoxy, $C_{1-4}$ alkoxy, $C_{1-3}$ alkoxy, ethoxy or methoxy.

"Alkyl" refers to a saturated, branched or straight-chain, monovalent hydrocarbon radical derived by the removal of one hydrogen atom from a single carbon atom of a parent alkane. An alkyl group can be, for example, $C_{1-6}$ alkyl, $C_{1-5}$ alkyl, $C_{1-4}$ alkyl, or $C_{1-3}$ alkyl. An alkyl group can be methyl, ethyl, n-propyl, iso-propyl, or tert-butyl.

"Cycloalkyl" refers to a saturated cyclic alkyl radical. A cycloalkyl group can be, for example, $C_{3-6}$ cycloalkyl, $C_{3-5}$ cycloalkyl, $C_{5-6}$ cycloalkyl, cyclopropyl, cyclopentyl, or cyclohexyl. A cycloalkyl can be selected from cyclopropyl, cyclobutyl, cyclopentyl, and cyclohexyl.

"Alkoxycarbonyl" refers to a radical —C(=O)—O—R where R can be $C_{1-6}$ alkyl such as $C_{1-4}$ alkyl, or $C_{1-3}$ alkyl. For example, R can be selected from methyl, ethyl, n-propyl, iso-propyl, and tert-butyl.

"Cycloalkoxycarbonyl" refers to a radical —C(=O)—O—R where R can be $C_{3-8}$ cycloalkyl, such as $C_{4-7}$ cycloalkyl or $C_{4-6}$ cycloalkyl. R can be selected, for example, from cyclopropyl, cyclobutyl, cyclopentyl, and cyclohexyl.

"Coating" refers to the dried layer applied to granule. A "coating composition" refers to the material applied to a granulation to provide a coating. A coating composition comprises solids and solvents including water. After applying a coating composition to a granulation and drying the coated granulation, the coating comprises the solids content of the coating composition.

The terms "granulation" and "granule" are used interchangeably. A granulation comprises a plurality of granules. However, for purposes of clarity when expressions such as "a coated granule" also refers to "a coated granulation" and "a coated granulation" refers to "a costed granule."

The particle size distribution parameter D90 refers to the point in the size distribution of a sample, up to and including which, 90% of the total volume of material in the sample is contained. For example, for a D90 of 400 μm, 90% of the sample volume has a size of 400 μm or less D50 is the size below which 50% of the total volume of material in the sample, is contained. Similarly, D10 refers to the size below which 10% of the total volume of material in the sample is contained. The volume distribution of the sample can be determined by laser diffraction or by sieve analysis.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids and one or more protonable functional groups such as primary, secondary, or tertiary amines within the parent compound. Examples of suitable inorganic acids include hydrochloric acid, hydrobromic acid, sulfuric acid, nitric acid, phosphoric acid, and the like. A salt can be formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid. A salt can be formed when one or more acidic protons present in the parent compound are replaced by a metal ion, e.g., an alkali metal ion, an alkaline earth ion, or an aluminum ion, or combinations thereof; or coordinates with an organic base such as ethanolamine, diethanolamine, triethanolamine, and N-methylglucamine. A pharmaceutically acceptable salt can be the hydrochloride salt. A pharmaceutically acceptable salt can be the sodium salt. In compounds having two or more ionizable groups, a pharmaceutically acceptable salt can comprise one or more counterions, such as a bi-salt, for example, a dihydrochloride salt.

The term "pharmaceutically acceptable salt" includes hydrates and other solvates, as well as salts in crystalline or non-crystalline form. Where a particular pharmaceutically acceptable salt is disclosed, it is understood that the particular salt (e.g., a hydrochloride salt) is an example of a salt, and that other salts may be formed using techniques known to one of skill in the art. Additionally, one of skill in the art would be able to convert the pharmaceutically acceptable salt to the corresponding compound, free base and/or free acid, using techniques generally known in the art.

"Percent weight gain" or "% wg" such as in the expression "a "35% wg" refers to the increased weight of a granule or granulation following application of a coating. For example, a 35% wg refers to a coated granule or coated granulation in which the weight of the coated granule or coated granulation is 35% greater than the weight of the uncoated granule or uncoated granulation.

Dissolution profiles were measured using a USP Type 2 dissolution apparatus and a sodium acetate buffered solution at pH 4.5 at a temperature of 37° C. and a paddle speed of 75 rpm.

"Active pharmaceutical ingredient" refers to an active drug substance or a compound that is converted following administration into an active drug substance such as a prodrug.

"Prodrug" refers to a derivative of a parent drug molecule that requires a transformation within the body to provide the active drug. Prodrugs are frequently, although not necessarily, pharmacologically inactive until converted to the parent drug. Prodrugs may be obtained by bonding a promoiety typically via a functional group, to a parent drug.

"Curing" a disease refers to eliminating a disease or disorder or eliminating a symptom of a disease or disorder.

"Treating" or "treatment" of a disease or disorder refers to inhibiting the disease or disorder or one or more clinical symptoms of the disease or disorder, arresting the development of the disease or disorder or one or more clinical symptoms of the disease or disorder, relieving the disease or disorder or one or more clinical symptoms of the disease or disorder, causing the regression of the disease or disorder or one or more clinical symptoms of the disease or disorder, reducing the severity of one or more clinical symptom of the disease or disorder, delaying the onset of one or more clinical symptoms of the disease or disorder, and/or mitigating one or more clinical symptoms of the disease or disorder, and/or stabilization of the disease or disorder or one or more clinical symptoms of the disease or disorder. "Treating" or "treatment" of a disease or disorder refers to producing a clinically beneficial effect without curing the underlying disease or disorder.

"Therapeutically effective amount" refers to the amount of a compound such as active pharmaceutical ingredient that, when administered to a patient for treating a disease, or at least one of the clinical symptoms of a disease, is sufficient to affect such treatment of the disease or symptom thereof. A "therapeutically effective amount" may vary depending, for example, on the compound, the disease and/or symptoms of the disease, the severity of the disease and/or symptoms of the disease or disorder, the age, weight, and/or health of the patient to be treated, and the judgment of the prescribing physician. A therapeutically effective amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Vehicle" refers to a diluent, excipient or carrier with which a compound is administered to a patient. A vehicle can be a pharmaceutically acceptable vehicle. Pharmaceutically acceptable vehicles are known in the art.

Reference is now made to pharmaceutical granulations having a functional coating, methods of making coated pharmaceutical granulations, and pharmaceutical compositions comprising coated pharmaceutical granulations. The disclosed coated pharmaceutical granulations, compositions comprising the coated pharmaceutical granulations, and methods of making the coated pharmaceutical granulations are not intended to be limiting of the claims. To the contrary, the claims are intended to cover all alternatives, modifications, and equivalents.

Coated pharmaceutical granulations provided by the present disclosure can be used to provide controlled release of an active pharmaceutical ingredient following oral administration to a patient. The coated pharmaceutical granulations contain a hygroscopic, highly water-soluble active pharmaceutical ingredient. The water-soluble active pharmaceutical ingredient can be prone to hydrolysis. The coated pharmaceutical granulations can be used in oral pharmaceutical compositions. The coated pharmaceutical granulations can be used to orally administer high doses of an active pharmaceutical ingredient.

A coated pharmaceutical granulation or coated granule comprises a coating surrounding a core.

Uncoated pharmaceutical granulations are disclosed in U.S. application Ser. No. 17/350,478 filed on Jun. 17, 2021, which is incorporated by reference in its entirety.

An uncoated pharmaceutical granulation provided by the present disclosure can comprise a plurality of granules, wherein the granules comprise, for example, not less than 90 wt % of an active pharmaceutical ingredient, such as greater than 90 wt % of an active pharmaceutical ingredient, wherein the pharmaceutical granulation can be characterized by a particle size distribution (PSD) (D50) from, from 150 µm to 500 µm, 150 µm to 450 µm, 150 µm to 400 µm, from 150 µm to 350 µm, from 150 µm to 300 µm, from 200 µm to 300 µm, or from 150 µm to 250 µm, where the particle size distribution is determined by sieve analysis; and wt % is based on the total weight of the pharmaceutical granulation. An uncoated granulation can have a particle size distribution D50 less than 400 µm, less than 350 µm, less than 300 µm, less than 250 µm, or less than 200 µm, where PSD is determined by sieve analysis.

An uncoated granule can comprise, for example, from 90 wt % to 99.5 wt % of an active pharmaceutical ingredient, from 90 wt % to 99 wt %, from 92 wt % to 99 wt %, from 95 wt % to 99 wt %, or from 98 wt % to 99 wt % of the active pharmaceutical ingredient, where wt % is based on the total weight of the uncoated granule. An uncoated granule can comprise, for example, greater than 90 wt % of an active pharmaceutical ingredient, greater than 92 wt %, greater than 94 wt %, greater than 96 wt %, greater than 98 wt %, or greater than 99 wt % of an active pharmaceutical ingredient, wherein wt % is based on the total weight of the uncoated granule.

An uncoated granule can be characterized by a particle size distribution (D50), for example, from 225 µm to 275 µm, wherein the particle size distribution is determined by sieve analysis.

An uncoated granule can be characterized by a particle size distribution (D10), for example, from 50 µm to 150 µm; and a particle size distribution (D90) from 450 µm to 750 µm, where the particle size distribution is determined by sieve analysis.

An uncoated granule can be characterized by a particle size distribution (D10), for example, from 80 µm to 120 µm; and a particle size distribution (D90) from 510 µm to 650 µm, where the particle size distribution is determined by sieve analysis.

An uncoated granule can be characterized by a particle size distribution (D10) of 106 µm; a particle size distribution (D50) of 267 µm; and a particle size distribution (D90) of 533 µm, where the particle size distribution is determined by sieve analysis.

An uncoated granule can be characterized by a particle size distribution (D50), for example, less than 500 µm, less than 450 µm, less than 400 µm, less than 350 µm, less than 300 µm, less than 250 µm, or less than 200 µm, wherein the particle size distribution is determined by sieve analysis.

In addition to an active pharmaceutical ingredient, an uncoated granule can further comprise a binder and an antistatic agent.

An uncoated granule can comprise, for example, not less than 90 wt % of a pharmaceutically active ingredient, such as greater than 90 wt % of a pharmaceutically active ingredient, from 0.1 wt % to 5 wt % of a binder, and from 0.1 wt % to 5 wt % of an antistatic agent, where wt % is based on the total weight of the pharmaceutical granulation.

An uncoated granule can comprise, for example, from 98 wt % to 99 wt % of an active pharmaceutical ingredient; from 0.25 wt % to 0.75 wt % of a binder; and from 0.5 wt % to 1.5 wt % of an antistatic agent, where wt % is based on the total weight of the uncoated granule.

An uncoated granule can comprise, for example, 98.5 wt % of the active pharmaceutical ingredient; 0.5 wt % of a binder; and 1.0 wt % of an antistatic agent, where wt % is based on the total weight of the uncoated granule.

An uncoated granule can comprise a binder or combination of binders.

An uncoated granule can comprise, for example, less than 6 wt % of a binder, less than 5 wt %, less than 4 wt %, less than 3 wt % less than 2 wt %, less than 1 wt %, less than 0.8 wt %, less than 0.6 wt %, less than 0.4 wt %, or less than 0.2 wt % of a binder, where wt % is based on the total weight of the uncoated granule. An uncoated granule can comprise, for example, from 0.1 wt % to 6.0 wt %, from 0.1 wt % to 5.0 wt %, from 0.1 wt % to 4.0 wt %, from 0.1 wt % to 3.0 wt %, from 0.1 wt % to 2.0 wt %, from 0.1 wt % to 1.0 wt %, from 0.2 wt % to 0.9 wt %, from 0.2 wt % to 0.8 wt %, from 0.25 wt % to 0.75 wt %, or from 0.3 wt % to 0.7 wt % of a binder, where wt % is based on the total weight of the uncoated granule.

An uncoated granule can comprise, for example, less than 1.5 wt % of a binder, less than 1.2 wt %, less than 1.0 wt %, less than 0.8 wt %, or less than 0.6 wt % of a binder, where wt % is based on the total weight of the uncoated granule.

A binder can comprise a water-soluble polymer.

Examples of suitable binders include natural binders such as starch, pregelatinized starch, sodium alginate, and gelatin; synthetic binders such as polyvinyl pyrrolidone, methylcellulose, hydroxypropylmethyl cellulose, polymethacrylates, sodium carboxy methyl cellulose, and polyethylene glycol; and saccharides such as modified cellulose, hydroxypropyl cellulose, sorbitol, xylitol, and mannitol.

Examples of other suitable binders include, acacia, copovidone, carbomer, corn starch, pregelatinized starch, calcium carboxymethyl cellulose, calcium cellulose glycolate, carmellosum calcium, carboxymethyl cellulose sodium, carmellose sodium, ceratonia, chitosan hydrochloride, dextrates, dextrin, ethyl cellulose, liquid glucose, guar galatomannan, guar gum, hydroxyethyl cellulose, microcrystalline cellulose, hydroxyethylmethyl cellulose, hydroxypropyl cellulose, low-substituted hydroxypropyl cellulose, hydroxypropyl starch, hypromellose/hydroxypropyl methyl cellulose, Methocel®, inulin, magnesium aluminum silicate, maltodextrin, methylcellulose, polyethylene glycol, polyethylene oxide, povidone, sodium alginate, starch, pregelatinized starch, sucrose, compressible sugar, zein, gelatin, polymethacrylates, sorbitol, glucose, and sodium alginate.

A binder can comprise hydroxypropyl cellulose, hydroxypropylmethyl cellulose or a combination thereof.

In an uncoated pharmaceutical granulation, the binder can comprise hydroxypropylmethyl cellulose. In certain uncoated pharmaceutical granulations, the binder does not comprise hydroxypropylmethyl cellulose.

In an uncoated pharmaceutical granulation, the binder can comprise hydroxypropyl cellulose.

An uncoated granule can comprise an antistatic agent or a combination of antistatic agents.

An uncoated granule can comprise, for example, less than 6 wt % of an antistatic agent, less than 5 wt %, less than 4 wt %, less than 3 wt %, less than 2.5 wt %, less than 2.0 wt %, less than 1.25 wt %, less than 1 wt %, less than 0.75 wt %, less than 0.5 wt %, or less than 0.25 wt % of an antistatic agent, where wt % is based on the total weight of the uncoated granule. An uncoated granule can comprise, for example, from 0.1 wt % to 2.0 wt % of an antistatic agent, from 0.2 wt % to 1.8 wt %, from 0.5 wt % to 1.50 wt %, or from 0.75 wt % to 1.25 wt % of an antistatic agent, where wt % is based on the total weight of the uncoated granule.

An uncoated granule can comprise a suitable antistatic agent.

Examples of suitable antistatic agents include silica, talc, magnesium stearate, sodium stearyl fumarate, and combinations of any of the foregoing.

An antistatic agent can comprise silica such as hydrophilic silica, such as hydrophilic fumed silica.

In an uncoated pharmaceutical granulation, the antistatic agent can comprise hydrophilic fumed silica.

An antistatic agent can comprise, for example, hydrophilic fumed silica such as Aerosil® fumed silica from Evonik Industries, Cab-o-sil® fumed silica from Cabot Corporation, or HDK® fumed silica from Brenntag Solutions Group.

An antistatic agent can comprise Aerosil® 200 available from Evonik Industries.

A hydrophilic fumed silica can have a specific surface area (BET from 100 $m^2$/g to 300 $m^2$/g such as from 175 $m^2$/g to 225 $m^2$/g, a pH value from 3.7 to 4.5 in a 4% aqueous dispersion, a loss on drying in 2 hours at 105° C. of less than or equal to 1.5%, a tamped density from about 40 g/L to 60 g/L, and an $SiO_2$ content greater than 99.8% based on ignited material.

In certain granulations, the antistatic agent comprises talc. Pharmaceutical grade talc is available, for example, from Imerys Talc and Elementis PLC.

In certain uncoated granulations, the antistatic agent does not comprise talc. In certain uncoated granulations, the binder does not comprise hydroxypropylmethyl cellulose and the antistatic agent does not comprise talc.

In addition to an active pharmaceutical ingredient, a binder, and an antistatic agent a granule can comprise one or more excipients such as, for example, flow control agents, lubricants, disintegrants, fillers, compression aids, surfactants, diluents, colorants, buffering agents, glidants, and combinations of any of the foregoing.

An uncoated granule can comprise, for example, less than 3 wt % of the one or more excipients, less than 2 wt %, less than 1 wt %, or less than 0.5 wt % of the one or more excipients, where wt % is based on the total weight of the granule. A granule can comprise, for example, from 0 wt % to 3% of one or more excipients, from 0.1 wt % to 3 wt %, from 0.5 wt % to 2 wt % or from 1 wt % to 2 wt % of one or more excipients, where wt % is based on the total weight of the granule.

Examples of suitable flow control agents or glidants include magnesium stearate, fumed silica (colloidal silicon dioxide), starch, talc, and combinations of any of the foregoing.

Examples of suitable lubricants include magnesium stearate, stearic acid, calcium stearate, hydrogenated castor oil, hydrogenated vegetable oil, light mineral oil, magnesium stearate, mineral oil, polyethylene glycol, sodium benzoate, sodium stearyl fumarate, zinc stearate, and combinations of any of the foregoing.

Examples of suitable disintegrants include citric acid croscarmellose sodium, colloidal silicone dioxide, crospovidone, sodium starch glycolate, microcrystalline cellulose, pregelatinized starch, and combinations of any of the foregoing.

A surfactant can comprise an ionic surfactant or a non-ionic surfactant. Examples of suitable ionic surfactants include docusate sodium (dioctyl sulfosuccinate sodium salt), sodium lauryl sulfate, and combinations of any of the foregoing. Examples of suitable non-ionic surfactants include polyoxyethylene alkyl ethers, polyoxyethylene stearates, poloxamers, polysorbate, sorbitan esters, glyceryl monooleate, and combinations of any of the foregoing.

Examples of suitable fillers and compression aids include lactose, calcium carbonate, calcium sulfate, compressible sugars, dextrates, dextrin, dextrose, kaolin, magnesium carbonate, magnesium oxide, maltodextrin, mannitol, microcrystalline cellulose, powdered cellulose, sucrose, and combinations of any of the foregoing.

An uncoated pharmaceutical granulation comprises a plurality of uncoated granules. To form a coated pharmaceutical granulation, a functional coating and optional seal coat can be applied to the uncoated pharmaceutical granulation. The coated granulation comprises a plurality of coated granules. The coated granules comprise a functional coating surrounding the uncoated granule, and which can be referred to as the core of the coated granule.

An uncoated pharmaceutical granulation provided by the present disclosure comprises a plurality of granules, where the granules can comprise, for example, greater than 85 wt % of an active pharmaceutical ingredient, greater than 90 wt %, or greater than 95 wt % of an active pharmaceutical ingredient, where wt % is based on the total weight of the uncoated granules; and the uncoated pharmaceutical granulation is characterized by a particle size distribution (D50), the median diameter), for example, from 150 μm to 450 μm.

An uncoated granule can comprise a high loading of an active pharmaceutical ingredients or a high loading of a combination of active pharmaceutical ingredients. For example, an uncoated granule can comprise greater than 85 wt %, greater than 90 wt %, greater than 95 wt %, greater than 96 wt %, greater than 97 wt %, greater than 98 wt % or greater than 99 wt % of an active pharmaceutical ingredient, where wt % is based on the total weight of the uncoated granule. An uncoated granule can comprise, for example, from 85 wt % to 99.5 wt % of an active pharmaceutical ingredient, from 90 wt % to 99.5 wt %, from 95 wt % to 99.5 wt %, from 96 wt % to 99 wt %, from 97 wt % to 99 wt %, or from 98 wt % to 99 wt % of an active pharmaceutical ingredient, where wt % is based on the total weight of the uncoated granule.

An uncoated granule can comprise an active pharmaceutical ingredient having a high aqueous solubility.

For example, an active pharmaceutical ingredient can have an aqueous solubility greater than 100 mg/mL, greater than 150 mg/mL, greater than 200 mg/mL, greater than 250 mg/mL, greater than 300 mg/mL, greater than 350 mg/mL, greater than 400 mg/mL, greater than 500 mg/mL, greater than 600 mg/mL An active pharmaceutical ingredient can have an aqueous solubility, for example, from 100 mg/mL to 600 mg/mL, from 200 mg/mL to 500 mg/mL, or from 250 mg/mL to 450 mg/mL.

Aqueous solubility is determined by high pressure liquid chromatography (HPLC).

Examples of active pharmaceutical ingredients having a water solubility greater than 100 mg/mL include acetohydroxamic acid, aliskiren, amifostine, aminocaproic acid, aminolevulinic acid, aminophylline, ascorbic acid, benzethonium, benzphetamine, betazole, bretylium, bromotheophylline, brompheniramine, bronopol, bupropion hydrochloride, folinic acid, captopril, carbamoylcholine, chloral hydrate, cidofovir, citrulline, clavulanic acid, clindamycin, codeine phosphate, cycloserine, cysteamine, cytarabine, d-glucose, dinoprost tromethamine, d-serine, dyphylline, edetic acid, emtricitabine, esketamine hydrochloride, arketamine hydrochloride, ethambutol hydrochloride, ferrous bisglycinate, flurazepam, fomepizole, framycetin, gabapentin, gamma-aminobutyric acid, gemifloxacin, gentamicin, gluconic acid, gluconolactone, glucosamine, glutathione, ibandronate, ibutilide, isoniazid, ketorolac, lactitol, lactose, lactulose, levamisole hydrochloride, levetiracetam, levocarnitine, lisdexamfetamine, mannitol, metformin hydrochloride, methenamine, methimazole, methyl aminolevulinate, migalastat hydrochloride, miglustat, nalmefene hydrochloride, naltrexone hydrochloride, neostigmine bromide, netilmicin, nicotinamide, nicotine, nitrofural, norfloxacin, ornithine, oxycodone, penicillamine, pentoxyverine, phenformin, phenylephrine, phenylpropanolamine, pidolic acid, piperazine, piracetam, pregabalin, procarbzine hydrochloride, promethazine hydrochloride, pyridoxine, pyruvic acid, ranitidine hydrochloride, rolitetracycline, ropinirole, scopolamine, selenomethionine, sodium ascorbate, sodium oxybate, terbutraline, thiamine hydrochloride, tobramycin, tranexamic acid, tromethamine salt, valacyclovir, and venlafaxine hydrochloride.

An active pharmaceutical ingredient having a water solubility greater than 100 mg/mL can include salt forms, hydrates, and/or solvates of a parent active pharmaceutical ingredient having a water solubility greater than 100 mg/mL where the parent active pharmaceutical ingredient has a water solubility less than 100 mg/mL.

An active pharmaceutical ingredient can comprise γ-hydroxybutyric acid or a derivative of γ-hydroxybutyric acid or a pharmaceutically acceptable salt of any of the foregoing. γ-Hydroxybutyric acid has the structure of Formula (1):

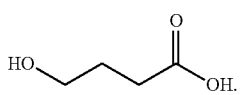

(1)

A derivative of γ-hydroxybutyric acid can have the structure of Formula (2):

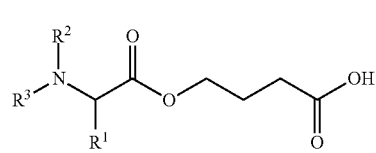

(2)

or a pharmaceutically acceptable salt thereof, where, $R^1$ can be selected from hydrogen and $C_{1-6}$ alkyl; and each of $R^2$ and $R^3$ can independently be selected from hydrogen, $C_{1-6}$ alkyl, $C_{1-6}$ alkoxycarbonyl, and $C_{3-8}$ cycloalkoxycarbonyl.

In compounds of Formula (2), $R^1$ can be selected from hydrogen and $C_{1-3}$ alkyl.

In compounds of Formula (2), $R^1$ can be selected from hydrogen, methyl, ethyl, n-propyl, and iso-propyl.

In compounds of Formula (2), $R^1$ can be hydrogen.

In compounds of Formula (2), $R^1$ can be methyl.

In compounds of Formula (2), $R^1$ can be iso-propyl.

In compounds of Formula (2), at least one of $R^2$ and $R^3$ can be selected from hydrogen and $C_{1-3}$ alkyl.

In compounds of Formula (2), each of $R^2$ and $R^3$ can independently be selected from hydrogen and $C_{1-3}$ alkyl.

In compounds of Formula (2), each of $R^2$ and $R^3$ can be hydrogen.

In compounds of Formula (2), $R^1$ can be selected from hydrogen and $C_{1-3}$ alkyl; and $R^2$ can be selected from $C_{1-6}$ alkoxycarbonyl and $C_{5-6}$ cycloalkoxycarbonyl.

In compounds of Formula (2), each of $R^2$ and $R^3$ can be hydrogen; and $R^1$ can be selected from hydrogen and $C_{1-3}$ alkyl.

In compounds of Formula (2), each of $R^2$ and $R^3$ can be hydrogen; and $R^1$ can be selected from hydrogen, methyl, ethyl, n-propyl, and iso-propyl.

In compounds of Formula (2), each of $R^2$ and $R^3$ can be hydrogen; and $R^1$ can be selected from hydrogen, methyl, and iso-propyl.

In compounds of Formula (2), the carbon atom to which $R^1$ is bonded can be in the (R)-configuration.

In compounds of Formula (2), the carbon atom to which IV is bonded can be in the (S)-configuration.

A compound of Formula (2) can be selected from:

4-(((tert-butoxycarbonyl)glycyl)oxy)butanoic acid;
4-(glycyloxy)butanoic acid;
4-((D-valyl)oxy)butanoic acid;
4-((L-alanyl)oxy)butanoic acid;
4-(((ethoxycarbonyl)glycyl)oxy)butanoic acid;
4-(((isopropoxycarbonyl)glycyl)oxy)butanoic acid;
4-((((cyclohexyloxy)carbonyl)glycyl)oxy)butanoic acid;
4-(((ethoxycarbonyl)-D-valyl)oxy)butanoic acid;
4-((L-valyl)oxy)butanoic acid;
a pharmaceutically acceptable salt of any of the foregoing; and
a combination of any of the foregoing.

A compound of Formula (2) can be 4-((L-valyl)oxy) butanoic acid (2a) or a pharmaceutically acceptable salt thereof:

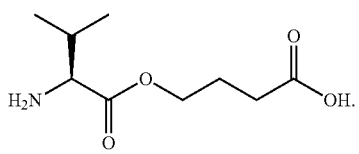

(2a)

A compound of Formula (2) can be 4-(glycyloxy)butanoic acid (2b) or a pharmaceutically acceptable salt thereof:

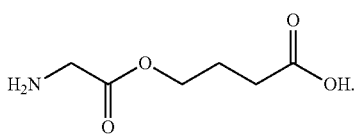

(2b)

A compound of Formula (2) can be 4-((L-alanyl)oxy)butanoic acid (2c) or a pharmaceutically acceptable salt thereof:

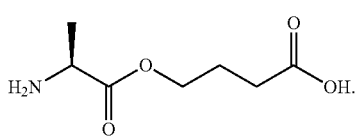

(2c)

Compounds of Formula (2)-(2c) are prodrugs of γ-hydroxybutyric acid, which when orally administered provide γ-hydroxybutyric acid in the blood of a patient. Compounds of Formula (2)-(2c) exhibit a relative oral bioavailability of γ-hydroxybutyric acid in a patient of greater than 10% F, greater than 20% F, greater than 30% F, greater than 40% F, greater than 50% F, or greater than 60% F.

Before forming into granules, the active pharmaceutical ingredient can have a low bulk density.

An active pharmaceutical ingredient can have a bulk density, for example, less than 0.20 g/mL, less than 0.30 g/mL, less than 0.40 g/mL, less than 0.50 g/mL, less than 0.6 g/mL, less than 0.7 g/mL, less than 0.8 g/mL, or less than 1.0 g/mL.

An active pharmaceutical ingredient can have a bulk density, for example, from 0.15 g/mL to 1.0 g/mL, from 0.15 g/mL to 8 g/mL, from 0.15 g/mL to 0.6 g/mL, from 0.15 g/mL to 0.4 g/mL, from 0.15 g/mL to 0.33 g/mL, from 0.16 g/mL to 0.32 g/mL, from 0.17 g/mL to 0.31 g/mL, from 0.18 g/mL to 0.30 g/mL, from 0.19 g/mL to 0.29 g/mL, or from 0.20 g/mL to 0.28 g/mL.

An active pharmaceutical ingredient can have a specific surface area, for example, from 200 $m^2$/kg to 1200 $m^2$/kg, such as from 400 $m^2$/kg to 1000 $m^2$/kg, wherein the specific surface area is determined using laser diffraction. An active pharmaceutical ingredient can have a specific surface area, for example, greater than 200 $m^2$/kg, greater than 400 $m^2$/kg, greater than 600 $m^2$/kg, greater than 800 $m^2$/kg, or greater than 1200 $m^2$/kg, where the specific surface area is determined by laser diffraction.

An active pharmaceutical ingredient can have a particle size distribution characterized, for example, by a D10 from 1 μm to 3 μm, a D50 from 6.5 μm to 8.5 μm, and a D90 from 15 μm to 17 μm, where particle size distribution is measured by laser diffraction.

Figure 11:
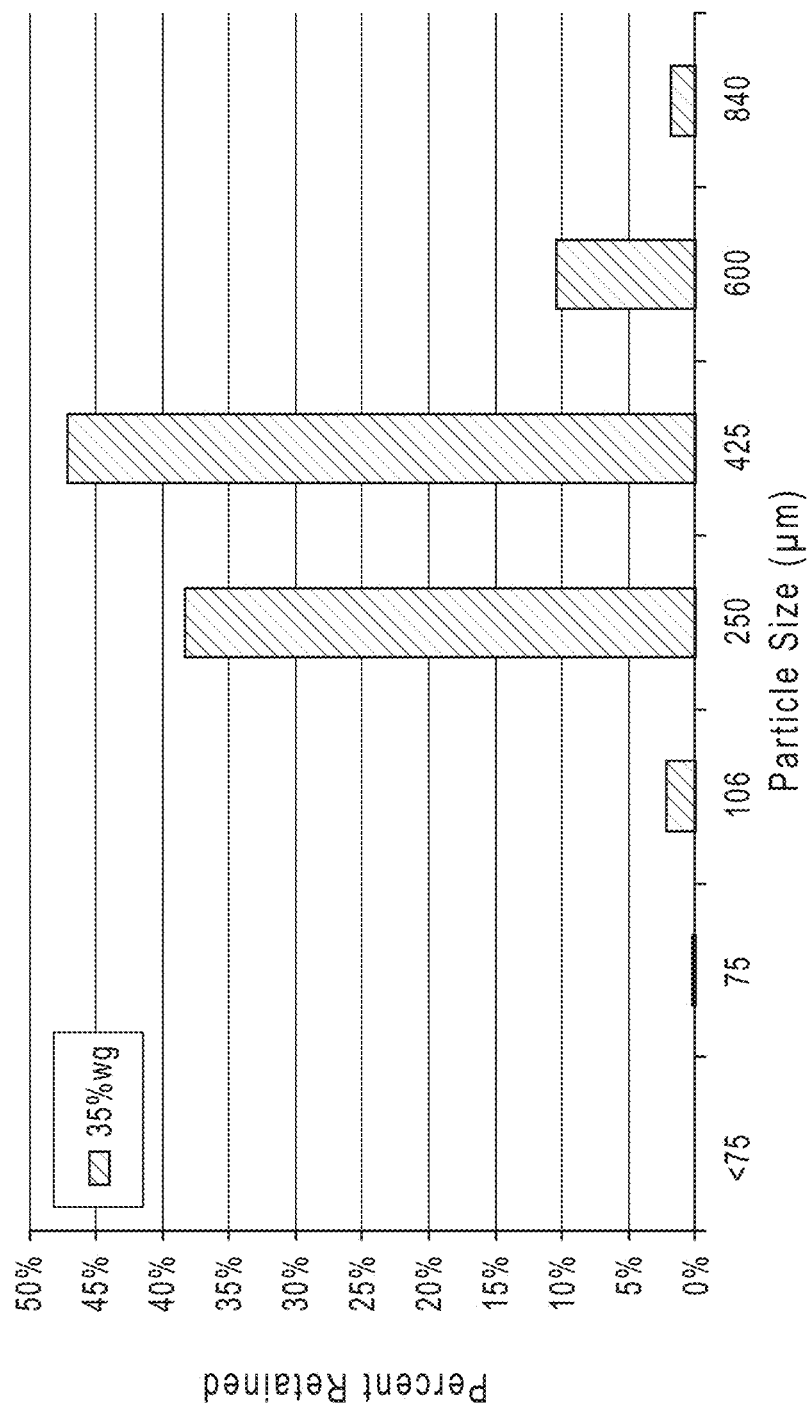
FIG. 11 shows the particle size distribution of coated granules comprising a 35% wg ethylcellulose/hydroxypropyl cellulose coating as described in Example 7.
Figure 15:
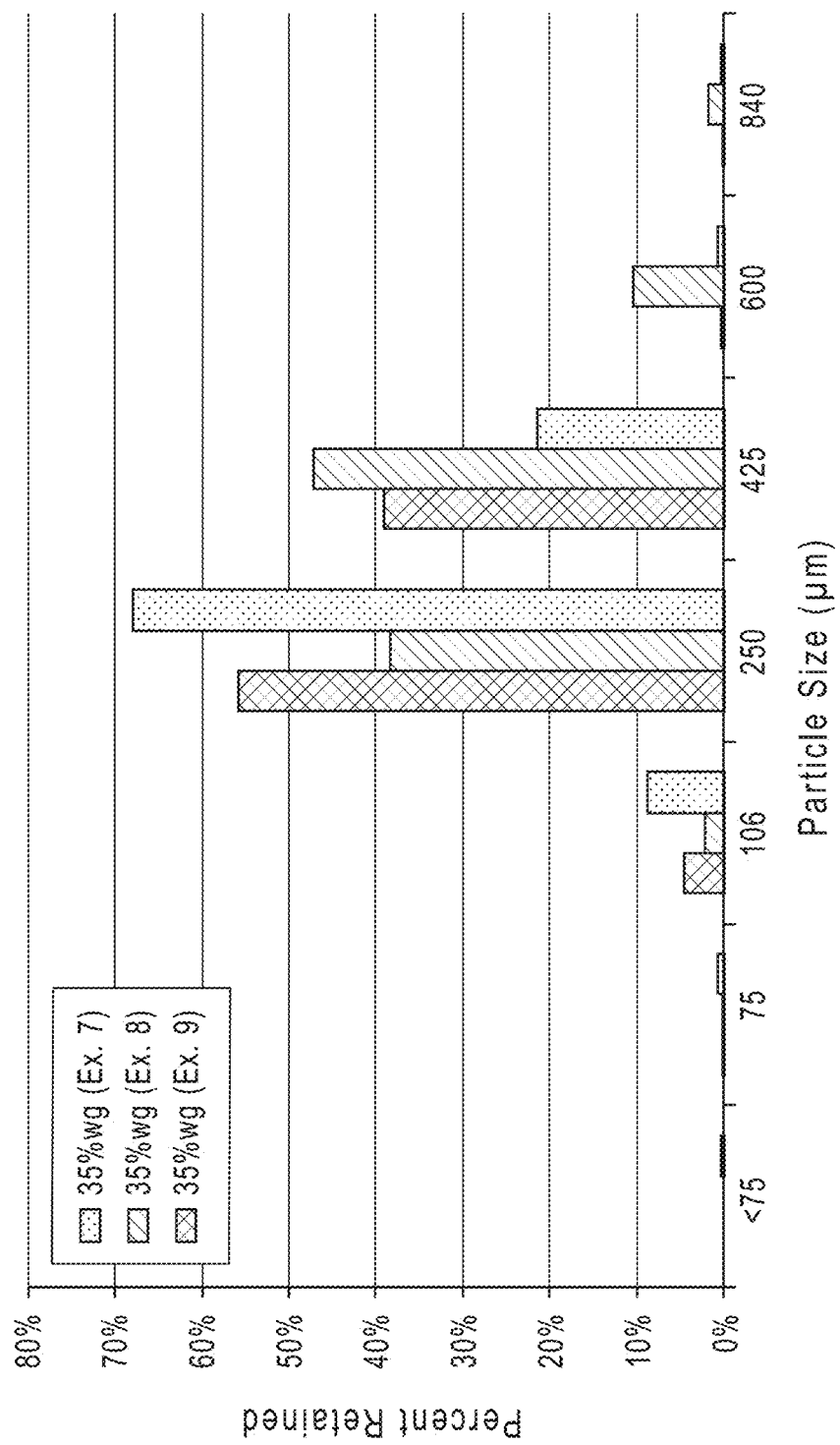
FIG. 15 shows particle size distributions of coated granules comprising a 35% wg ethylcellulose/hydroxypropyl cellulose coating as described in Examples 7, 8, and 9.

An active pharmaceutical ingredient can have a particle size distribution, for example, as substantially shown in any one of FIGS. 11 and 15.

An active pharmaceutical ingredient can be jet milled to reduce the particle size.

A jet-milled active pharmaceutical ingredient can have a particle size distribution, for example, less than 30 μm, less than 25 μm, less than 20 μm, or less than 15 μm.

An uncoated pharmaceutical granulation or uncoated granule can comprise, for example, from 95.0 wt % to 99.5 wt % of the active pharmaceutical ingredient; from 0.1 wt % to 1.0 wt % of a binder; and from 0.1 wt % to 2.0 wt % of an antistatic agent, wherein wt % is based on the total weight of the uncoated pharmaceutical granulation or uncoated granule.

An uncoated pharmaceutical granulation or uncoated granule can comprise, for example, from 98 wt % to 99 wt % of the active pharmaceutical ingredient; from 0.25 wt % to 0.75 wt % of a binder; and from 0.5 wt % to 1.5 wt % of an antistatic agent, wherein wt % is based on the total weight of the uncoated pharmaceutical granulation or uncoated granule.

An uncoated pharmaceutical granulation or uncoated granule can comprise, for example, from 98.25 wt % to 98.75 wt % of the active pharmaceutical ingredient; from 0.33 wt % to 0.65 wt % of a binder; and from 0.74 wt % to 1.25 wt % of an antistatic agent, wherein wt % is based on the total weight of the uncoated pharmaceutical granulation or uncoated granule.

An uncoated pharmaceutical granulation or uncoated granule can comprise, for example, from 85.0 wt % to 99.5 wt % of the active pharmaceutical ingredient; from 0.1 wt % to 8.0 wt % of a binder; and from 0.1 wt % to 8.0 wt % of an antistatic agent, wherein wt % is based on the total weight of the uncoated pharmaceutical granulation or uncoated granule.

An uncoated pharmaceutical granulation or granule can comprise, for example, from 85.0 wt % to 95.0 wt % of the active pharmaceutical ingredient; from 2.0 wt % to 7.0 wt % of a binder; and from 2.0 wt % to 7.0 wt % of an antistatic agent, wherein wt % is based on the total weight of the uncoated pharmaceutical granulation or uncoated granule.

An uncoated pharmaceutical granulation or granule can comprise, for example, from 87.0 wt % to 93.0 wt % of the active pharmaceutical ingredient; from 3.0 wt % to 7.0 wt % of a binder; and from 3.0 wt % to 7.0 wt % of an antistatic agent, wherein wt % is based on the total weight of the uncoated pharmaceutical granulation or uncoated granule.

An uncoated granulation can consist of an active pharmaceutical ingredient, a binder, and an antistatic agent. In addition to an active pharmaceutical ingredient, an uncoated granulation can consist of a binder consisting of hydroxypropyl cellulose and/or an antistatic agent consisting of talc. An uncoated granulation can consist of an active pharmaceutical ingredient selected from a compound of Formula (2), a binder wherein the binder consists of hydroxypropyl cellulose, and an antistatic agent wherein the antistatic agent consists of talc. An uncoated granulation can have trace amounts of water. In certain pharmaceutical compositions and granulations, the active pharmaceutical ingredient does not include 4-((L-valyl)oxy)butanoic acid (2a) or a pharmaceutically acceptable salt thereof:

An uncoated granule provided by the present disclosure can be characterized by a sphericity, for example, from 0.90 to 1, such as from 0.91 to 0.99, or from 0.92 to 0.98, where sphericity is determined using wet dispersion particle shape methods or by dynamic image analysis. An uncoated granule provided by the present disclosure can be characterized by a sphericity, for example, greater than 0.90, greater than 0.91, greater than 0.92, greater than 0.93, greater than 0.94, or greater than 0.95.

An uncoated pharmaceutical granulation provided by the present disclosure can be comprise a plurality of granules characterized by a mode sphericity, for example, from 0.90 to 1, such as from 0.91 to 0.99, or from 0.92 to 0.98, where sphericity is determined using wet dispersion particle shape methods or by dynamic image analysis. An uncoated pharmaceutical granulation provided by the present disclosure can comprise a plurality of granules characterized by an average sphericity, for example, greater than 0.94, greater than 0.95, greater than 0.96, greater than 0.97, greater than 0.98, or greater than 0.99.

Uncoated granules provided by the present disclosure are solid and are characterized by a substantially homogeneous composition throughout the granule.

For high dose active pharmaceutical ingredients, especially when reconstituted as a suspension before administration, to improve palatability it can be useful that the granules have a small mean diameter.

An uncoated pharmaceutical granulation provided by the present disclosure can be characterized, for example, by a particle size distribution (D50) from 75 μm to 500 μm, from 75 μm to 450 μm, from 75 μm to 450 μm, from 100 μm to 400 μm, from 150 μm to 350 μm, such as from 175 μm to 325 μm, from 200 μm to 300 μm, or from 225 μm to 275 μm. An uncoated pharmaceutical granulation provided by the present disclosure can be characterized, for example, by a particle size distribution (D50) of less than 400 μm, less than 360 μm, or less than 320 μm.

An uncoated pharmaceutical granulation can be characterized, for example, by a particle size distribution (D10) from 50 μm to 150 μm, from 60 μm to 140 μm, from 70 μm, to 120 μm, from 80 μm to 110 μm, from 50 μm to 150 μm, or from 50 μm to 200 μm. An uncoated pharmaceutical granulation can be characterized, for example, by a particle size distribution (D10) of less than 200 μm, less than 160 μm, or less than 120 μm.

An uncoated pharmaceutical granulation can be characterized, for example, by a particle size distribution (D90) from 450 μm to 800 μm, 450 μm to 750 μm, from 475 μm to 725 μm, from 500 μm to 700 μm, from 525 μm to 675 μm, or from 550 μm to 650 μm. An uncoated pharmaceutical granulation can be characterized, for example, by a particle size distribution (D90) of less than 800 μm, less than 700 μm, less than 600 μm, or less than 500 μm.

An uncoated pharmaceutical granulation can be characterized, for example, by a particle size distribution (D10) from 50 μm to 150 μm; a particle size distribution (D50) from 220 μm to 320 μm; and a PSD (D90) from 480 μm to 560 μm. An uncoated granulation can be characterized by a particle size distribution D50, for example, less than 500 μm, less than 450 μm, less than 400 μm, less than 350 μm, less than 300 μm less than 250 μm, or less than 200 μm.

An uncoated pharmaceutical granulation can be characterized, for example, by a particle size distribution (D10) from 60 μm to 140 μm; a particle size distribution (D50) from 230 μm to 310 μm; and a particle size distribution (D90) from 490 μm to 550 μm.

An uncoated pharmaceutical granulation can be characterized, for example, by a particle size distribution (D10) from 70 μm to 130 μm; a particle size distribution (D50) from 240 μm to 300 μm; and a particle size distribution (D90) from 500 μm to 540 μm.

Figure 18:
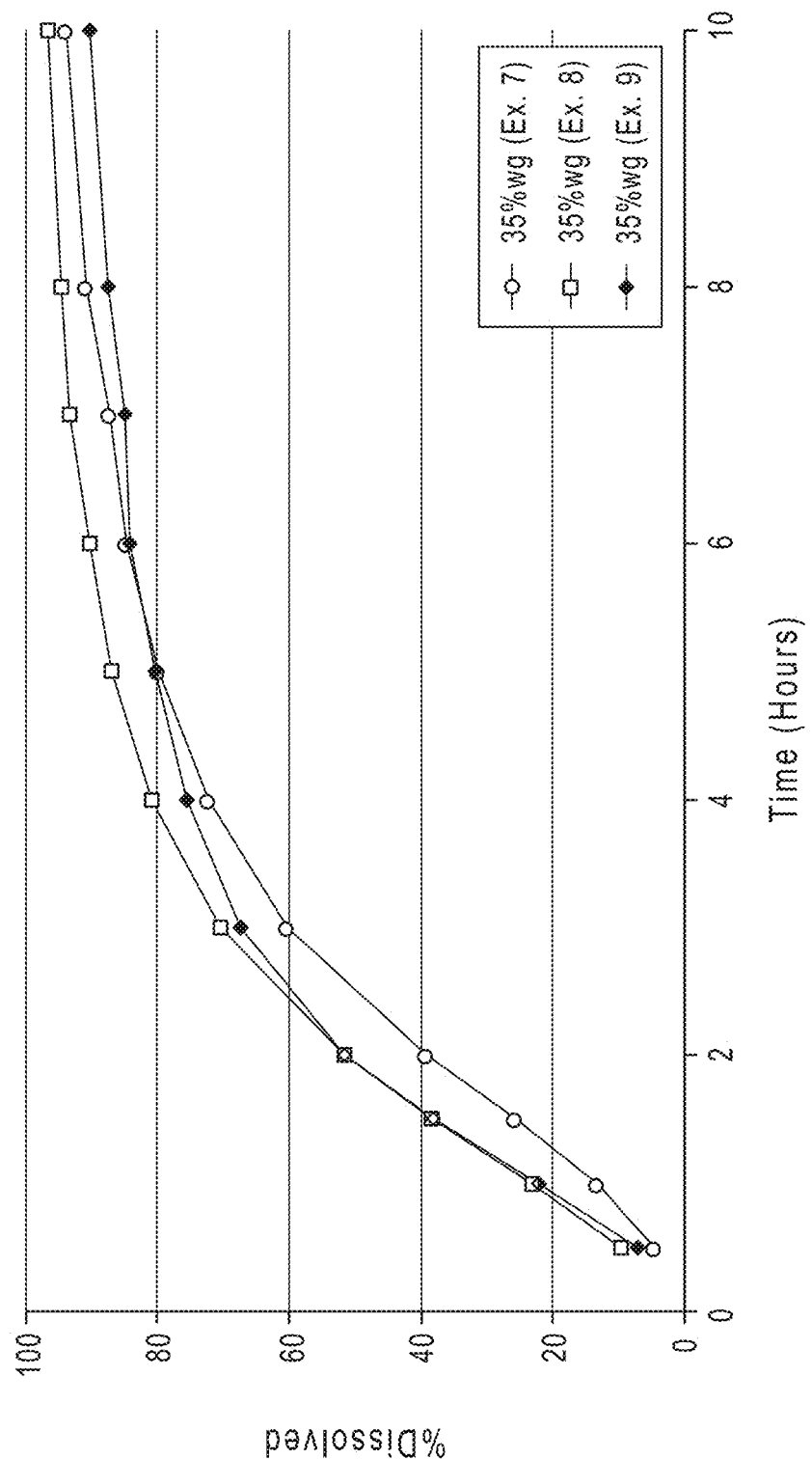
FIG. 18 shows dissolution profiles of an active pharmaceutical ingredient from granules having a 35% wg ethylcellulose/hydroxypropyl cellulose coating as described in Examples 7, 8, and 9.
Figure 19:
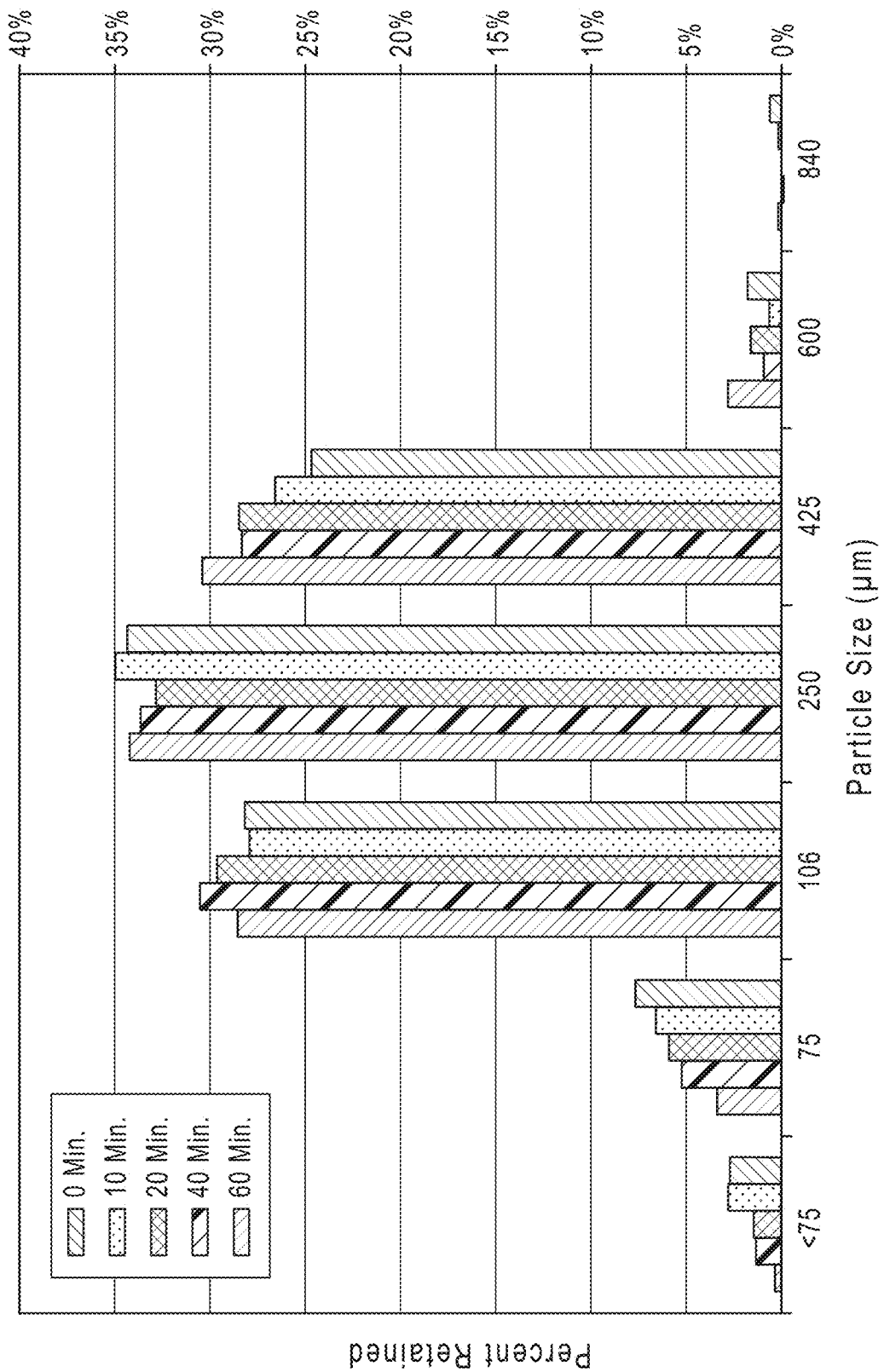
FIG. 19 shows particle size distributions for an uncoated pharmaceutical granulation prepared as described in Example 1.
Figure 20A:
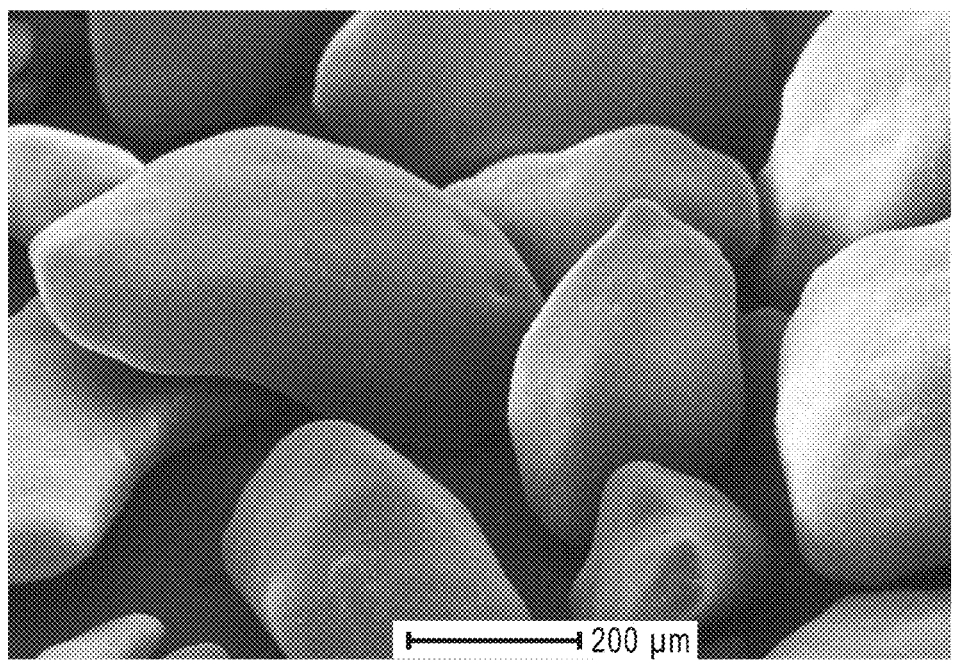
FIGS. 20A-20D show SEM images of the uncoated pharmaceutical granulation described in Example 1 at different magnifications.
Figure 20B:
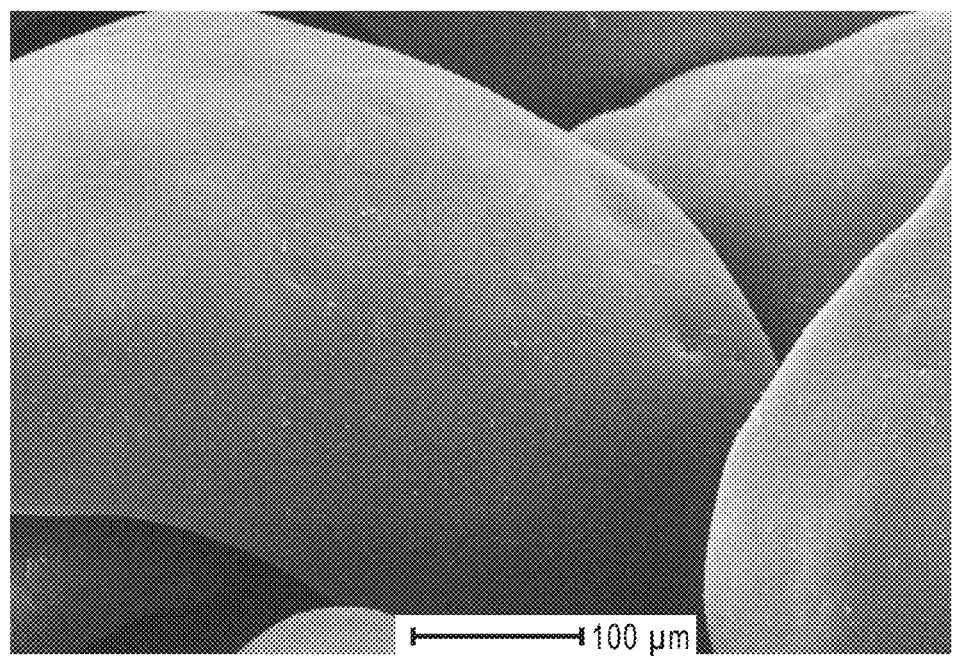
Figure 20C:
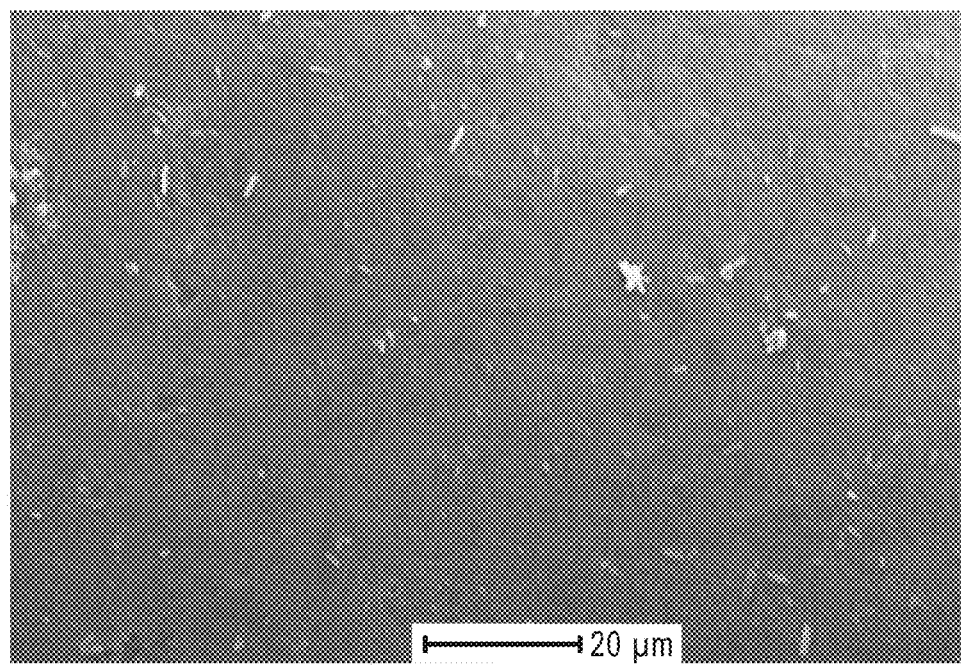
Figure 20D:
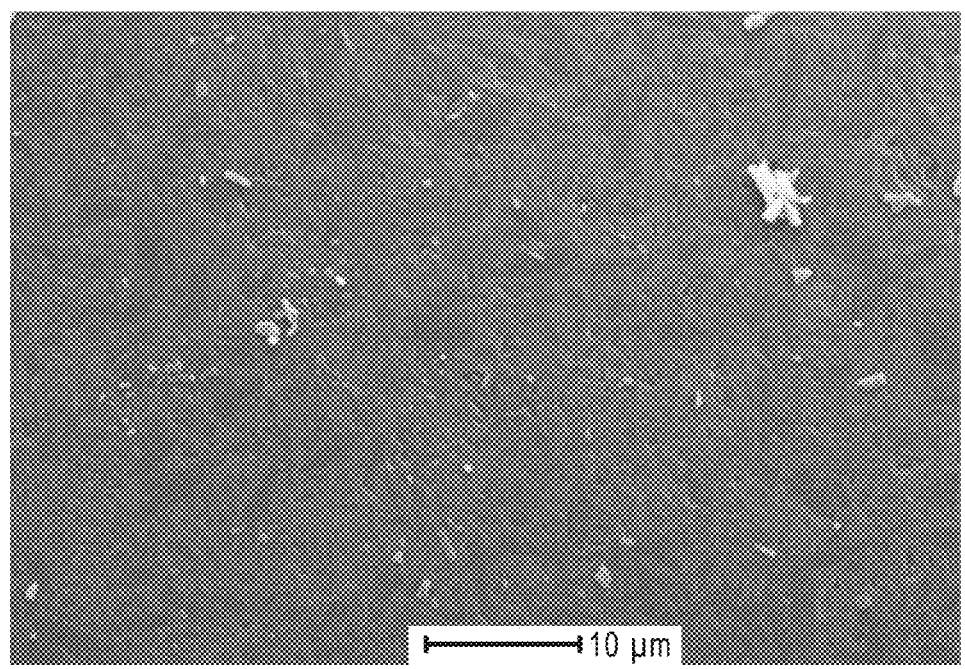

Examples of particle size distributions for uncoated granulations provided by the present disclosure is shown in FIG. 18.

A particle size distribution can be determined by laser diffraction or by sieve analysis.

An uncoated pharmaceutical granulation can have a bulk density, for example, greater than 0.40 g/mL, greater than 0.50 g/mL, greater than 0.60 g/mL, greater than 0.90 g/mL, greater than 1.10 g/mL, greater than 1.30 g/mL, or greater than 1.50 g/mL.

A uncoated pharmaceutical granulation can have a bulk density, for example, from 0.40 g/mL to 1.60 g/mL, from 0.40 g/mL to 1.20 g/mL, from 0.40 g/mL to 0.80 g/mL, from 0.50 g/mL to 1.60 g/mL, from 0.50 g/mL to 1.40 g/mL, from 0.50 g/mL to 1.20 g/mL, from 0.60 g/mL to 1.60 g/mL, from 0.70 g/mL to 1.50 g/mL, from 0.80 g/mL to 1.40 g/mL, or from 1.00 g/mL to 1.20 g/mL.

An uncoated pharmaceutical granulation can have a bulk density, for example, from 0.60 g/mL to 1.60 g/mL, from 0.70 g/mL to 1.50 g/mL, from 0.80 g/mL to 1.40 g/mL, or from 1.00 g/mL to 1.20 g/mL.

Bulk density can be determined using a bulk density cylinder.

An uncoated pharmaceutical granulation or granule can have a bulk density, for example, from 0.5 g/mL to 1.0 g/mL, from 0.5 g/mL to 0.9 g/mL, from 0.5 g/mL to 0.8 g/mL, from 0.5 g/mL to 0.7 g/mL, or from 0.6 g/mL to 0.7 g/mL. An uncoated pharmaceutical granulation or granule can have a bulk density, for example, greater than 0.5 g/mL, greater than 0.6 g/mL, greater than 0.7 g/mL, greater than 0.8 g/mL, or greater than 0.9 g/mL.

Scanning electron micrograph (SEM) images of examples of uncoated granules provided by the present disclosure are shown in FIGS. 20A-20D with magnifications of 110×, 220×, 1,000×, and 2,000×, respectively. The uncoated granules shown in FIGS. 20A-20D are characterized by substantially smooth surfaces.

Smooth granule surfaces facilitate the ability to coat the granules with a thin, continuous functional coating having a substantially homogeneous thickness. The qualities of the coating can be important for controlled release formulations. For example, rough and/or porous surfaces tend to require a significantly higher amount of a functional coating to achieve a comparable release profile to smooth surfaces. In addition, coatings of rough and/or porous surfaces can lead to a variable dissolution or release profile.

An uncoated pharmaceutical granulation provided by the present disclosure can be characterized by a loss on drying (LOD), for example, from 0.92 to 0.98, from 0.93 to 0.97, or from 0.94 to 0.96. The LOD represents removal of water incorporated into the granules during preparation of the uncoated pharmaceutical.

LOD is determined by thermogravimetric analysis.

An uncoated pharmaceutical granulation provided by the present disclosure can be characterized by a friability value, for example, from 0% to 2%. Granules with low friability are easier to coat than are granules with high friability. Friability is defined as the amount of granules having a diameter less than 75 μm that are generated by subjecting a granulation to a sonic sifter operated at a vibration amplitude of 8 corresponding to 3,600 sonic energy pulses per minute for at least 2 minutes.

An uncoated pharmaceutical granulation provided by the present disclosure can have a friability, for example, of 1.02% where friability is determined using a sonic sifter.

Methods of making uncoated pharmaceutical granulations containing a high loading of highly water soluble active pharmaceutical ingredients are disclosed in U.S. application Ser. No. 17/350,478 filed on Jun. 17, 2021.

Coated pharmaceutical granulations provided by the present disclosure can comprise a plurality of uncoated granules coated with a functional coating. A functional coating can comprise, for example, an immediate release coating, a controlled release coating, a modified release coating, a sustained release coating, a pH-release coating, a pulsatile release coating, a timed-release coating, or a delayed release coating. A functional coating can be configured to release an active pharmaceutical ingredient from a coated granule or core, for example, over an intended period of time following ingestion and/or within an intended region of the gastrointestinal tract.

A coated pharmaceutical granule provided by the present disclosure can comprise one or more functional coatings.

Each of the one or more functional coatings can independently have an average thickness, for example, less than 300 µm, less than 200 µm, less than 150 µm, less than 100 µm, less than 50 µm, less than 40 µm, less than 30 µm, less than 25 µm, less than 20 µm, less than 10 µm, or less than 5 µm. Each of the one or more functional coatings can independently have an average thickness, for example, from 5 µm to 300 µm, from 5 µm to 200 µm, from 5 µm to 100 µm, from 5 µm to 50 µm, from 5 µm to 40 µm, from 5 µm to 30 µm, from 5 µm to 25 µm, from 5 µm to 20 µm, or from 5 µm to 15 µm.

A coated granule can comprise, for example, less than 50 wt % of a functional coating, less than 45 wt % of a functional coating, less than 40 wt %, less than 30 wt %, less than 20 wt %, or less than 10 wt % of a functional coating, where wt % is based on the total weight of the coated granule.

A coated granule can comprise, for example, from 1 wt % to 50 wt % of a functional coating, from 5 wt % to 50 wt %, from 10 wt % to 45 wt %, or from 15 wt % to 40 wt % of a functional coating, where wt % is based on the total weight of the coated granule.

Dosage forms containing a highly water-soluble active pharmaceutical ingredient can have a thick coating to reduce the release rate of the active pharmaceutical ingredient and/or increase the storage stability of the active pharmaceutical ingredient by minimizing or preventing ingress of moisture.

A coated granule or coated granulation can comprise, for example, greater than 50 wt % of an active pharmaceutical ingredient, greater than 55 wt %, greater than 60 wt %, greater than 70 wt %, greater than 80 wt %, or greater than 85 wt % of an active pharmaceutical ingredient, where wt % is based on the total weight of the coated granule or coated granulation.

A coated granule or coated granulation comprising a plurality of coated granules can comprise, for example, from 50 wt % to 95 wt % of an active pharmaceutical ingredient, from 55 wt % to 90 wt %, from 60 wt % to 85 wt %, from 65 wt % to 80 wt % or from 70 wt % to 75 wt % of an active pharmaceutical ingredient, where wt % is based on the total weight of the coated granule or coated granulation.

A coated granule can comprise a core, i.e., uncoated granule, and a functional coating surrounding the cores. A coated granule can comprise, for example, from 55 wt % to 90 wt % of a core, and from 10 wt % to 45 wt % of the functional coating, where wt % is based on the total weight of the coated granule. A coated granule can comprise, for example, from 60 wt % to 85 wt % of a core, and from 15 wt % to 40 wt % of the functional coating, where wt % is based on the total weight of the coated granule.

A functional coating can comprise a matrix polymer or combination of matrix polymers. A combination of matrix polymers can comprise a water-insoluble polymer and/or a water-soluble or pore forming polymer. The combination of matrix polymers can be selected to provide for a desired release profile of an active pharmaceutical ingredient in the gastrointestinal tract.

A functional coating can comprise, for example, from 55 wt % to 85 wt % of a matrix polymer, from 60 wt % to 85 wt %, from 65 wt % to 80 wt %, or from 70 wt % to 80 wt %, of a matrix polymer, where wt % is based on the total weight of the functional coating.

A functional coating can comprise, for example less than 85 wt % of a matrix polymer, less than 80 wt %, less than 75 wt %, less than 70 wt %, or less than 65 wt % of a matrix polymer, where wt % is based on the total weight of the functional coating.

A functional coating can comprise, for example, greater than 60% of a matrix polymer, greater than 65 wt %, greater than 70 wt %, greater than 75 wt %, or greater than 80 wt % of a matrix polymer, where wt % is based on the total weight of the functional coating.

A matrix polymer can comprise a water-insoluble polymer or combination of water-insoluble polymers.

Examples of suitable water insoluble polymers include ethylcellulose, polyvinyl acetates, polyacrylates, and polymethacrylates.

A water insoluble polymer can be ethylcellulose.

A water insoluble polymer such as ethylcellulose can have an average molecular weight, for example, from 25,000 Daltons, to 300,000 Daltons, such as from 50,000 Daltons to 200,000 Daltons, from 50,000 Daltons to 150,000 Daltons, or from 50,000 Daltons to 100,000 Daltons.

A water insoluble polymer such as ethylcellulose can have a viscosity, for example, less than 100 mPa×sec, less than 75 mPa×sec, less than 50 mPa×sec, less than 25 mPa×sec, less than 20 mPa×sec, or less than 15 mPa×sec, as determined using a Brookfield viscometer in an 80:20 mixture of toluene/ethanol.

Examples of suitable ethylcellulose polymers include Aqualon® T10 Pharm, N7 Pharm, N10 Pharm, N14 Pharm, N22 Pharm, N50 Pharm, and N100 Pharm polymers, available from Ashland. Other examples of suitable ethylcellulose polymers include Ethocel® Standard 7, Standard 10, Standard 14, Standard 20 polymers, available from Dupont.

A functional coating can comprise, for example, from 65 wt % to 100 wt % of a water insoluble polymer, from 65 wt % to 90 wt %, or from 70 wt % to 80 wt % of a water insoluble polymer, wherein wt % is based on the total weight of the functional coating. A functional coating can comprise, for example, greater than 65 wt % of a water insoluble polymer such as ethylcellulose, greater than 70 wt %, greater than 75 wt %, or greater than 80 wt % of a water insoluble polymer, wherein wt % is based on the total weight of the functional coating.

A matrix polymer can comprise, for example, from 85 wt % to 100 wt % of a water-insoluble polymer, from 90 wt % to 100%, from 92 wt % to 98 wt %, from 91 wt % to 99 wt %, from 92 wt % to 98 wt %, or from 93 wt % to 97 wt % of a water-insoluble polymer, where wt % is based on the total weight of the matrix polymer. A matrix polymer can comprise, for example, greater than 85 wt % of a water insoluble polymer, greater than 90 wt %, greater than 92 wt %, greater than 94 wt %, greater than 96 wt %, or greater than 98 wt % of a water insoluble polymer, where wt % is based on the total weight of the matrix polymer. A matrix polymer can comprise, for example less than 100 wt % of a water insoluble polymer, less than 98 wt %, less than 96 wt %, less than 94 wt %, less than 92 wt %, less than 90 wt %, or less than 85 wt % of a water insoluble polymer, where wt % is based on the total weight of the matrix polymer.

A matrix polymer can comprise a pore forming polymer or combination of pore-forming polymers. A pore forming polymer refers to a water-soluble polymer.

Examples of pore formers include water-soluble polymers, polymers that swell or expand such as carbomers, and polymers soluble in gastric fluid such as cellulose acetate phthalate, hydroxypropyl cellulose, hydroxypropyl methyl cellulose, methacrylic acid-methyl methacrylate copolymers, and polyvinyl acetate phthalate. A pore forming polymer can increase the permeability of a functional coating under intended conditions.

A matrix polymer can comprise a water-soluble polymer or combination of water-soluble polymers.

Examples of suitable water-soluble polymers include hydroxypropyl cellulose, polyvinyl alcohol, hydroxypropylmethyl cellulose, hydroxypropylethyl cellulose, polyvinylpyrrolidone, polyethylene glycol, polyvinyl alcohol, povidone, crospovidone, and poloxamer.

A water-soluble polymer such as hydroxypropyl cellulose can have an average molecular weight, for example, less than 1,000,000 Daltons, less than 800,000 Daltons, less than 600,000 Daltons, less than 400,000 Daltons, less than 200,000 Daltons, less than 100,000 Daltons, or less than 50,0000 Daltons.

A water-soluble polymer such as hydroxypropyl cellulose can have a viscosity, for example, less than 7,000 mPa×sec, less than 5,000 mPa×sec, less than 3,000 mPa×sec, or less than 1,000 mPa×sec, as determined using a Brookfield viscometer in an 80:20 mixture of toluene/ethanol.

Examples of suitable hydroxypropyl cellulose polymers include Klucel® HF Pharm, MF Pharm, GF Pharm μF Pharm, LF Pharm, EF Pharm, and ELF Pharm polymers, available from Ashland.

Examples of suitable hydroxypropylmethyl cellulose polymers include Pharmacoat® 603, 645, 606 and 615 polymers, available from Shin-Etsu Chemical Co.

A matrix polymer can comprise, for example, from 0 wt % to 20 wt % of a water-soluble polymer, from 0 wt % to 10 wt %, from 0.5 wt % to 20 wt %, from 1 wt % to 10 wt %, from 1 wt % to 8 wt %, from 2 wt % to 7 wt %, from 2 wt % to 6 wt %, or from 4 wt % to 6 wt %, of a water-soluble polymer, where wt % is based on the total weight of the matrix polymer. A matrix polymer can comprise, for example, greater than 0 wt % of a water-soluble polymer, greater than 2 wt %, greater than 4 wt %, greater than 6 wt %, greater than 8 wt %, greater than 10 wt %, or greater than 15 wt % of a water-soluble polymer, where wt % is based on the total weight of the matrix polymer. A matrix polymer can comprise, for example, less than 20 wt %, less than 15 wt %, less than 10 wt % of a water-soluble polymer, less than 8 wt %, less than 6 wt %, less than 4 wt %, or less than 2 wt % of a water-soluble polymer, where wt % is based on the total weight of the matrix polymer. In certain functional coatings, the matrix polymer does not include a water-soluble polymer such as hydroxypropyl cellulose A matrix polymer can comprise, for example, from 90 wt % to 100 wt % of a water-insoluble polymer and from 0 wt % to 10 wt % of a water-soluble polymer; from 92 wt % to 98 wt % of a water-insoluble polymer and from 2 wt % to 8 wt % of a water-soluble polymer; or from 94 wt % to 96 wt % of a water-insoluble polymer and from 4 wt % to 6 wt % of a water-soluble polymer, where wt % is based on the total weight of the matrix polymer.

A functional coating can comprise, for example, from 65 wt % to 90 wt % of a water-insoluble polymer and from 1 wt % to 10 wt % of a water-soluble polymer; from 70 wt % to 85 wt % of a water-insoluble polymer and from 2 wt % to 8 wt % of a water-soluble polymer; or from 72 wt % to 83 wt % of a water-insoluble polymer and from 3 wt % to 7 wt % of a water-soluble polymer, where wt % is based on the total weight of the functional coating.

In addition to a matrix polymer or combination of matrix polymers, a functional coating can comprise, for example, a plasticizing agent, an anti-static, an anti-tacking agent, a colorant or pigment, a glidant, a viscosity modifier, or a combination of any of the foregoing.

A functional coating can comprise an antistatic agent or combination of antistatic agents.

An antistatic agent can be useful to minimize or prevent agglomeration of the granules during application of the functional coating.

Examples of suitable antistatic agents include talc, magnesium stearate, and silicon dioxide.

An antistatic agent can comprise talc.

An antistatic agent can comprise magnesium stearate. In certain functional coatings, the antistatic agent does not comprise magnesium stearate.

A functional coating can comprise, for example, from 10 wt % to 20 wt % of an antistatic agent, such as from 12 wt % to 18 wt %, or from 14 wt % to 16 wt % of an antistatic agent, where wt % is based on the total weight of the functional coating. A functional coating can comprise, for example, less than 20 wt % of an antistatic agent, less than 18 wt %, less than 16 wt %, less than 14 wt % or less than 12 wt % of an antistatic agent, where wt % is based on the total weight of the functional coating. A functional coating can comprise, for example, greater than 10 wt % of an antistatic agent, greater than 12 wt %, greater than 14 wt %, greater than 16 wt %, or greater than 18 wt % of an antistatic agent, where wt % is based on the total weight of the functional coating.

A functional coating can comprise a plasticizer or combination of plasticizers.

A plasticizer can be useful to provide a functional coating having a uniform thickness.

Examples of suitable plasticizers include dibutyl sebacate, polyethylene glycol, triacetin, and triethyl citrate.

A plasticizer can comprise dibutyl sebacate.

In certain functional coatings, the functional coating does not comprise a plasticizer.

A functional coating can comprise, for example, from 0 wt % to 14 wt % of a plasticizer, such as from 2 wt % to 12 wt %, or from 4 wt % to 10 wt % of a plasticizer, where wt % is based on the total weight of the functional coating. A functional coating can comprise, for example, less than 14 wt % of a plasticizer, less than 12 wt %, less than 12 wt %, less than 8 wt %, less than 6 wt %, or less than 4 wt % of a plasticizer, where wt % is based on the total weight of the functional coating. A functional coating can comprise, for example, greater than 0 wt % of a plasticizer, greater than 2 wt %, greater than 4 wt %, greater than 6 wt %, greater than 8 wt %, greater than 10 wt %, or greater than 12 wt % of a plasticizer, where wt % is based on the total weight of the functional coating.

A functional coating provided by the present disclosure can comprise, for example, from 60 wt % to 85 wt % of a matrix polymer, from 10 wt % to 20 wt % of an antistatic agent, and from 0 wt % to 14 wt % of a plasticizer, where wt % is based on the total weight of the functional coating.

A functional coating provided by the present disclosure can comprise, for example, from 65 wt % to 80 wt % of a matrix polymer, from 12 wt % to 18 wt % of an antistatic agent, and from 2 wt % to 12 wt % of a plasticizer, where wt % is based on the total weight of the functional coating.

A functional coating provided by the present disclosure can comprise, for example, from 70 wt % to 80 wt % of a matrix polymer, from 14 wt % to 16 wt % of an antistatic agent, and from 4 wt % to 10 wt % of a plasticizer, where wt % is based on the total weight of the functional coating.

A functional coating provided by the present disclosure can comprise, for example, a water-insoluble polymer such as ethylcellulose, a water-soluble polymer such as hydroxypropyl cellulose, an antistatic agent such as talc, and a plasticizer such as dibutyl sebacate.

Pharmaceutical granulations provided by the present disclosure can comprise a seal coating. Pharmaceutical granulations comprising a seal coating can be used as immediate release pharmaceutical granulations.

A coated granule provided by the present disclosure can comprise a seal coat overlying a granule comprising the active pharmaceutical ingredient. A functional coating can overly the seal coat.

A seal coat can minimize the ingress of moisture into the active pharmaceutical ingredient and thereby increase the storage stability of the coated granulation by reducing hydrolysis of the active pharmaceutical ingredient. A seal coat can also minimize negative interactions between the functional coating and the active pharmaceutical ingredient, and thereby increase the storage stability of the coated granulation by reducing hydrolysis of the active pharmaceutical ingredient.

A seal coat can comprise a water-soluble polymer such as, for example, hydroxypropyl cellulose, polyvinyl alcohol, hydroxypropylmethyl cellulose, hydroxypropylethyl cellulose, polyvinylpyrrolidone, or polyethylene glycol.

A seal coat can comprise a water-soluble polymer such as hydroxypropyl cellulose, hydroxypropylmethyl cellulose or any of the water-soluble polymers disclosed herein.

A seal coat can comprise an antistatic agent such as talc, magnesium stearate, or a combination thereof.

A seal coat can comprise, for example, hydroxypropyl cellulose, hydroxypropyl cellulose and talc, or hydroxypropylmethyl cellulose and talc.

A seal coat can comprise, for example, from 65 wt % to 95 wt % of a water soluble polymer, such as from 70 wt % to 90 wt %, or from 75 wt % to 85 wt % of a water soluble polymer; and from 5 wt % to 35 wt % of an antistatic agent, such as from 10 wt % to 30 wt %, or from 15 wt % to 25 wt % if an antistatic agent where wt % is based on the total weight of the seal coating.

A seal coat can have an average thickness, for example from 0.5 µm to 5 µm, from 1 µm to 4 µm, or from 1 µm to 3 µm. A seal coat can have an average thickness, for example, less than 5 µm, less than 4 µm, less than 3 µm, less than 2 µm, or less than 1 µm.

A seal coat can be applied to a granulation such that the % wg is less than 15% wg, less than 10% wg, less than 8% wg, less than 6% wg, or less than 4% wg. A seal coat can be applied to a granulation such that the % wg is from 1% wg to 15% wg, from 1% wg to 10% wg, from 2% wg to 8% wg, or from 4% wg to 6% wg.

In certain coated granulations comprising a seal coating comprising a water-soluble polymer, the functional coating does not contain a water-soluble polymer.

A seal coat can be applied to uncoated granules using any suitable method such as by spraying a solution, suspension, or dispersion of the functional coating onto granules in a fluidized bed apparatus.

A functional coating can be applied to uncoated granules provided by the present disclosure or to granules comprising a seal coat by any suitable method such as by spraying a solution, suspension, or dispersion of the functional coating onto granules in a fluidized bed apparatus.

A controlled release granulation provided by the present disclosure can comprise granules having a functional coating provided by the present disclosure.

A controlled release granulation provided by the present disclosure can be configured to provide for once a night dosing, once a day dosing (QD), twice a day dosing (BID), three times a day dosing (TID), or four times a day dosing (QID). For example, a controlled release granulation can release substantially 100% of the active pharmaceutical ingredient over a 24-hour duration, a 12-hour duration, an 8-hour duration, or a 4-hour duration.

For example, a controlled release granulation can exhibit a dissolution profile as substantially shown, for example, in FIG. 16, 17, 18, or 22.

A controlled release granulation can exhibit a dissolution profile in which less than 80% of the active pharmaceutical ingredient is released from the controlled release granulation within 2 hours, less than 70%, less than 60%, less than 50% or less than 40% is of active pharmaceutical ingredient is released from the controlled release granulation within 2 hours, and greater than 80% or greater than 90% of the active pharmaceutical ingredient is released from the controlled release granulation within 6 hours as determined using a USP Type 2 dissolution apparatus in a buffered solution at pH 4.5 at a temperature of 37° C. and a paddle speed of 75 rpm.

A controlled release granulation can exhibit a dissolution profile in which from 35% to 85%, such as from 35% to 80%, from 40% to 75%, or from 45% to 70% of the active pharmaceutical ingredient is released from the controlled release granulation within 2 hours as determined using a USP Type 2 dissolution apparatus in a buffered solution at pH 4.5 at a temperature of 37° C. and a paddle speed of 75 rpm.

A controlled release granulation can exhibit a dissolution profile in which from 70% to 95%, such as from 70% to 90%, or from 75% to 85% of the active pharmaceutical ingredient is released from the controlled release granulation within 4 hours as determined using a USP Type 2 dissolution apparatus in a buffered solution at pH 4.5 at a temperature of 37° C. and a paddle speed of 75 rpm.

A controlled release granulation can exhibit a dissolution profile in which from 80% to 100%, such as from 85% to 95%, of the active pharmaceutical ingredient is released from the controlled release granulation within 6 hours as determined using a USP Type 2 dissolution apparatus in a buffered solution at pH 4.5 at a temperature of 37° C. and a paddle speed of 75 rpm.

A controlled release granulation can exhibit a dissolution profile in which from 35% to 85% of the active pharmaceutical ingredient is released from the controlled release granulation within 2 hours, from 70% to 95% of the active pharmaceutical ingredient is released from the controlled release granulation within 4 hours, and from 80% to 100% of the active pharmaceutical ingredient is released from the formulation within 6 hours, as determined using a USP Type 2 dissolution apparatus in a buffered solution at pH 4.5 at a temperature of 37° C. and a paddle speed of 75 rpm.

A controlled release granulation can exhibit a dissolution profile in which from 35% to 80% of the active pharmaceutical ingredient is released from the controlled release granulation within 2 hours, from 70% to 90% of the active pharmaceutical ingredient is released from the controlled release granulation within 4 hours, and from 80% to 100% of the active pharmaceutical ingredient is released from the formulation within 6 hours, as determined using a USP Type 2 dissolution apparatus in a buffered solution at pH 4.5 at a temperature of 37° C. and a paddle speed of 75 rpm.

A controlled release granulation can exhibit a dissolution profile in which from 45% to 70% of the active pharmaceutical ingredient is released from the controlled release granulation within 2 hours, from 75% to 85% of the active pharmaceutical ingredient is released from the controlled release granulation within 4 hours, and from 85% to 95% of the active pharmaceutical ingredient is released from the controlled release granulation within 6 hours, as determined using a USP Type 2 dissolution apparatus in a buffered solution at pH 4.5 at a temperature of 37° C. and a paddle speed of 75 rpm.

A coated granulation provided by the present disclosure can have a water content, for example, less than 2 wt %, less than 1.5 wt % less than 1 wt %, less than 0.5 wt %, or less than 0.25 wt %, where wt % is based on the total weight of the granulation.

A coated granulation provided by the present disclosure can have a water content, for example, from 0.1 wt % to 2 wt %, from 0.1 wt % to 1 wt %, or from 0.2 wt % to 0.5 wt %, where wt % is based on the total weight of the granulation.

A coated pharmaceutical granulation can have a bulk density, for example, greater than 0.55 g/mL, greater than 0.60 g/mL, greater than 0.65 g/mL, greater than 0.70 g/mL, or greater than 0.75 g/mL.

A coated pharmaceutical granulation can have a bulk density, for example, from 0.55 g/mL to 0.80 g/mL, from 0.60 g/mL to 0.75 g/mL, from 0.60 g/mL to 0.70 g/mL.

Bulk density can be determined using a bulk density cylinder.

A coated pharmaceutical granulation provided by the present disclosure can be characterized, for example, by a particle size distribution (D50), for example, from 150 µm to 350 µm, such as from 175 µm to 325 µm, from 200 µm to 300 µm, or from 225 µm to 275 µm.

A coated pharmaceutical granulation can be characterized, for example, by a particle size distribution (D10) from 50 µm to 150 µm, from 60 µm to 140 µm, from 70 µm, to 120 µm, or from 80 µm to 110 µm.

An uncoated pharmaceutical granulation can be characterized, for example, by a particle size distribution (D90) from 450 µm to 750 µm, from 475 µm to 725 µm, from 500 µm to 700 µm, from 525 µm to 675 µm, or from 550 µm to 650 µm.

A coated pharmaceutical granulation can be characterized, for example, by a particle size distribution (D10) from 50 µm to 150 µm such as from 60 µm to 140 µm; a particle size distribution (D50) from 230 µm to 310 µm; and a particle size distribution (D90) from 490 µm to 550 µm.

A coated pharmaceutical granulation can be characterized, for example, by a particle size distribution (D10) from 70 µm to 130 µm; a particle size distribution (D50) from 240 µm to 300 µm; and a particle size distribution (D90) from 500 µm to 540 µm.

An example of a particle size distribution for an uncoated granulation provided by the present disclosure is shown in FIG. 15.

For example, in a coated pharmaceutical granulation 12.9% of the coated granules can have a particle size less than 300 µm, 83.8% of the coated granules can have a particle size from 300 µm to 600 µm, and 3.3% of the coated granules can have a particle size from 600 µm to 1190 µm.

A particle size distribution can be determined by laser diffraction or by sieve analysis.

Functional coatings and seal coatings provided by the present disclosure can be coated onto granulations using any suitable equipment and process. Examples of suitable coating methods include Wurster fluid bed film coating processes and phase inversion processes.

Examples of coating compositions are provided in the experimental examples. A coating composition refers to the composition that is applied to an uncoated granulation to provide a coated granulation.

A functional coating composition can comprise greater than 70 wt % of an alcoholic solvent, greater than 75 wt %, greater than 80 wt %, greater than 85 wt %, or greater than 90 wt % of an alcoholic solvent such as ethanol, where wt % is based on the total weight of the functional coating solution/suspension composition.

A functional coating composition can comprise, for example, less than 20 wt % water, less than 15 wt %, less than 10 wt %, or less than 5 wt % water, where wt % is based on the functional coating solution/suspension composition.

For highly water-soluble and hygroscopic active pharmaceutical ingredients it can be useful to minimize the amount of water in the functional coating composition. Reducing the level of water in the functional coating solution/suspension composition can lead to increased static which can complicate the coating process.

A functional coating solution/suspension composition can comprise, for example, a solids content less than 20 wt %, less than 18 wt %, less than 16 wt %, less than 14 wt %, less than 12 wt %, less than 10 wt %, less than 8 wt %, or less than 6 wt %, where wt % is based on the functional coating solution/suspension composition.

A functional coating composition can comprise a solids content from 2 wt % to 20 wt %, from 4 wt % to 16 wt %, from 4 wt % to 12 wt % or from 6 wt % to 10 wt %, where wt % is based on the functional coating composition.

A functional coating composition can comprise, for example, from 3 wt % to 10 wt % solids, from 4 wt % to 13 wt % water, from 75 wt % to 90 wt % of an alcoholic solvent such as ethanol, where wt % is based on the total weight of the functional coating composition.

Examples of coating process conditions using a Wurster column inserted into a fluid bed coating equipment are provided in the experimental examples.

A granulation provided by the present disclosure can comprise an immediate release granulation.

An immediate release granulation can comprise a plurality of uncoated granules. An immediate release granulation comprising a plurality of uncoated granules can comprise greater than 90 wt % of an active pharmaceutical ingredient provided by the present disclosure such as a compound of Formula (2). An immediate release granulation comprising uncoated granules can dissolve completely, for example, in less than 10 minutes, less than 8 minutes, less than 6 minutes, less than 5 minutes, or less than 4 minutes, when tested in a USP Type 2 dissolution apparatus in a buffered solution at pH 4.5 at a temperature of 37° C. and a paddle speed of 75 rpm.

An immediate release granulation can comprise a plurality of coated granules having an immediate release functional coating. An immediate release granulation comprising a plurality of coated granules can comprise greater than 80 wt % of an active pharmaceutical ingredient provided by the present disclosure such as a compound of Formula (2). An immediate release granulation comprising coated granules can dissolve completely, for example, in less than 25 minutes, less than 20 minutes, less than 18 minutes, less than 16 minutes, less than 14 minutes, or less than 12 minutes, when tested in a USP Type 2 dissolution apparatus in a buffered solution at pH 4.5 at a temperature of 37° C. and a paddle speed of 75 rpm. An immediate release granulation comprising coated granules can release greater than 80% of the active pharmaceutical ingredient, for example, in less than 10 minutes, less than 8 minutes, less than 6 minutes, or less than 4 minutes, when tested in a USP Type 2 dissolution apparatus in a buffered solution at pH 4.5 at a temperature of 37° C. and a paddle speed of 75 rpm. A coated immediate release granulation can comprise a coating comprising a water-soluble polymer such as, for example, hydroxypropyl cellulose, polyvinyl alcohol, hydroxypropylmethyl cellulose, hydroxypropylethyl cellulose, polyvinylpyrrolidone, or polyethylene glycol. A coated immediate release granulation can comprise a coating comprising an antistatic agent such as talc, magnesium stearate, or silicon dioxide.

A pharmaceutical composition provided by the present disclosure can comprise a combination of an immediate release granulation and a controlled release granulation. A pharmaceutical composition can comprise a weight ratio of a compound of Formula (2) as an immediate release granulation to a compound of Formula (2) as a controlled release granulation, for example, from 1:1 to 1:4, from 1:1 to 1:3, from 1:1 to 1:2 or from 1:2 to 1:3.

A pharmaceutical composition provided by the present disclosure can comprise a coated granulation provided by the present disclosure.

A pharmaceutical composition can comprise any suitable dosage form for oral administration.

Examples of suitable oral dosage forms include tablets, capsules, caplets, sachets, bottles, stick packs, dispersions, and suspensions.

A pharmaceutical composition provided by the present disclosure can comprise a suspension for oral administration.

An oral dosage form provided by the present disclosure can comprise, for example, from 0.1 grams to 20 grams of an active pharmaceutical ingredient, from 0.1 grams to 15 grams, from 0.1 grams to 12 grams, from 0.1 grams to 10 grams, from 0.2 grams to 8 grams, from 0.5 grams to 5 grams, from 1 gram to 4.5 grams, or from 1.5 grams to 4 grams of an active pharmaceutical ingredient. An oral dosage form can comprise, for example, greater than 0.5 grams, greater than 1 gram, greater than 2 grams, greater than 3 grams, greater than 4 grams, greater than 6 grams, or greater than 8 grams greater than 10 grams, greater than 14 grams, or greater than 18 grams of an active pharmaceutical ingredient.

An oral formulation provided by the present disclosure can comprise an oral suspension of coated granules having a controlled release functional coating provided by the present disclosure. An oral formulation can comprise a controlled release granulation provided by the present disclosure and an immediate release granulation.

An oral formulation can comprise a combination of an immediate release granulation and a controlled release granulation provided by the present disclosure.

An oral formulation provided by the present disclosure can provide a therapeutically effective amount of an active pharmaceutical ingredient over a period of time.

For example, an oral formulation provided by the present disclosure can provide a therapeutically effective amount of an active pharmaceutical ingredient over a period of 3 hours, 6 hours, 8 hours, or 10 hours.

An oral formulation provided by the present disclosure can provide a therapeutically effective amount of an active pharmaceutical ingredient over a period from 4 hours to 12 hours, from 4 hours to 10 hours, or from 4 hours to 8 hours.

An oral formulation provided by the present disclosure can provide a therapeutically effective amount of an active pharmaceutical ingredient over a duration from 1 hour to 12 hours following oral administration, from 2 hours to 10 hours or from 4 hours to 8 hours following oral administration.

An oral formulation provided by the present disclosure can be a once nightly formulation. For a once nightly formulation, a patient can administer a dose of an active pharmaceutical ingredient before going to bed and sleep through the night such as for 6 hours or for 8 hours without having to administer a second dose during the night.

An oral formulation provided by the present disclosure can provide a therapeutically effective amount of a γ-hydroxybutyric acid in the plasma of a patient.

An oral formulation provided by the present disclosure can provide a therapeutically effective amount of γ-hydroxybutyric acid in the plasma of a patient for a period of 4 hours, 6, hours, 8 hours, or 10 hours following oral administration of the controlled release oral formulation.

An oral formulation provided by the present disclosure can provide a plasma concentration of γ-hydroxybutyric acid greater than 10 μg/mL for more than 4 hours, more than 6 hours, more than 8 hours, or more than 10 hours following oral administration of the controlled release oral formulation.

An oral formulation provided by the present disclosure can provide a plasma concentration of γ-hydroxybutyric acid greater than 15 μg/mL for more than 4 hours, more than 6 hours, more than 8 hours, or more than 10 hours following oral administration of the controlled release oral formulation.

An oral formulation provided by the present disclosure can provide a therapeutically effective amount of $C_{max}$ to $C_{min}$ ratio of γ-hydroxybutyric acid in the plasma of a patient from less than 3 or less than 2 for a duration of 4 hours, 6 hours, 8 hours, or 10 hours following oral administration of the controlled release oral formulation.

An oral formulation provided by the present disclosure can comprise a γ-hydroxybutyric acid derivative of Formula (2) and can comprise, for example, 0.5 g-equivalents γ-hydroxybutyric acid, 1 g-equivalents, 2 g-equivalents, 3 g-equivalents, 4 g-equivalents, 5 g-equivalents, 6 g-equivalents, 7 g-equivalents, 8 g-equivalents, 9 g-equivalents, 10 g-equivalents, 11 g-equivalents, or 12 g-equivalents γ-hydroxybutyric acid.

Oral formulations provided by the present disclosure can be provided, for example, as sachets containing a coated granulation provided the present disclosure. A sachet can be provided in different doses of the active pharmaceutical ingredient such as 0.5 g, 1 g, 2 g, 3 g, 4 g, 5 g, 6 g, 7 g, 8 g, 9 g, 10 g, 11 g, 10 g, 12 g, 15 g, or 20 g of the active pharmaceutical ingredient. The coated granulation can be combined, for example, with water to provide an orally ingestible dosage form.

γ-Hydroxybutyric acid and γ-hydroxybutyric acid derivatives of Formula (2) can be used to treat narcolepsy, excessive daytime sleepiness, cataplexy, excessive daytime sleepiness associated with narcolepsy, excessive daytime sleepiness associated with Parkinson's disease, excessive daytime sleepiness associated with multiple sclerosis, cataplexy associated with narcolepsy, fatigue, fatigue associated with Parkinson's diseases, fatigue associated with multiple sclerosis, and fibromyalgia γ-Hydroxybutyric acid and γ-hydroxybutyric acid derivatives of Formula (2) can be used to treat REM sleep behavior disorder, spasmodic dystonia, schizophrenia, insomnia, insomnia associated with schizophrenia, idiopathic hypersomnia, chronic fatigue syndrome, cluster headache, Alzheimer's disease, essential tremor, post-traumatic stress syndrome, insomnia associated with post-traumatic stress syndrome, and anxiety.

Compounds of Formula (2) are prodrugs of γ-hydroxybutyric acid that following oral administration provide an oral bioavailability of γ-hydroxybutyric acid in the systemic circulation of a patient.

The effectiveness of the treatment can be measured by one or more of the following criteria: increase in the mean sleep latency such as determined the Maintenance of Wakefulness Test (MWT); improvement in the Clinical Global Impression (CGI) rating of sleepiness; decrease in the number of cataplexy attacks (NCA) such as determined from the cataplexy frequency item in the Sleep and Symptoms Daily Diary; decrease in disturbed nocturnal sleep (DNS), the disturbed nocturnal events or the adverse respiratory events such as determined by polysomnographic (PSG) measures of sleep fragmentation; decrease in excessive daytime sleepiness (EDS) such as measured by patient report via the Epworth Sleepiness Scale (ESS); decrease in daytime sleepiness as measured by the Maintenance of Wakefulness Test based on EEG measures of wakefulness; decrease PSG transitions from N/2 to N/3 and REM sleep to wake and Ni sleep such a determined as described in the AASM Manual for the Scoring of Sleep and Associated Events; decrease in the number of arousals or wakenings such as determined from a PSG as defined by the American Academy of Sleep Medicine; improvement in sleep quality such as determined using (i) the Sleep and Symptom Daily Diary, (ii) Visual Analog Scale (VAS) for sleep quality and sleep diary, and/or (iii) VAS for the refreshing nature of sleep; and decrease in the Hypnagogic Hallucinations (HH) or sleep paralysis (SP) symptoms in NT1 narcolepsy patients such as measured by the Sleep and Symptom Daily Diary.

Compounds of Formula (2) and pharmaceutical compositions thereof can be used to treat a disease known to be or determined to be treated by γ-hydroxybutyric acid.

Compounds of Formula (2) and pharmaceutical compositions thereof can be used to treat a disease known to be or determined to be treated by γ-hydroxybutyric acid and one or more additional therapeutic agents.

Compounds of Formula (2) and pharmaceutical composition can be used to treat excessive daytime sleepiness associated with narcolepsy, excessive daytime sleepiness associated with Parkinson's disease, excessive daytime sleepiness associated with multiple sclerosis, cataplexy associated with narcolepsy, fatigue in a patient with Parkinson's disease, fatigue in a patient with multiple sclerosis, or fibromyalgia.

Methods provided by the present disclosure include providing a therapeutically effective amount of γ-hydroxybutyric acid in the systemic circulation of a patient comprising administering to a patient a compound of Formula (2) or a pharmaceutically acceptable salt thereof, or a pharmaceutical composition thereof.

A pharmaceutical composition provided by the present disclosure may further comprise one or more active pharmaceutical compounds in addition to a compound of Formula (2). Such compounds may be provided to treat the disease being treated with the compound of Formula (2) or to treat a disease, disorder, or condition other than that being treated with the compound of Formula (2).

A compound of Formula (2) or a pharmaceutical composition thereof may be used in combination with at least one other therapeutic agent. A compound of Formula (2) or a pharmaceutical composition thereof may be administered to a patient together with another compound for treating a bacterial infection in the patient. The at least one other therapeutic agent may be a different compound encompassed by Formula (2). A compound of Formula (2) and the at least one other therapeutic agent may act additively or synergistically. The at least one additional therapeutic agent may be included in the same pharmaceutical composition or vehicle comprising the compound of Formula (2) or may be in a separate pharmaceutical composition or vehicle. Accordingly, methods provided by the present disclosure further include, in addition to administering a compound of Formula (2), administering one or more therapeutic agents effective for treating a different disease, disorder or condition other than the disease being treated with γ-hydroxybutyric acid. Methods provided by the present disclosure include administration of a compound of Formula (2) or a pharmaceutical composition thereof and one or more other therapeutic agents provided that the combined administration does not inhibit the therapeutic efficacy of a compound of Formula (2) and/or γ-hydroxybutyric acid and/or does not produce adverse combination effects.

A pharmaceutical composition comprising a compound of Formula (2) may be administered concurrently with the administration of another therapeutic agent, which may be part of the same pharmaceutical composition as, or in a different pharmaceutical composition than that comprising a compound of Formula (2). A compound of Formula (2) or a pharmaceutical composition thereof may be administered prior or subsequent to administration of another therapeutic agent. In certain embodiments of combination therapy, the combination therapy may comprise alternating between administering a compound of Formula (2) and a pharmaceutical composition comprising another therapeutic agent such as to minimize adverse drug effects associated with a particular drug. When a compound of Formula (2) is administered concurrently with another therapeutic agent that potentially may produce an adverse drug effect including, for example, toxicity, the other therapeutic agent may be administered at a dose that falls below the threshold at which the adverse drug reaction is elicited.

A pharmaceutical composition comprising a compound of Formula (2) may be administered with one or more substances, for example, to enhance, modulate and/or control release, bioavailability, therapeutic efficacy, therapeutic potency, and/or stability of a compound of Formula (2). For example, to enhance the therapeutic efficacy of a compound of Formula (2), a compound of Formula (2) or a pharmaceutical composition comprising a compound of Formula (2) may be co-administered with one or more active agents to increase the absorption or diffusion and/or transport of the compound of Formula (2) from the gastrointestinal tract into the systemic circulation, or to inhibit degradation of the compound of Formula (2) in the blood of a patient. A pharmaceutical composition comprising a compound of Formula (2) may be co-administered with an active agent having pharmacological effects that enhance the therapeutic efficacy of the compound of Formula (2) or γ-hydroxybutyric acid.

ASPECTS OF THE INVENTION

The invention is further defined by the following aspects.

Aspect 1. A pharmaceutical granulation comprising a plurality of coated granules comprising a core and a functional coating surrounding the core, wherein, the pharmaceutical granulation is characterized by a particle size distribution (PSD) (D50) from 150 µm to 400 µm, wherein particle size distribution is determined by sieve analysis; and the core comprises greater than 90 wt % of an active pharmaceutical ingredient, wherein wt % is based on the total weight of the core.

Aspect 2. The pharmaceutical granulation of aspect 1, wherein the pharmaceutical granulation comprises from 60 wt % to 85 wt % of the active pharmaceutical ingredient, where wt % is based on the total weight of the pharmaceutical granulation.

Aspect 3. The pharmaceutical granulation of any one of aspects 1 to 2, wherein the functional coating comprises a controlled release coating.

Aspect 4. The pharmaceutical granulation of any one of aspects 1 to 3, wherein the functional coating comprises from 60 wt % to 85 wt % of a matrix polymer, wherein wt % is based on the total weight of the functional coating.

Aspect 5. The pharmaceutical granulation of aspect 4, wherein the matrix polymer comprises a water-insoluble polymer.

Aspect 6. The pharmaceutical granulation of aspect 5, wherein the water-insoluble polymer comprises ethylcellulose.

Aspect 7. The pharmaceutical granulation of any one of aspects 1 to 6, wherein the functional coating comprises from 0 wt % to 10 wt % of a pore forming polymer, wherein wt % is based on the total weight of the polymers.

Aspect 8. The pharmaceutical granulation of aspect 7, wherein the pore forming polymer comprises a water-soluble polymer.

Aspect 9. The pharmaceutical granulation of aspect 8, wherein the water-soluble polymer comprises hydroxypropyl cellulose.

Aspect 10. The pharmaceutical granulation of any one of aspects 1 to 9, wherein the functional coating comprises from 0 wt % to 14 wt % of a plasticizer, wherein wt % is based on the total weight of the functional coating.

Aspect 11. The pharmaceutical granulation of aspect 10, wherein the plasticizer comprises dibutyl sebacate.

Aspect 12. The pharmaceutical granulation of any one of aspects 1 to 11, wherein the functional coating comprises from 10 wt % to 20 wt % an antistatic agent, wherein wt % is based on the total weight of the functional coating.

Aspect 13. The pharmaceutical granulation of aspect 12, wherein the antistatic agent comprises talc.

Aspect 14. The pharmaceutical granulation of any one of aspects 12 to 13, wherein the functional coating comprises: from 60 wt % to 85 wt % of a matrix polymer; from 10 wt % to 20 wt % of an antistatic agent; and from 0 wt % to 14 wt % of a plasticizer, wherein wt % is based on the total weight of the functional coating.

Aspect 15. The pharmaceutical granulation of any one of aspects 1 to 14, wherein, the core represents from 65 wt % to 85 wt % of the total weight of the coated granules; and the functional coating represents from 15 wt % to 35 wt % of the total weight of the coated granules.

Aspect 16. The pharmaceutical granulation of any one of aspects 1 to 15, wherein the functional coating has a thickness from 5 µm to 20 µm.

Aspect 17. The pharmaceutical granulation of any one of aspects 1 to 16, wherein the pharmaceutical granulation has a water content less than 1 wt %, wherein wt % is based on the total weight of the pharmaceutical granulation.

Aspect 18. The pharmaceutical granulation of any one of aspects 1 to 17, further comprising a seal coating surrounding the core, and wherein the functional coating surrounds the seal coating.

Aspect 19. The pharmaceutical granulation of aspect 18, wherein the seal coating comprises hydroxypropyl cellulose.

Aspect 20. The pharmaceutical granulation of any one of aspects 18 to 19, wherein the granules comprise from 2 wt % to 15 wt % of the seal coating.

Aspect 21. The pharmaceutical granulation of any one of aspects 1 to 20, wherein from 35% to 80% of the active pharmaceutical ingredient is released from the formulation within 2 hours when tested in a USP Type 2 dissolution apparatus in a buffered solution at pH 4.5 at a temperature of 37° C. and a paddle speed of 75 rpm.

Aspect 22. The pharmaceutical granulation of any one of aspects 1 to 20, wherein from 70% to 90% of the active pharmaceutical ingredient is released from the formulation within 4 hours when tested in a USP Type 2 dissolution apparatus in a buffered solution at pH 4.5 at a temperature of 37° C. and a paddle speed of 75 rpm.

Aspect 23. The pharmaceutical granulation of any one of aspects 1 to 20, wherein from 80% to 100% of the active pharmaceutical ingredient is released from the formulation within 6 hours when tested in a USP Type 2 dissolution apparatus in a buffered solution at pH 4.5 at a temperature of 37° C. and a paddle speed of 75 rpm.

Aspect 24. The pharmaceutical granulation of any one of aspects 1 to 23, wherein the active pharmaceutical ingredient has an aqueous solubility greater than 100 mg/mL.

Aspect 25. The pharmaceutical granulation of any one of aspects 1 to 23, wherein the active pharmaceutical ingredient has an aqueous solubility from 100 mg/mL to 1,000 mg/mL.

Aspect 26. The pharmaceutical granulation of any one of aspects 1 to 25, wherein the active pharmaceutical ingredient comprises γ-hydroxybutyric acid or a pharmaceutically acceptable salt thereof.

Aspect 27. The pharmaceutical granulation of any one of aspects 1 to 26, wherein the active pharmaceutical ingredient comprises a derivative of γ-hydroxybutyric acid or a pharmaceutically acceptable salt thereof.

Aspect 28. The pharmaceutical granulation of any one of aspects 1 to 27, wherein the active pharmaceutical ingredient comprises a compound of Formula (2):

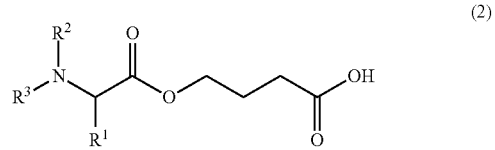

(2)

or a pharmaceutically acceptable salt thereof, wherein, $R^1$ is selected from hydrogen and $C_{1-6}$ alkyl; and each of $R^2$ and $R^3$ is independently selected from hydrogen, $C_{1-6}$ alkyl, $C_{1-6}$ alkoxycarbonyl, and $C_{3-6}$ cycloalkoxycarbonyl.

Aspect 29. The pharmaceutical granulation of aspect 28, wherein the active pharmaceutical ingredient is selected from:
4-(((tert-butoxycarbonyl)glycyl)oxy)butanoic acid;
4-(glycyloxy)butanoic acid;
4-((D-valyl)oxy)butanoic acid;
4-((L-alanyl)oxy)butanoic acid;
4-(((ethoxycarbonyl)glycyl)oxy)butanoic acid;
4-(((isopropoxycarbonyl)glycyl)oxy)butanoic acid;
4-((((cyclohexyloxy)carbonyl)glycyl)oxy)butanoic acid;
4-(((ethoxycarbonyl)-D-valyl)oxy)butanoic acid;
4-((L-valyl)oxy)butanoic acid;
a pharmaceutically acceptable salt of any of the foregoing; and
a combination of any of the foregoing.

Aspect 30. The pharmaceutical granulation of aspect 28, wherein the active pharmaceutical ingredient comprises 4-((L-valyl)oxy)butanoic acid (2a) or a pharmaceutically acceptable salt thereof:

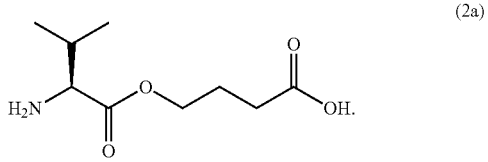

(2a)

Aspect 31. A pharmaceutical composition comprising the pharmaceutical granulation of any one of aspects 1 to 30.

Aspect 32. The pharmaceutical composition of aspect 31, wherein the pharmaceutical composition is an oral formulation.

Aspect 33. The pharmaceutical composition of any one of aspects 31 to 32, wherein the pharmaceutical composition is a controlled release formulation.

Aspect 34. The pharmaceutical composition of any one of aspects 31 to 33, wherein the pharmaceutical composition comprises:
a controlled release portion, wherein the controlled release portion comprises the pharmaceutical granulation of claim 1; and
the pharmaceutical composition n further comprises an immediate release portion, an extended release portion, or a combination thereof.

Aspect 35. The pharmaceutical composition of any one of aspects 31 to 34, wherein the pharmaceutical composition is a BID formulation.

Aspect 36. The pharmaceutical composition of any one of aspects 31 to 34, wherein the pharmaceutical composition is a QD formulation.

Aspect 37. The pharmaceutical composition of any one of aspects 31 to 36, wherein the pharmaceutical composition comprises from 500 mg equivalents to 12 g equivalents of γ-hydroxybutyric acid or a pharmaceutically acceptable salt thereof.

Aspect 38. The pharmaceutical composition of any one of aspects 31 to 37, wherein the active pharmaceutical ingredient comprises γ-hydroxybutyric acid or a pharmaceutically acceptable salt thereof, a derivative of γ-hydroxybutyric acid or a pharmaceutically acceptable salt thereof, a compound of Formula (2) or a pharmaceutically acceptable salt thereof, or a combination of any of the foregoing.

Aspect 39. The pharmaceutical composition of aspect 38, wherein the active pharmaceutical ingredient is selected from:
4-(((tert-butoxycarbonyl)glycyl)oxy)butanoic acid;
4-(glycyloxy)butanoic acid;
4-((D-valyl)oxy)butanoic acid;
4-((L-alanyl)oxy)butanoic acid;
4-(((ethoxycarbonyl)glycyl)oxy)butanoic acid;
4-(((isopropoxycarbonyl)glycyl)oxy)butanoic acid;
4-((((cyclohexyloxy)carbonyl)glycyl)oxy)butanoic acid;
4-(((ethoxycarbonyl)-D-valyl)oxy)butanoic acid;
4-((L-valyl)oxy)butanoic acid;
a pharmaceutically acceptable salt of any of the foregoing; and
a combination of any of the foregoing.

Aspect 40. The pharmaceutical composition of any one of aspects 38 to 39, wherein the pharmaceutical composition comprises a therapeutically effective amount of the active pharmaceutical ingredient for treating excessive daytime sleepiness associated with narcolepsy, excessive daytime sleepiness associated with Parkinson's disease, excessive daytime sleepiness associated with multiple sclerosis, cataplexy associated with narcolepsy, fatigue in a patient with Parkinson's disease, fatigue in a patient with multiple sclerosis, or fibromyalgia.

Aspect 41. A method of providing a therapeutically effective amount of γ-hydroxybutyric acid in the systemic circulation of a patent comprising administering to a patient in need thereof a therapeutically effective amount of the pharmaceutical composition of any one of aspects 38 to 39 for treating a disease.

Aspect 42. A method of treating a disease in a patient, wherein the disease is known to be treated by administering γ-hydroxybutyric acid, comprising administering to a patient in need thereof a therapeutically effective amount of the pharmaceutical composition of any one of aspects 38 to 39.

Aspect 43. A method of treating a disease in a patient, wherein the disease is known to be treated by administering γ-hydroxybutyric acid, comprising administering to a patient in need thereof, a therapeutically effective amount of the pharmaceutical composition of any one of aspects 38 to 39.

Aspect 44. The method of any one of aspects 41 to 43, wherein, following administration to the patient, the pharmaceutical composition provides a therapeutically effective amount of γ-hydroxybutyric acid in the systemic circulation of the patient for treating the disease.

Aspect 45. The method of any one of aspects 41 to 44, wherein administering comprises orally administering.

Aspect 46. The method of any one of aspects 41 to 45, wherein the disease is selected from excessive daytime sleepiness associated with narcolepsy, excessive daytime sleepiness associated with Parkinson's disease, excessive daytime sleepiness associated with multiple sclerosis, cataplexy associated with narcolepsy, fatigue in a patient with Parkinson's disease, fatigue in a patient with multiple sclerosis, and fibromyalgia.

Aspect 47. A method of coating a granulation comprising applying a coating formulation to a pharmaceutical granulation comprising a plurality of granules comprising an active pharmaceutical ingredient, wherein the coating formulation comprises from 4 wt % to 12 wt % solids; from 3 wt % to 7 wt % water; and from 82 wt % to 92 wt % ethanol.

Aspect 48. The method of aspect 47, wherein applying comprises spraying.

Aspect 49. The method of any one of aspects 47 to 48, the granules comprise an active pharmaceutical ingredient having an aqueous solubility greater than 100 mg/mL.

Aspect 1A. A pharmaceutical granulation comprising a plurality of coated granules, wherein, the coated granules comprise a core and a functional coating surrounding the core; the core comprises greater than 85 wt % of an active pharmaceutical ingredient, wherein the active pharmaceutical ingredient has an aqueous solubility greater than 100 mg/mL; and wt % is based on the total weight of the core; and the functional coating comprises a plasticizer.

Aspect 2A. The pharmaceutical granulation of aspect 1A, wherein the pharmaceutical granulation comprises from 50 wt % to 90 wt % of the active pharmaceutical ingredient, wherein wt % is based on the total weight of the pharmaceutical granulation.

Aspect 3A. The pharmaceutical granulation of any one of aspects 1A to 2A, wherein the functional coating comprises a controlled release coating.

Aspect 4A. The pharmaceutical granulation of any one of aspects 1A to 3A, wherein the functional coating comprises from 60 wt % to 85 wt % of a matrix polymer, wherein wt % is based on the total weight of the functional coating.

Aspect 5A. The pharmaceutical granulation of aspect 4A, wherein the matrix polymer comprises a water-insoluble polymer.

Aspect 6A. The pharmaceutical granulation of aspect 5A, wherein the water-insoluble polymer comprises ethylcellulose.

Aspect 7A. The pharmaceutical granulation of any one of aspects 1A to 6A, wherein the functional coating comprises from 0.5 wt % to 20 wt % of a water-soluble polymer, wherein wt % is based on the total weight of the matrix polymer.

Aspect 8A. The pharmaceutical granulation of aspect 7A, wherein the water-soluble polymer comprises hydroxypropyl cellulose.

Aspect 9A. The pharmaceutical granulation of any one of aspects 4A to 8A, wherein the matrix polymer comprises from 92 wt % to 98 wt % of a water-insoluble polymer and from 2 wt % to 8 wt % of a water-soluble polymer, wherein wt % is based on the total weight of the matrix polymer.

Aspect 10A. The pharmaceutical granulation of any one of aspects 1A to 9A, wherein the functional coating comprises from 3 wt % to 13 wt % of the plasticizer, wherein wt % is based on the total weight of the functional coating.

Aspect 11A. The pharmaceutical granulation of aspect 10A, wherein the plasticizer comprises dibutyl sebacate.

Aspect 12A. The pharmaceutical granulation of any one of aspects 1A to 11A, wherein the functional coating comprises from 10 wt % to 20 wt % an antistatic agent, wherein wt % is based on the total weight of the functional coating.

Aspect 13A. The pharmaceutical granulation of aspect 12A, wherein the antistatic agent comprises talc.

Aspect 14A. The pharmaceutical granulation of any one of aspects 1A to 13A, wherein the functional coating comprises from 60 wt % to 85 wt % of a matrix polymer; from 10 wt % to 20 wt % of an antistatic agent; and from 3 wt % to 13 wt % of the plasticizer, wherein wt % is based on the total weight of the functional coating.

Aspect 15A. The pharmaceutical granulation of any one of aspects 1A to 14A, wherein the coated granules comprise: from 55 wt % to 90 wt % of the core; and from 10 wt % to 45 wt % of the functional coating, wherein wt % is based on the total weight of the coated granules.

Aspect 16A. The pharmaceutical granulation of any one of aspects 1A to 15A, wherein the functional coating has a thickness from 5 μm to 30 μm.

Aspect 17A. The pharmaceutical granulation of any one of aspects 1A to 16A, wherein the pharmaceutical granulation has a water content less than 1 wt %, wherein wt % is based on the total weight of the pharmaceutical granulation.

Aspect 18A. The pharmaceutical granulation of any one of aspects 1A to 17A, wherein, the coated granules comprise a seal coating surrounding the core; and the functional coating surrounds the seal coating.

Aspect 19A. The pharmaceutical granulation of aspect 18A, wherein the seal coating comprises hydroxypropyl cellulose.

Aspect 20A. The pharmaceutical granulation of any one of aspects 18A to 19A, wherein the coated granules comprise from 2 wt % to 15 wt % of the seal coating, wherein wt % is based on the total weight of the granules.

Aspect 21A. The pharmaceutical granulation of any one of aspects 18A to 20A, wherein the seal coating has a thickness from 0.5 μm to 5 μm.

Aspect 22A. The pharmaceutical granulation of any one of aspects 1A to 21A, wherein the active pharmaceutical ingredient has an aqueous solubility greater than 100 mg/mL.

Aspect 23A. The pharmaceutical granulation of any one of aspects 1A to 21A, wherein the active pharmaceutical ingredient has an aqueous solubility from 100 mg/mL to 1,000 mg/mL.

Aspect 24A. The pharmaceutical granulation of any one of aspects 1A to 23A, wherein the active pharmaceutical ingredient comprises γ-hydroxybutyric acid or a pharmaceutically acceptable salt thereof.

Aspect 25A. The pharmaceutical granulation of any one of aspects 1A to 23A, wherein the active pharmaceutical ingredient comprises a derivative of γ-hydroxybutyric acid or a pharmaceutically acceptable salt thereof.

Aspect 26A. The pharmaceutical granulation of any one of aspects 1A to 23A, wherein the active pharmaceutical ingredient comprises a compound of Formula (2):

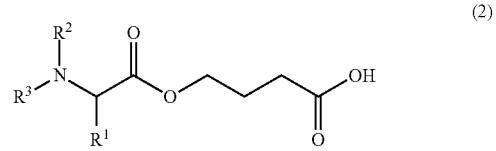

(2)

or a pharmaceutically acceptable salt thereof, wherein,
$R^1$ is selected from hydrogen and $C_{1-6}$ alkyl; and
each of $R^2$ and $R^3$ is independently selected from hydrogen, $C_{1-6}$ alkyl, $C_{1-6}$ alkoxycarbonyl, and $C_{3-6}$ cycloalkoxycarbonyl.

Aspect 27A. The pharmaceutical granulation of any one of aspects 1A to 23A, wherein the active pharmaceutical ingredient is selected from:
4-(((tert-butoxycarbonyl)glycyl)oxy)butanoic acid;
4-(glycyloxy)butanoic acid;
4-((D-valyl)oxy)butanoic acid;
4-((L-alanyl)oxy)butanoic acid;
4-(((ethoxycarbonyl)glycyl)oxy)butanoic acid;
4-(((isopropoxycarbonyl)glycyl)oxy)butanoic acid;
4-((((cyclohexyloxy)carbonyl)glycyl)oxy)butanoic acid;
4-(((ethoxycarbonyl)-D-valyl)oxy)butanoic acid;
4-((L-valyl)oxy)butanoic acid;
a pharmaceutically acceptable salt of any of the foregoing; and
a combination of any of the foregoing.

Aspect 28A. The pharmaceutical granulation of any one of aspects 1A to 23A, wherein the active pharmaceutical ingredient comprises 4-((L-valyl)oxy)butanoic acid (2a) or a pharmaceutically acceptable salt thereof:

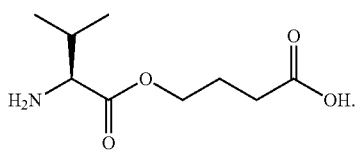

(2a)

Aspect 29A. The pharmaceutical granulation of any one of aspects 1A to 28A, wherein the coated granules are characterized by a particle size distribution (PSD) (D50) from 150 µm to 500 µm, wherein the particle size distribution is determined by laser diffraction.

Aspect 30A. The pharmaceutical granulation of any one of aspects 1A to 29A, wherein from 35% to 85% of the active pharmaceutical ingredient is released from the pharmaceutical granulation within 2 hours when tested in a USP Type 2 dissolution apparatus in a buffered solution at pH 4.5 at a temperature of 37° C. and a paddle speed of 75 rpm.

Aspect 31A. The pharmaceutical granulation of any one of aspects 1A to 30A, wherein from 70% to 95% of the active pharmaceutical ingredient is released from the pharmaceutical granulation within 4 hours when tested in a USP Type 2 dissolution apparatus in a buffered solution at pH 4.5 at a temperature of 37° C. and a paddle speed of 75 rpm.

Aspect 32A. The pharmaceutical granulation of any one of aspects 1A to 31A, wherein from 80% to 100% of the active pharmaceutical ingredient is released from the pharmaceutical granulation within 6 hours when tested in a USP Type 2 dissolution apparatus in a buffered solution at pH 4.5 at a temperature of 37° C. and a paddle speed of 75 rpm.

Aspect 33A. A pharmaceutical composition comprising the pharmaceutical granulation of any one of aspects 1A to 32A.

Aspect 34A. The pharmaceutical composition of aspect 33A, wherein the pharmaceutical composition is an oral formulation.

Aspect 35A. The pharmaceutical composition of aspect 34A, wherein the oral formulation comprises an oral suspension.

Aspect 36A. The pharmaceutical composition of any one of aspects 31A to 35A, wherein the pharmaceutical composition comprises: a controlled release portion, wherein the controlled release portion comprises the pharmaceutical granulation; and an immediate release portion, an extended release portion, or a combination thereof.

Aspect 37A. The pharmaceutical composition of any one of aspects 3A1 to 36A, wherein the immediate release portion comprises immediate release granules, wherein, the immediate release granules comprise a seal coating surrounding a core; and the core comprises greater than 85 wt % of the active pharmaceutical ingredient.

Aspect 38A. The pharmaceutical composition of any one of aspects 31A to 37A, wherein the pharmaceutical composition is a BID formulation.

Aspect 39A. The pharmaceutical composition of any one of aspects 31A to 38A, wherein the pharmaceutical composition is a QD formulation.

Aspect 40A. The pharmaceutical composition of any one of aspects 31A to 39A, wherein the pharmaceutical composition comprises from 500 mg equivalents to 12 g equivalents of γ-hydroxybutyric acid.

Aspect 41A. The pharmaceutical composition of any one of aspects 31A to 39A, wherein the active pharmaceutical ingredient comprises γ-hydroxybutyric acid or a pharmaceutically acceptable salt thereof, a derivative of γ-hydroxybutyric acid or a pharmaceutically acceptable salt thereof, a compound of Formula (2) or a pharmaceutically acceptable salt thereof, or a combination of any of the foregoing.

Aspect 42A. The pharmaceutical composition of any one of aspects 31A to 39A, wherein the active pharmaceutical ingredient comprises:
4-(((tert-butoxycarbonyl)glycyl)oxy)butanoic acid;
4-(glycyloxy)butanoic acid;
4-((D-valyl)oxy)butanoic acid;
4-((L-alanyl)oxy)butanoic acid;
4-(((ethoxycarbonyl)glycyl)oxy)butanoic acid;
4-(((isopropoxycarbonyl)glycyl)oxy)butanoic acid;
4-((((cyclohexyloxy)carbonyl)glycyl)oxy)butanoic acid;
4-(((ethoxycarbonyl)-D-valyl)oxy)butanoic acid;
4-((L-valyl)oxy)butanoic acid;
a pharmaceutically acceptable salt of any of the foregoing; or
a combination of any of the foregoing.

Aspect 43A. The pharmaceutical composition of any one of aspects 31A to 39A, wherein the active pharmaceutical ingredient comprises 4-((L-valyl)oxy)butanoic acid (2a) or a pharmaceutically acceptable salt thereof:

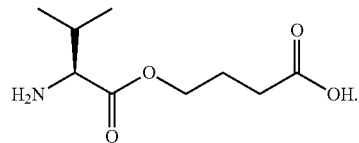

(2a)

Aspect 44A. The pharmaceutical composition of any one of aspects 40A to 42A, wherein the pharmaceutical composition comprises a therapeutically effective amount of the active pharmaceutical ingredient for treating excessive daytime sleepiness associated with narcolepsy, excessive daytime sleepiness associated with Parkinson's disease, excessive daytime sleepiness associated with multiple sclerosis, cataplexy associated with narcolepsy, fatigue in a patient with Parkinson's disease, fatigue in a patient with multiple sclerosis, or fibromyalgia.

Aspect 45A. A method of providing a therapeutically effective amount of γ-hydroxybutyric acid in the systemic circulation of a patent for treating a disease comprising administering to a patient in need of such treatment a therapeutically effective amount of the pharmaceutical composition of any one of aspects 40A to 43A for treating the disease.

Aspect 46A. A method of treating a disease in a patient, wherein the disease is known to be treated by administering γ-hydroxybutyric acid, comprising administering to a patient in need of such treatment a therapeutically effective amount of the pharmaceutical composition of any one of aspects 40 to 43A for treating the disease.

Aspect 47A. The method of any one of aspect 45A to 46A, wherein, following administration to the patient, the pharmaceutical composition provides a therapeutically effective amount of γ-hydroxybutyric acid in the systemic circulation of the patient for treating the disease.

Aspect 48A. The method of any one of aspects 45A to 47A, wherein administering comprises orally administering.

Aspect 49A. The method of any one of aspects 45A to 48A, wherein the disease is selected from excessive daytime sleepiness associated with narcolepsy, excessive daytime sleepiness associated with Parkinson's disease, excessive daytime sleepiness associated with multiple sclerosis, cataplexy associated with narcolepsy, fatigue in a patient with Parkinson's disease, fatigue in a patient with multiple sclerosis, and fibromyalgia.

Aspect 50A. A method of coating a pharmaceutical granulation comprising applying a coating composition to a pharmaceutical granulation comprising a plurality of granules, wherein the coating composition comprises: rom 4 wt % to 12 wt % solids; greater than 10 wt % water; and from 75 wt % to 92 wt % ethanol; wherein wt % is based on the total weight of the coating composition; and the granules comprise: a core comprising no less than 90 wt % of an active pharmaceutical ingredient; and the active pharmaceutical ingredient has an aqueous solubility greater than 100 mg/mL, wherein wt % is based on the total weight of the core.

Aspect 51A. The method of aspect 50A, wherein the solids comprise from 3 wt % to 13 wt % of a plasticizer, wherein wt % is based on the total weight of the solids.

Aspect 5A1. The method of any one of aspects 49A to 50A, wherein, rom 60 wt % to 85 wt % of a matrix polymer; and from 10 wt % to 20 wt % of an antistatic agent, herein wt % is based on the total weight of the solids.

Aspect 52A. The method of any one of aspects 49A to 51A, wherein the granules comprise a seal coating surrounding the core.

Aspect 53A. The method of any one of aspects 49A to 52A, wherein applying comprises spraying.

Aspect 54A. The method of any one of aspects 49A to 53A, wherein the method comprises drying the applied coating composition.

EXAMPLES

Embodiments provided by the present disclosure are further illustrated by reference to the following examples, which describe uncoated pharmaceutical granulations, uncoated pharmaceutical granules, coated pharmaceutical granulations, coated pharmaceutical granules, oral controlled release pharmaceutical compositions and methods of making the coated pharmaceutical granulations and granules provided by the present disclosure. It will be apparent to those skilled in the art that many modifications, both to materials, and methods, may be practiced without departing from the scope of the disclosure.

Example 1

Granulation of Active Pharmaceutical Ingredient

Granulations of an active pharmaceutical ingredient were prepared as described in Examples 7-9 of U.S. application Ser. No. 17/350,478.

An active pharmaceutical ingredient used to prepare the pharmaceutical granulations was the compound of Formula (2a), 4-((L-valyl)oxy)butanoic acid, and had a purity of 99.3%.

An active pharmaceutical ingredient having a bulk density of 0.263 g/mL was passed through a Comil® fitted with a 0.056-inch screen. Prior to co-milling the active pharmaceutical ingredient was stored in a dry environment.

The constituents of the dry mixture in terms of wt % were 98.5 wt % active pharmaceutical ingredient, 0.5 wt % binder, and 1 wt % antistatic agent.

Distilled water (4.7 wt %) was added to the dry mixture using a pump and a 2-fluid spray nozzle with atomizing air set to 4 psi.

The granulation was retained in a jacketed 4-liter bowl throughout processing.

The wet granulation was granulated for 9.7 minutes at a mixer speed of 850 rpm and a chopper speed of 3,600 rpm.

The wet granulation was wet massed for up to 60 minutes at a mixer speed of 547 rpm and a chopper speed of 1,800 rpm, while the temperature of the wet granulation was maintained between 23.1° C. and 23.6° C. During wet massing a chiller was attached to the bowel to maintain the temperature less than 25° C.

The granulation was characterized by a granule bulk density from 0.68 g/mL to 0.714 g/mL and a friability of about 1.02%.

Uncoated pharmaceutical granulations having a granule diameter from 200 µm to 425 µm were used to prepare the coated pharmaceutical granulations described in the Examples.

Example 2

Coated Granulation (2)

The constituents of the functional coating formulation are provided in Table 1.

TABLE 1

Functional coating formulation.

| Component | Total (wt %) | Solids (wt %) |
|---|---|---|
| Eudragit® RS 100 ethylacrylate/methylmethacrylate copolymer | 5.62 | 56.25 |
| Eudragit® RL 100 ethylacrylate/methylmethacrylate copolymer | 0.62 | 6.25 |
| Triethyl citrate | 0.63 | 6.25 |
| Talc | 3.13 | 31.25 |
| Water | 4.5 | — |
| Ethanol, 100% | 85.5 | — |

The granulation was coated with the functional coating described in Table 1 using a Wurster column inserted in fluid bed. The coating conditions are provided in FIG. 21. The functional coating was applied to achieve a 10% wg or 20% wg.

The dissolution profile of the granulation was determined using a USP Type 2 dissolution apparatus a buffered solution at pH 4.5 at a temperature of 37° C. and a paddle speed of 75 rpm. The dissolution profiles are shown in FIG. 1. The designations 20% wg (1) and 20% wg (2) refer to two separate experiments using a granulation having a 20% wg coating.

Example 3

Coated Granulation (3)

A granulation containing granules having 98.5 wt % of the compound of Formula (2a), 4-((L-valyl)oxy)butanoic acid, and characterized by a granule diameter from 200 µm to 425 µm was used.

The constituents of the functional coating formulation are provided in Table 2.

TABLE 2

Functional coating formulation.

| Component | Total (wt %) | Solids (wt %) |
|---|---|---|
| Aqualon® EC N10 ethylcellulose | 5.54 | 69.16 |
| Klucel® HPC EF Hydroxypropyl cellulose | 0.62 | 7.74 |
| Dibutyl Sebacate | 0.62 | 7.74 |
| Talc | 1.23 | 15.36 |
| Water | 4.60 | — |
| Ethanol, 95% | 87.40 | — |

The granulation was coated with the functional coating described in Table 2 using a Wurster column inserted in fluid bed. The coating conditions are provided in FIG. 21. The functional coating was applied to achieve a 10% wg or 20% wg. Static build up increased during the coating process and agglomerates began to form at about a 10% wg.

Figure 2:
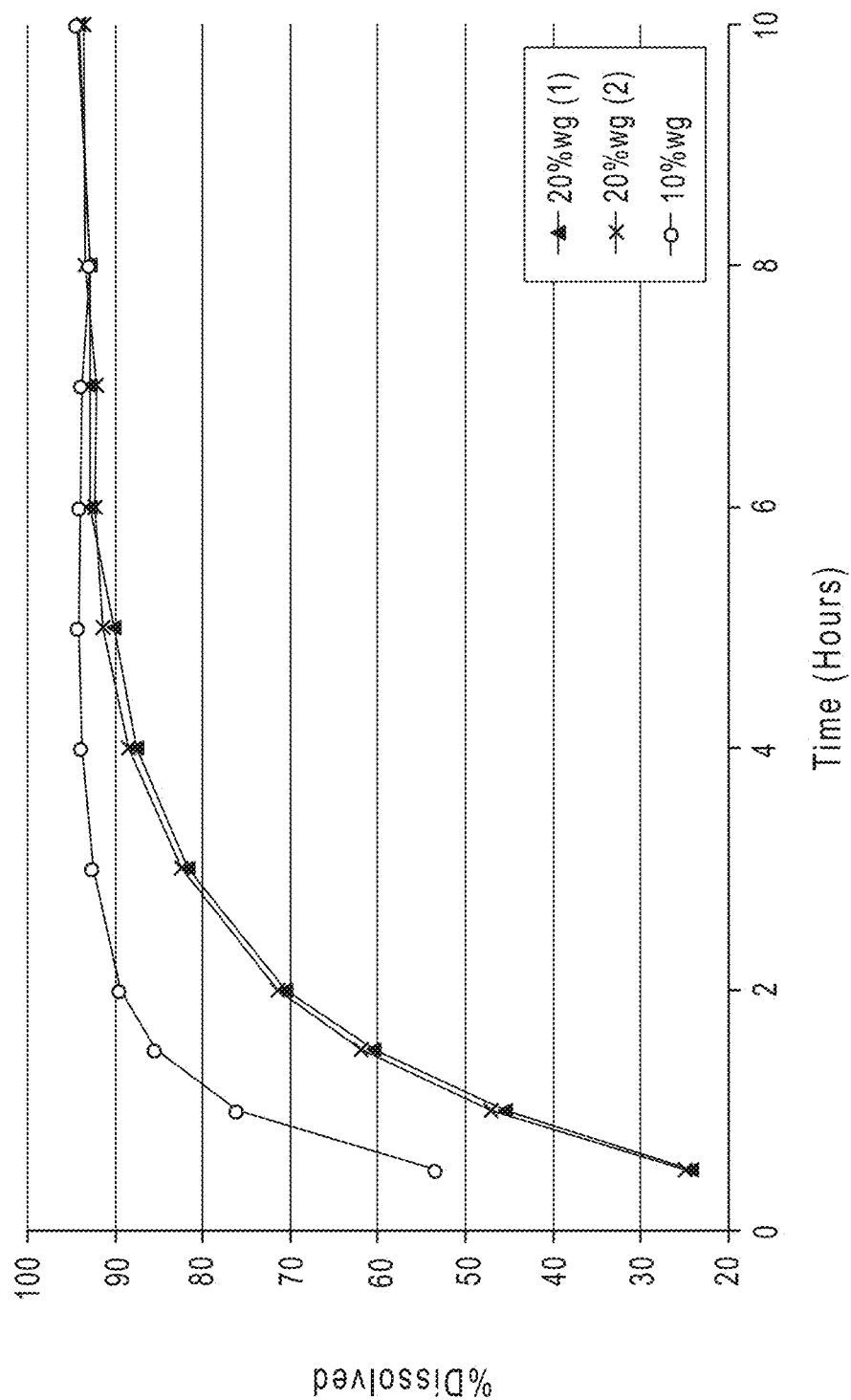
FIG. 2 shows dissolution profiles of an active pharmaceutical ingredient from granules having a coating of ethylcellulose and hydroxypropyl cellulose as described in Example 2.

The dissolution profile of the granulation was determined using a USP Type 2 dissolution apparatus in a buffered solution at pH 4.5 at a temperature of 37° C. and a paddle speed of 75 rpm. The dissolution profiles are shown in FIG. 2. The designations 20% wg (1) and 20% wg (2) refer to two separate experiments using a granulation having a 20% wg coating.

Example 4

Coated Granulation (4)

A granulation containing granules having 98.5 wt % of the compound of Formula (2a), 4-((L-valyl)oxy)butanoic acid, and characterized by a granule diameter from 200 μm to 425 μm was used.

The constituents of the functional coating formulation are provided in Table 3.

TABLE 3

Functional coating formulation.

| Component | Total (wt %) | Solids (wt %) |
|---|---|---|
| Eudragit® RS 100 ethylacrylate/methylmethacrylate copolymer | 4.4 | 62.50 |
| Eudragit® RL 100 ethylacrylate/methylmethacrylate copolymer | — | — |
| Dibutyl Sebacate | 0.4 | 6.25 |
| Talc | 2.2 | 31.25 |
| Ethanol, 95% | 93.0 | — |

The granulation was coated with the functional coating described in Table 3 using a Wurster column insert in a fluid bed. The coating conditions are provided in FIG. 21. The functional coating was applied to achieve a granulation having a 20% wg. Static build up increased during the coating process.

Figure 3:
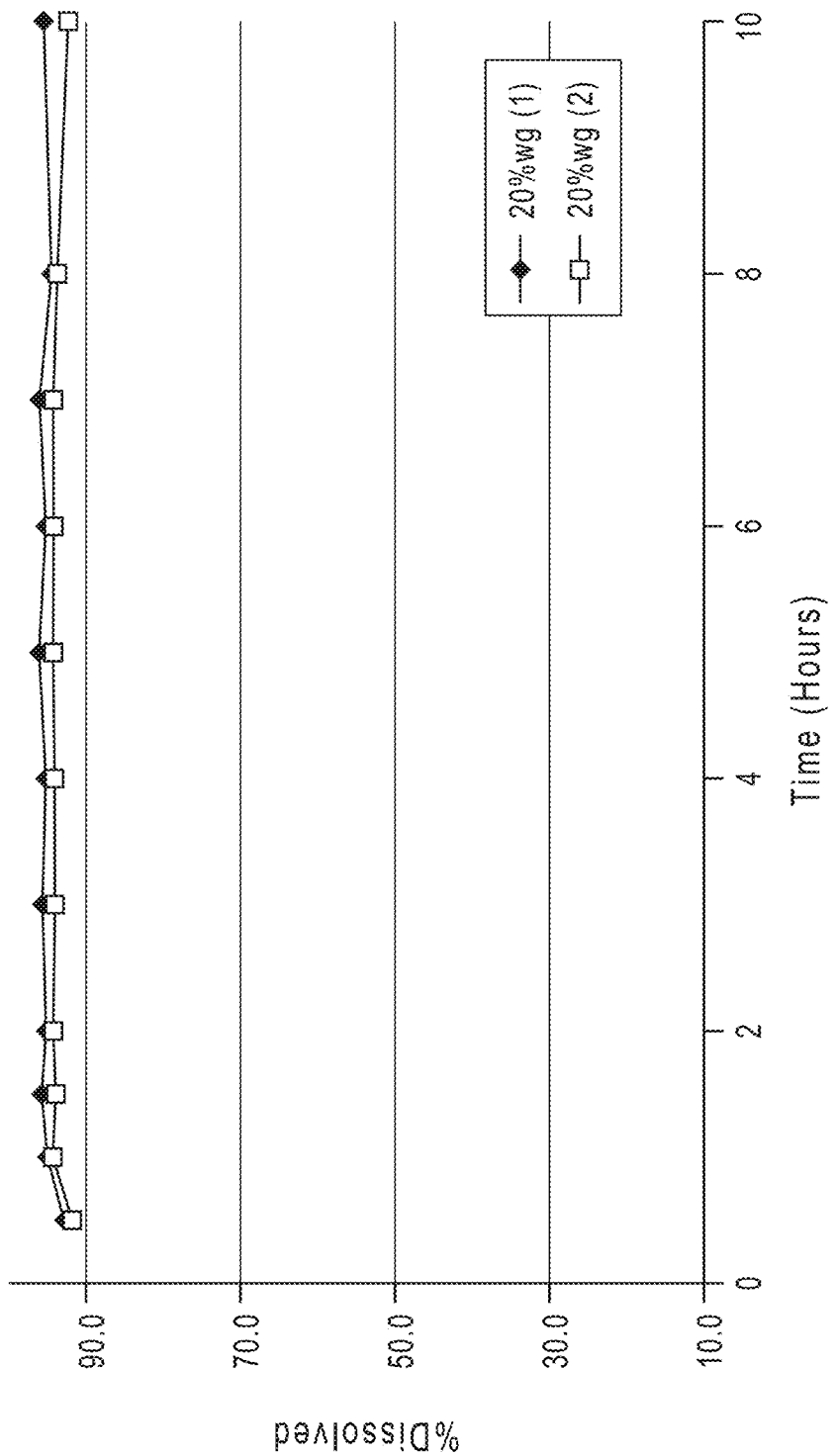
FIG. 3 shows dissolution profiles of an active pharmaceutical ingredient from granules having a coating of a methacrylic acid-methyl acrylate copolymer as described in Example 3.

The dissolution profile of the granulation was determined using a USP Type 2 dissolution apparatus in a buffered solution at pH 4.5 at a temperature of 37° C. and a paddle speed of 75 rpm. The dissolution profiles are shown in FIG. 3. The designations 30% wg (1) and 30% wg (2) refer to two separate experiments using a granulation having a 30% wg coating.

Example 5

Coated Granulation (5)

A granulation containing granules having 98.5 wt % of the compound of Formula (2a), 4-((L-valyl)oxy)butanoic acid, and characterized by a granule diameter from 200 μm to 425 μm was used.

The constituents of the functional coating formulation are provided in Table 4.

TABLE 4

Functional coating formulation.

| Component | Total (wt %) | Solids (wt %) |
|---|---|---|
| Aquaion® EC N10 ethylcellulose | 5.43 | 67.86 |
| Klucel® HPC EF Hydroxypropyl cellulose | 0.29 | 3.57 |
| Dibutyl sebacate | 0.57 | 7.14 |
| Talc | 1.71 | 21.43 |
| Water | 4.60 | — |
| Ethanol, 95% | 87.40 | — |

In this coating formulation the ratio of ethylcellulose (insoluble) to hydroxypropyl cellulose (soluble) was increased to 95:5 wt/wt to extend the release time without increasing the % wg. The talc content was also increased from 20 wt % to 30 wt % of the weight of the polymers to reduce static buildup.

The granulation was coated with the functional coating described in Table 4 using a Wurster column insert in a fluid bed. The coating conditions are provided in FIG. 21. The functional coating was applied to achieve a granulation having a 20% wg and 30% wg.

Figure 4:
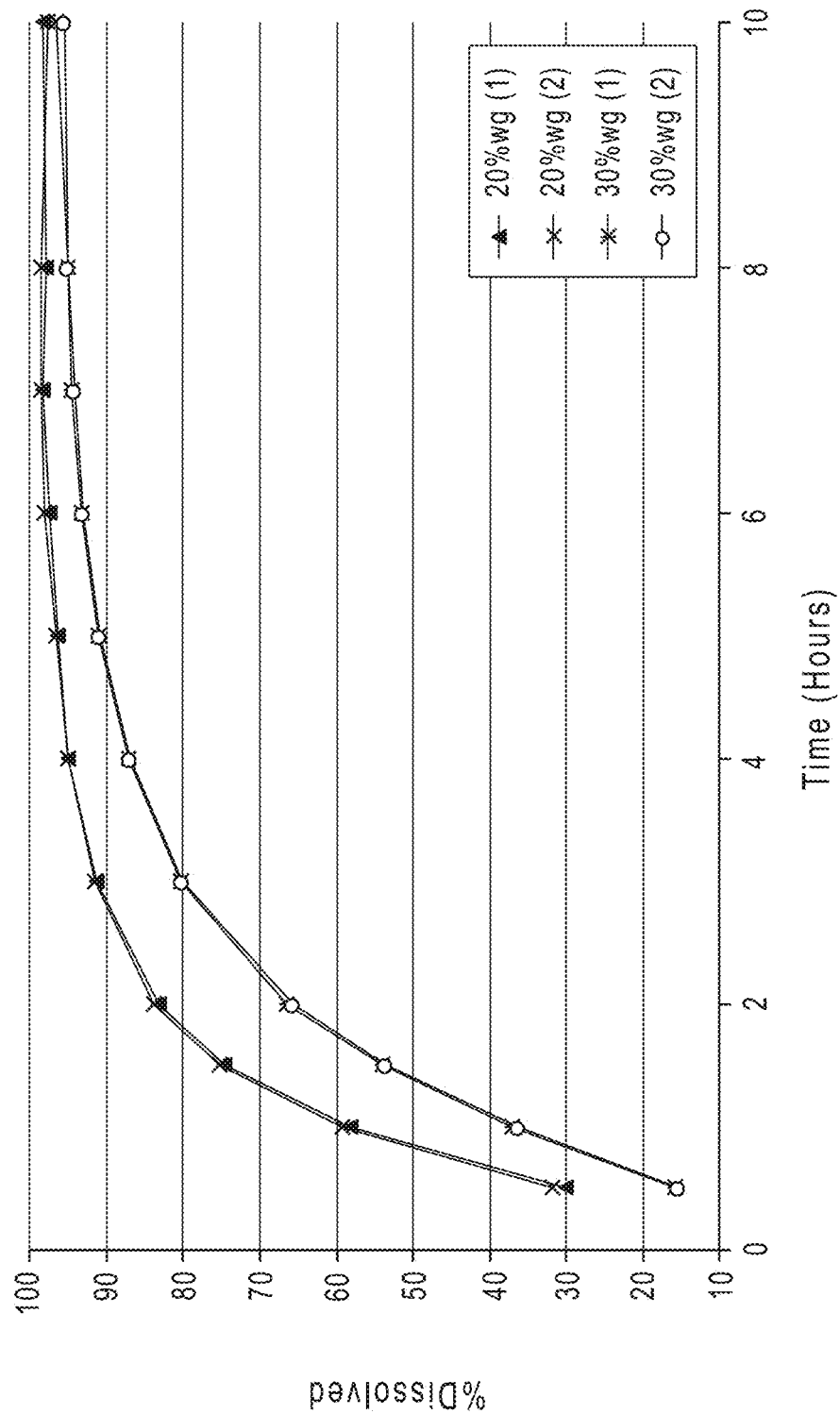
FIG. 4 shows dissolution profiles of an active pharmaceutical ingredient from granules having a coating of ethylcellulose and hydroxypropyl cellulose as described in Example 4.

The dissolution profile of the granulation was determined using a USP Type 2 dissolution apparatus in a buffered solution at pH 4.5 at a temperature of 37° C. and a paddle speed of 75 rpm. The dissolution profiles are shown in FIG. 4. The designations 30% wg (1) and 30% wg (2) refer to two separate experiments using a granulation having a 30% wg coating.

Figure 5:
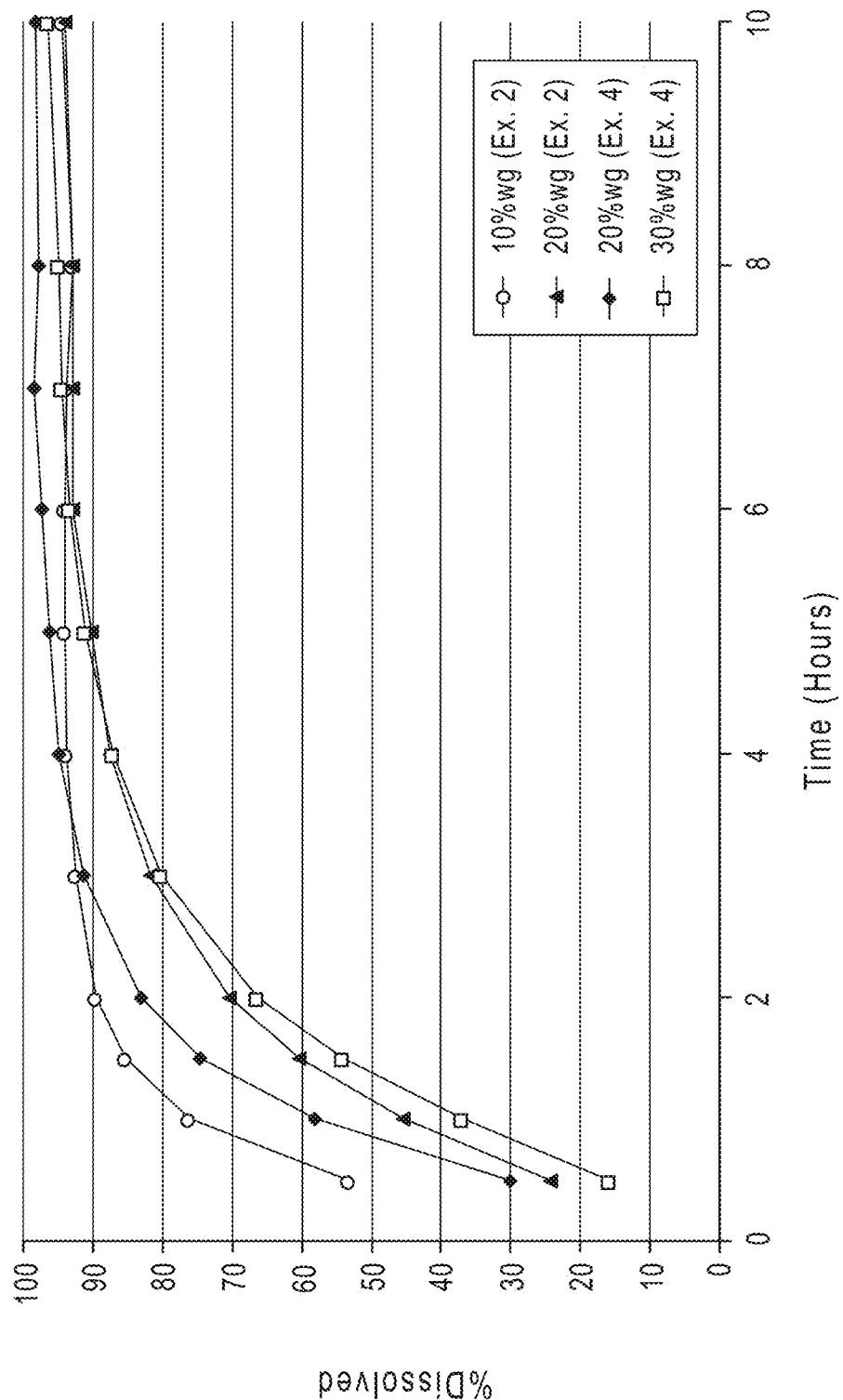
FIG. 5 shows dissolution profiles of an active pharmaceutical ingredient from granules having a coating of ethylcellulose and hydroxypropyl cellulose as described in Examples 2 and 4.

The dissolution profiles of the granulations having an ethylcellulose/hydroxypropyl cellulose (EC/HPC) functional coatings of Examples 2 and 4 are compared in FIG. 5.

Example 6

Coated Granulation (6)

A granulation containing granules having 98.5 wt % of the compound of Formula (2a), 4-((L-valyl)oxy)butanoic acid, and characterized by a granule diameter from 200 μm to 425 μm was used.

The constituents of the functional coating formulation are provided in Table 5.

TABLE 5

Functional coating formulation.

| Component | Total (wt %) | Solids (wt %) |
|---|---|---|
| Aquaion® EC N10 ethylcellulose | 5.85 | 73.08 |
| Klucel® HPC EF Hydroxypropyl cellulose | 0.31 | 3.85 |

TABLE 5-continued

| Functional coating formulation. | | |
|---|---|---|
| Component | Total (wt %) | Solids (wt %) |
| Dibutyl sebacate | 0.62 | 7.69 |
| Talc | 1.23 | 15.38 |
| Water | 6.78 | — |
| Ethanol, 95% | 85.22 | — |

In this coating formulation the talc content was set to 20% that of the polymers and the water content was increased to 12 wt % of the solvent.

The granulation was coated with the functional coating described in Table 5 using a Wurster column insert in a fluid bed. The coating conditions are provided in FIG. 21. The functional coating was applied to achieve a granulation having a 20% wg, 25% wg, and 35% wg. Significant agglomeration was evident.

Figure 6:
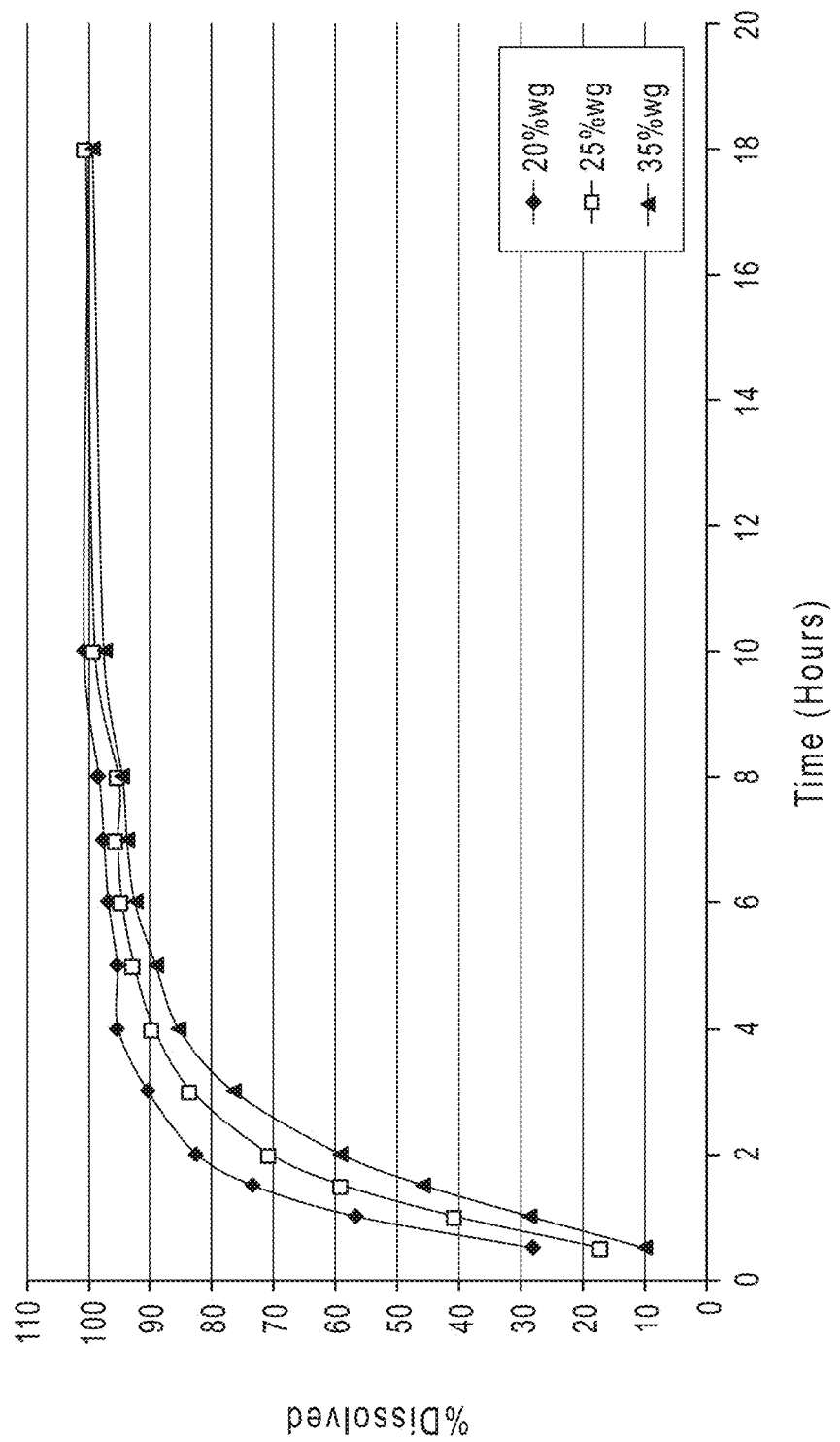
FIG. 6 shows dissolution profiles of an active pharmaceutical ingredient from granules having a coating of ethylcellulose and hydroxypropyl cellulose as described in Example 5.

The dissolution profile of the granulation was determined using a USP Type 2 dissolution apparatus in a buffered solution at pH 4.5 at a temperature of 37° C. and a paddle speed of 75 rpm. The dissolution profiles are shown in FIG. 6.

Example 7

Coated Granulation (7)

A granulation containing granules having 98.5 wt % of the compound of Formula (2a), 4-((L-valyl)oxy)butanoic acid, and characterized by a granule diameter from 200 μm to 425 μm was used.

The constituents of the functional coating formulation are provided in Table 6.

TABLE 6

| Functional coating formulation. | | |
|---|---|---|
| Component | Total (wt %) | Solids (wt %) |
| Aquaion® EC N10 ethylcellulose | 5.85 | 73.08 |
| Klucel® HPC EF Hydroxypropyl cellulose | 0.31 | 3.85 |
| Dibutyl sebacate | 0.62 | 7.69 |
| Talc | 1.23 | 15.38 |
| Water | 4.84 | — |
| Ethanol, 95% | 87.16 | — |

In this coating formulation the talc content was set to 20% that of the polymers and the water content was 10 wt % of the solvent.

Figure 7A:
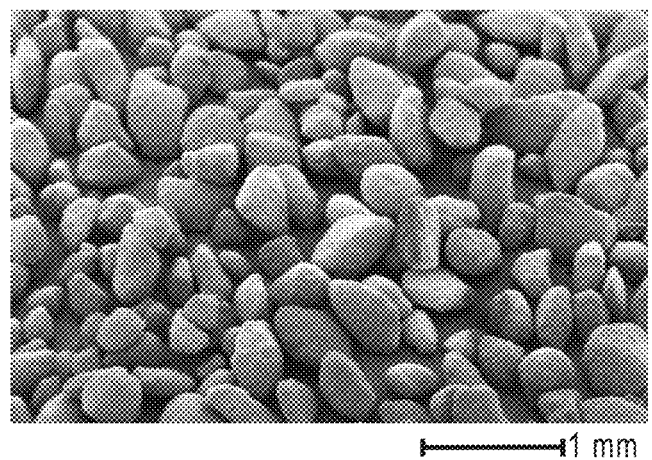
FIGS. 7A-7C show SEM images of granules coated with 35% wg of an ethylcellulose/hydroxypropyl cellulose coating at three different magnifications as described in Example 6.
Figure 7B:
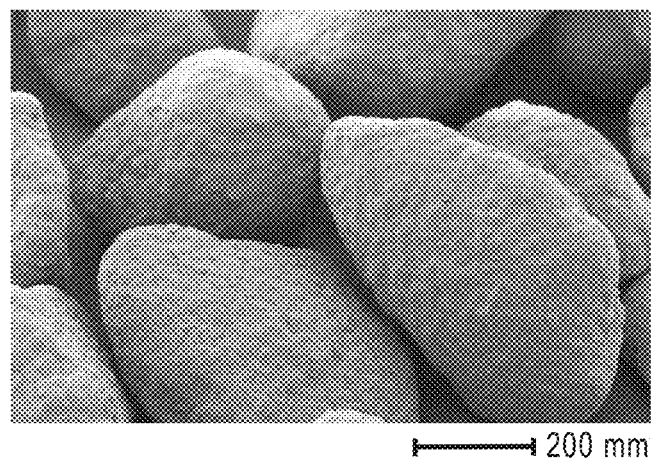
Figure 7C:
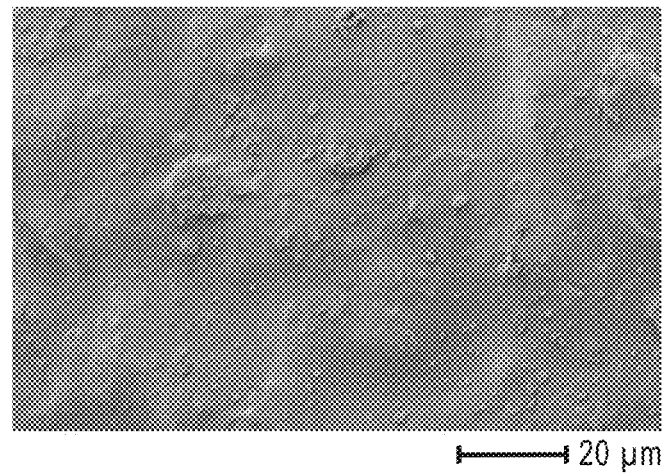

The granulation was coated with the functional coating described in Table 6 using a Wurster column insert in a fluid bed. The coating conditions are provided in FIG. 21. The spray rate was reduced to avoid over-wetting and the ambient air was humidified. The functional coating was applied to achieve a granulation having a 20% wg, 30% wg, and 35% wg. There was minimal agglomeration. SEM images of the granulation having a 35% wg functional coating are shown in FIGS. 7A-7C at magnifications of 27×, 110×, and 1000×, respectively.

The water content of the uncoated granulation was 1.24 wt % and for the coated granulation was 0.23 wt %.

Figure 8:
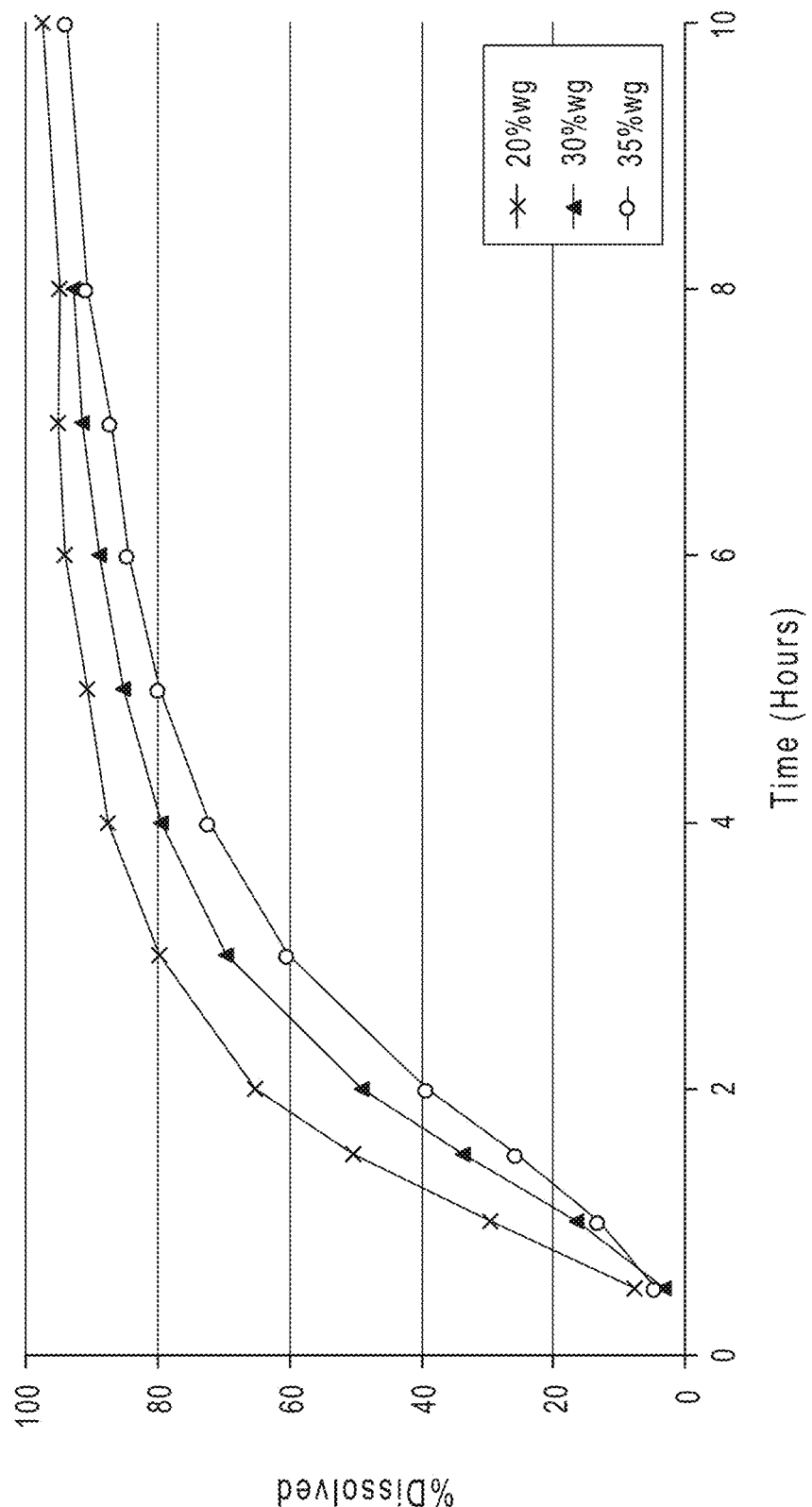
FIG. 8 shows dissolution profiles of an active pharmaceutical ingredient from granules having an ethylcellulose/hydroxypropyl cellulose coating representing different % wg as described in Example 6.

The dissolution profile of the granulation was determined using a USP Type 2 dissolution apparatus in a buffered solution at pH 4.5 at a temperature of 37° C. and a paddle speed of 75 rpm. The dissolution profiles are shown in FIG. 8.

Example 8

Coated Granulation (8)

A granulation containing granules having 98.5 wt % of the compound of Formula (2a), 4-((L-valyl)oxy)butanoic acid, and characterized by a granule diameter from 200 μm to 425 μm was used.

In this coating formulation and processing conditions were similar to that of Example 6 except that the batch size was increased from 425 g to 500 g.

The constituents of the functional coating formulation are provided in Table 7.

TABLE 7

| Functional coating formulation. | | |
|---|---|---|
| Component | Total (wt %) | Solids (wt %) |
| Aquaion® EC N10 ethylcellulose | 5.85 | 73.08 |
| Klucel® HPC EF Hydroxypropyl cellulose | 0.31 | 3.85 |
| Dibutyl Sebacate | 0.62 | 7.69 |
| Talc | 1.23 | 15.38 |
| Water | 4.84 | — |
| Ethanol, 95% | 87.16 | — |

Figure 9A:
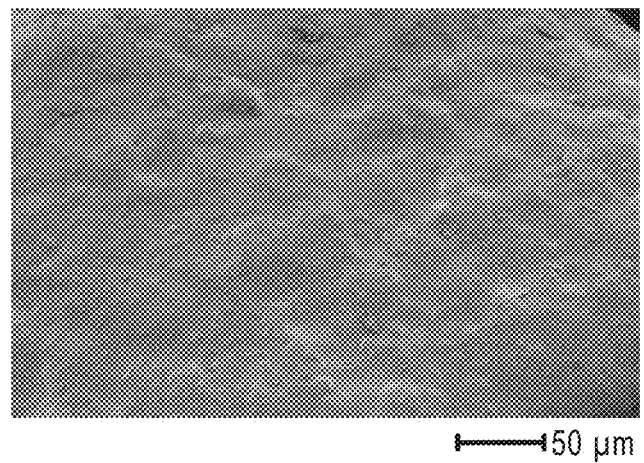
FIGS. 9A-9C show SEM images of granules coated with 35% wg of an ethylcellulose/hydroxypropyl cellulose coating at three different magnifications as described in Example 7.
Figure 9B:
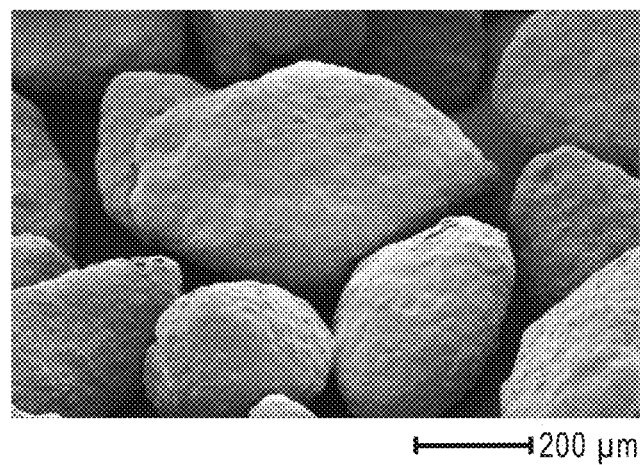
Figure 9C:
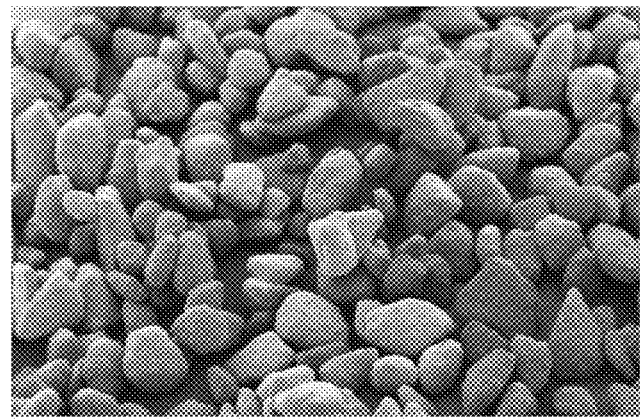

The granulation was coated with the functional coating described in Table 7 using a Wurster column insert in a fluid bed. The coating conditions are provided in FIG. 21. The functional coating was applied to achieve a granulation having a 20% wg, 30% wg, and 35% wg. There was minimal agglomeration. SEM images of the granulation having a 35% wg functional coating are shown in FIGS. 9A-9C at magnifications of 27×, 110×, and 340×, respectively.

The water content of the undried uncoated granulation was 2.42 wt %, of the dried uncoated granulation was 0.21 wt %, and for the 35% wg coated granulation was 0.25 wt %.

Figure 10:
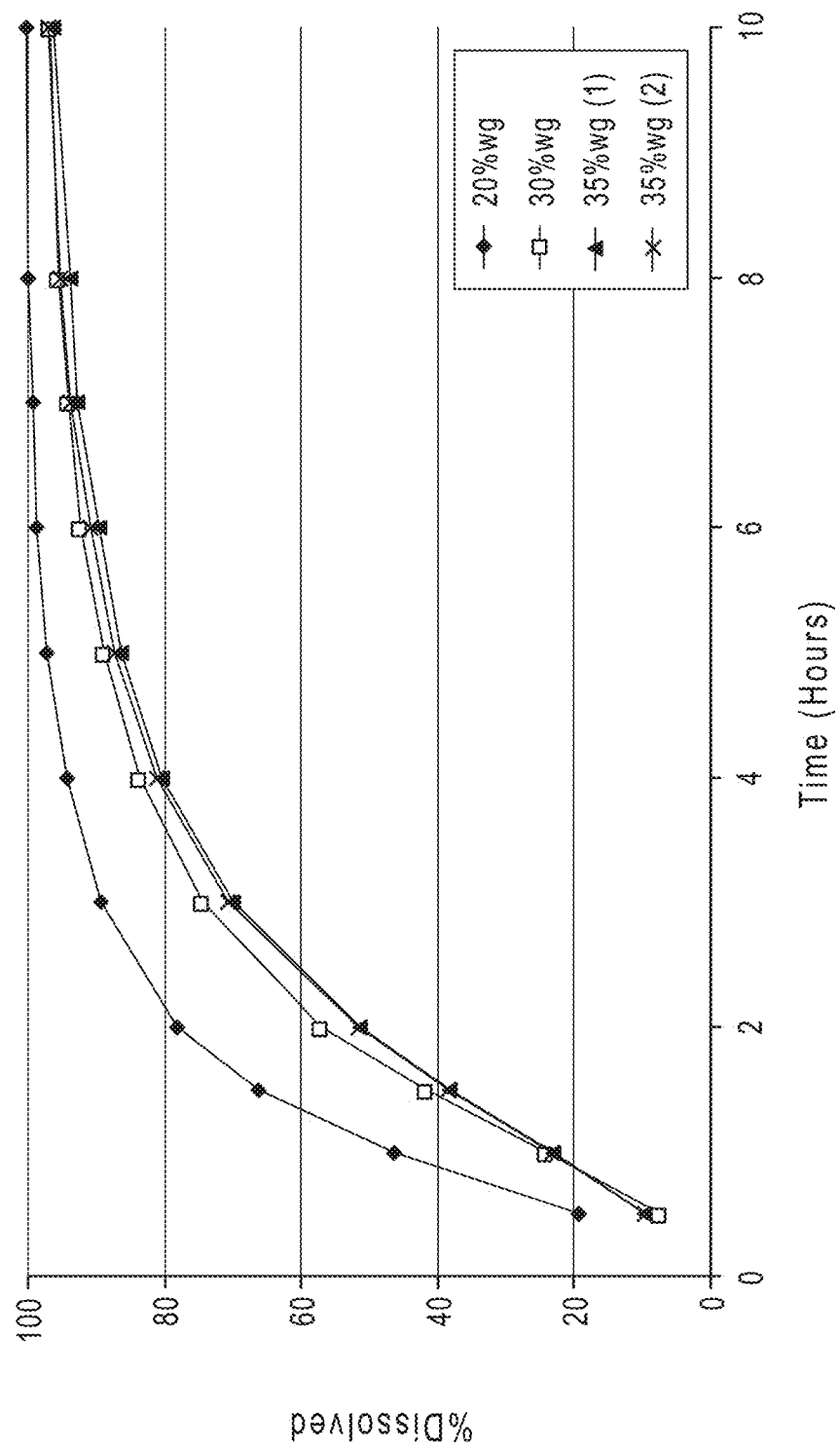
FIG. 10 shows dissolution profiles of an active pharmaceutical ingredient from granules having an ethylcellulose/hydroxypropyl cellulose coating representing different % wg as described in Example 7.

The dissolution profile of the granulation was determined using a USP Type 2 dissolution apparatus in a buffered solution at pH 4.5 at a temperature of 37° C. and a paddle speed of 75 rpm. The dissolution profiles are shown in FIG. 10.

The particle size distribution of the granulation having a 35% wg coating is shown in FIG. 11.

Example 9

Coated Granulation (9)

A granulation containing granules having 98.5 wt % of the compound of Formula (2a), 4-((L-valyl)oxy)butanoic acid, and characterized by a granule diameter from 200 μm to 425 μm was used.

In this example the granulation was first coated with a hydroxypropyl cellulose seal coat before applying the functional coating. The seal coat was applied to a 5% wg and the constituents of the seal coat formulation are provided in Table 8.

TABLE 8

Seal coat formulation.

| Component | Total (wt %) | Solids (wt %) |
|---|---|---|
| Klucel® HPC EF Hydroxypropyl cellulose | 6.00 | 100 |
| Water | 4.95 | — |
| Ethanol, 95% | 89.05 | — |

The processing condition for applying the seal coat are provided in FIG. 21 (9A).

The constituents of the functional coating formulation are provided in Table 9.

TABLE 9

Functional coating formulation.

| Component | Total (wt %) | Solids (wt %) |
|---|---|---|
| Aquaion® EC N10 ethylcellulose | 5.85 | 73.08 |
| Klucel® HPC EF Hydroxypropyl cellulose | 0.31 | 3.85 |
| Dibutyl Sebacate | 0.62 | 7.69 |
| Talc | 1.23 | 15.38 |
| Water | 4.84 | — |
| Ethanol, 95% | 87.16 | — |

Figure 12A:
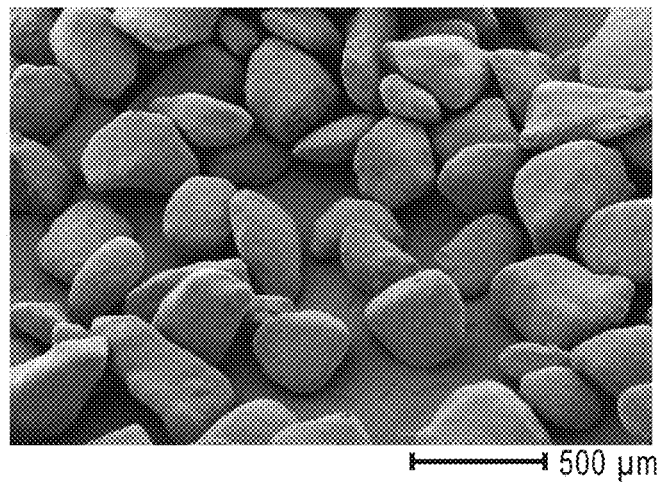
FIGS. 12A-12C show SEM images of granules coated with a 6% wg ethylcellulose/hydroxypropyl cellulose seal coating at three different magnifications as described in Example 8.
Figure 12B:
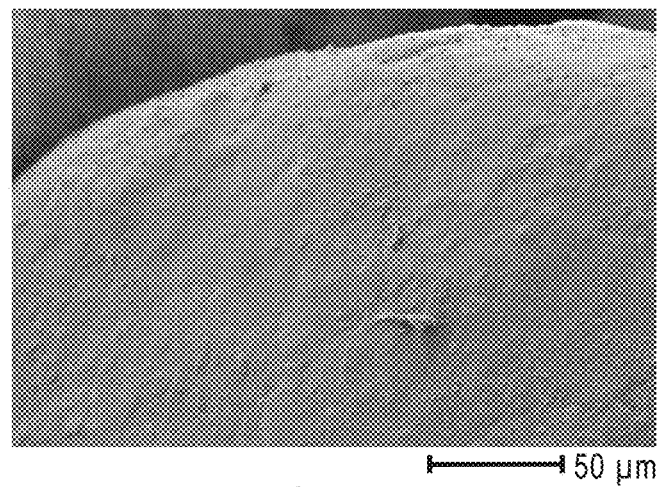
Figure 12C:
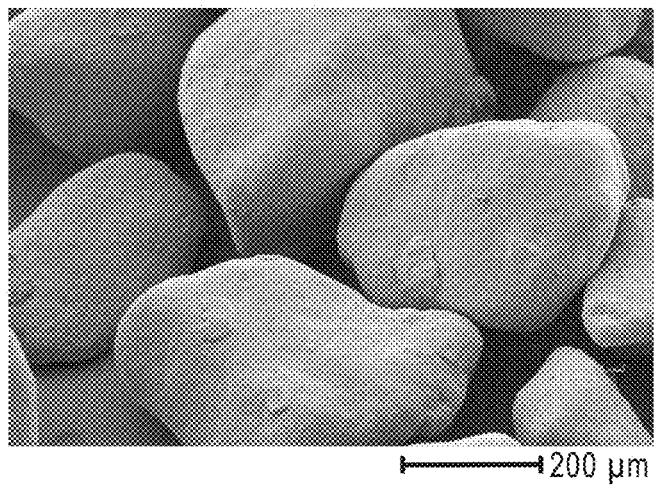
Figure 13A:
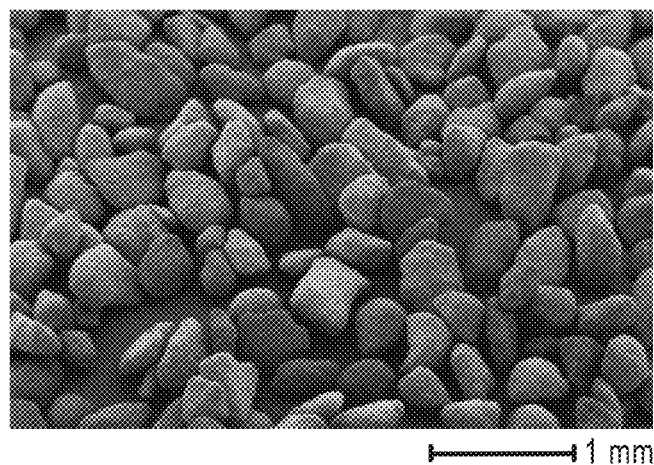
FIGS. 13A-13C show SEM images of granules coated with 35% wg of an ethylcellulose/hydroxypropyl cellulose coating at three different magnifications as described in Example 9.
Figure 13B:
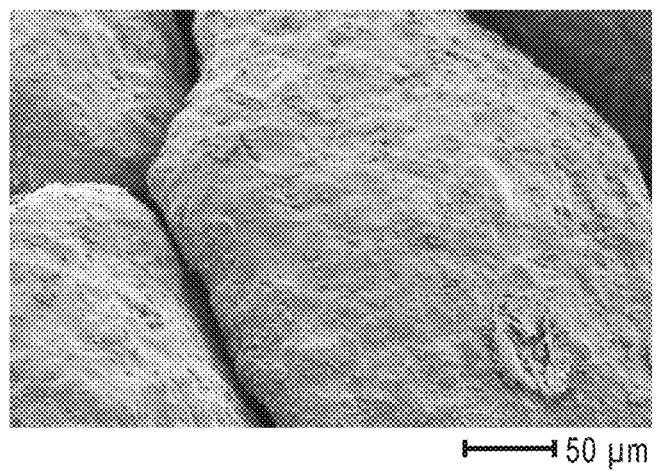
Figure 13C:
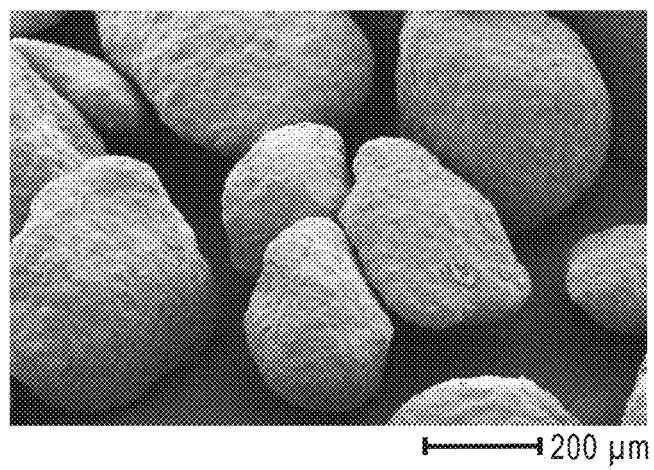

The granulation was coated with the functional coating described in Table 9 using a Wurster column insert in a fluid bed. The functional coating application conditions are provided in FIG. 21 (9B). The functional coating was applied to achieve a granulation having a 20% wg, 30% wg, and 35% wg. There was minimal agglomeration. SEM images of the granulation having a 30% wg functional coating are shown in FIGS. 12A-12C at magnifications of 50×, 130×, and 500×, respectively. SEM images of the granulation having a 35% wg functional coating are shown in FIGS. 13A-13C at magnifications of 27×, 110×, and 340×, respectively.

Figure 14:
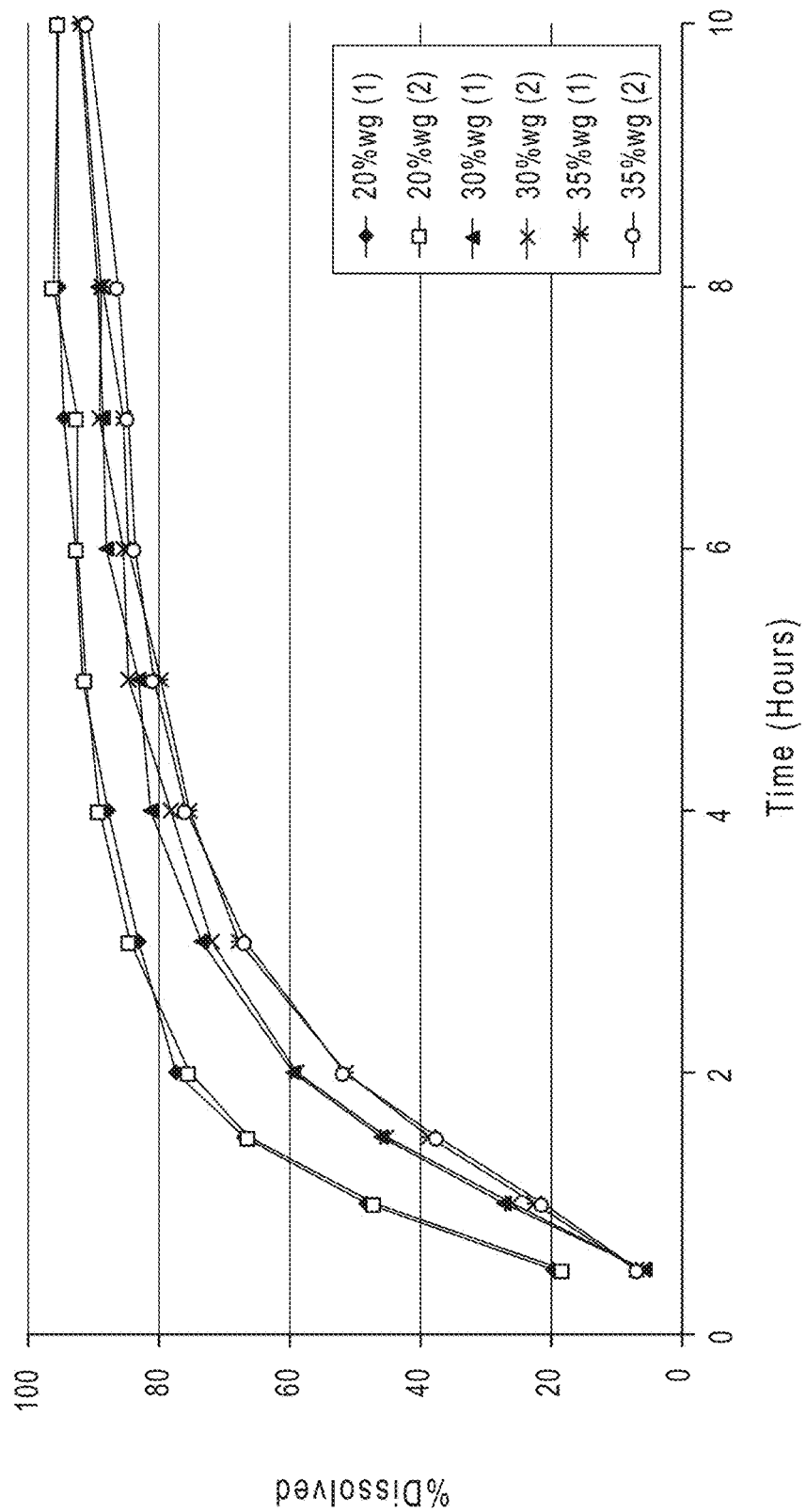
FIG. 14 shows dissolution profiles of an active pharmaceutical ingredient from granules having an ethylcellulose/hydroxypropyl cellulose coating representing different % wg as described in Example 9.

The dissolution profile of the granulations was determined using a USP Type 2 dissolution apparatus in a buffered solution at pH 4.5 at a temperature of 37° C. and a paddle speed of 75 rpm. The dissolution profiles are shown in FIG. 14.

The particle size distribution of the granulations having a 35% wg coating of Examples 7, 8, and 9 is compared in FIG. 15.

Figure 16:
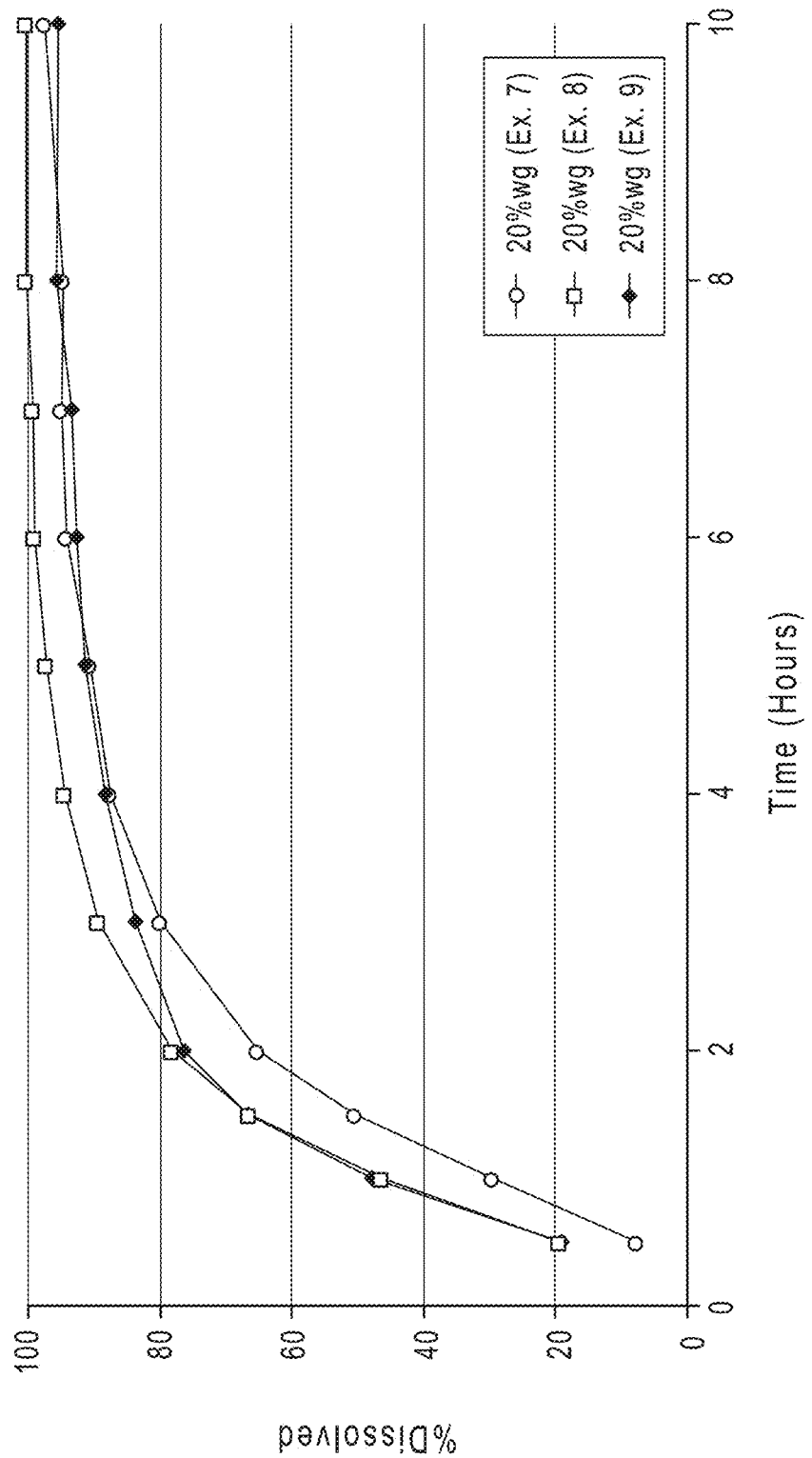
FIG. 16 shows dissolution profiles of an active pharmaceutical ingredient from granules having a 20% wg ethylcellulose/hydroxypropyl cellulose coating as described in Examples 7, 8, and 9.
Figure 17:
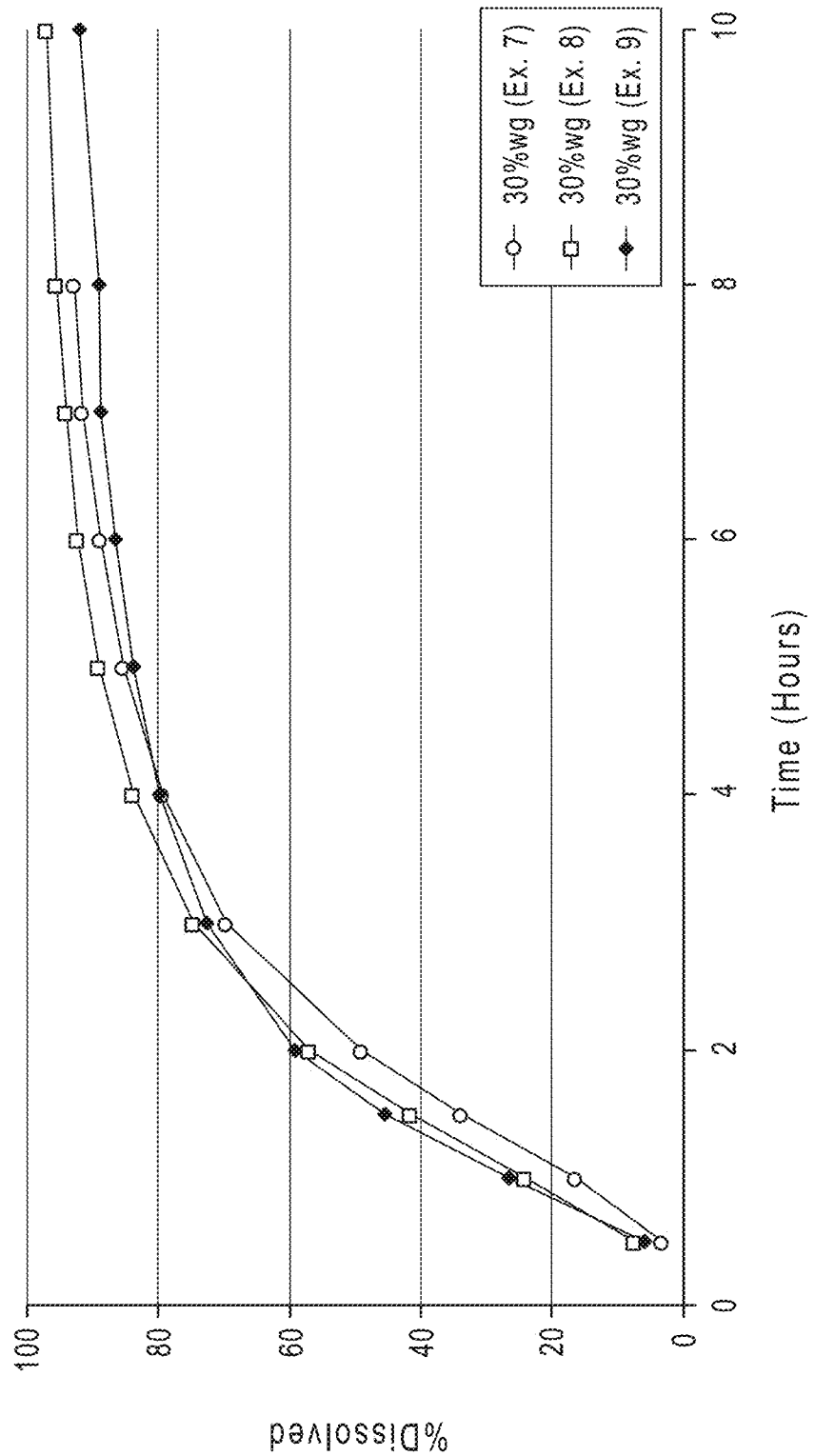
FIG. 17 shows dissolution profiles of an active pharmaceutical ingredient from granules having a 30% wg ethylcellulose/hydroxypropyl cellulose coating as described in Examples 7, 8, and 9.

The dissolution profiles for the granulations having 20% wg, 30% wg, and 35% wg functional coatings of Examples 7, 8, and 9 are compared in FIGS. 16-18, respectively.

Example 10

Coated Granulation (10)

A granulation containing granules having 90.0 wt % of the compound of Formula (2a), 4-((L-valyl)oxy)butanoic acid, and characterized by a particle size from 225 μm to 400 μm was used. The uncoated granulation comprising 4-((L-valyl)oxy)butanoic acid was prepared using MicroPX® micropelletizing technology (Glatt GmbH).

TABLE 10

Seal coat formulation.

| Component | Total (wt %) | Solids (wt %) |
|---|---|---|
| Klucel® HPC EF Hydroxypropyl cellulose | 6.00 | 100 |
| Water | 4.95 | — |
| Ethanol, 95% | 89.05 | — |

The constituents of the functional coating formulation are provided in Table 11.

TABLE 11

Functional coating formulation.

| Component | Total (wt %) | Solids (wt %) |
|---|---|---|
| Aquaion® EC N10 ethylcellulose | 5.84 | 73.00 |
| Klucel® HPC EF Hydroxypropyl cellulose | 0.31 | 3.88 |
| Dibutyl Sebacate | 0.62 | 7.75 |
| Talc Pharma 400 | 1.23 | 15.38 |
| Treated Water | 9.20 | — |
| Ethanol, ≥95.5% 200 proof, anhydrous | 82.20 | — |

The granulation was coated with the functional coating described in Table 11 using a Wurster column insert in a fluid bed. The functional coating application conditions are provided in Table 12

TABLE 12

Coating application conditions.

| Parameter | Time (min) | Susp. Sprayed (g) | Weight Gain (%) | Spray Rate (g/min) | In. Temp (° C.) | Ex. Temp (° C.) | Process Air (cpm) | Atom Air (psi) | Att. (psi) Air | Room Dew Point (° C.) |
|---|---|---|---|---|---|---|---|---|---|---|
| Target | | 8500 | 20 | 15 | | 33-34 | 75-95 | 65 | 20-25 | 10-13 |
| Range | | 8480-8520 | | 10-35 | | 30-35 | 60-110 | 60-70 | 15-25 | 7-16 |
| Coating Run SB1 | 241 | 3751 | 20 | 16 | 40.2 | 32.6 | 85 | 64.2 | 20 | 12.4 |
| Coating Run SB2 | 340 | 3753 | 20 | 16 | 40.1 | 32.7 | 85 | 64.5 | 20 | 12.4 |

The functional coating was applied to achieve a coated granulation having a 20% wg, 25% wg, and 30% wg functional coating.

Coated granulations having a 20% wg functional coating had a bulk density of 0.629 g/mL. The particle size distribution as provided in Table 13.

TABLE 13

| Particle Size distribution. | | | | | | | |
|---|---|---|---|---|---|---|---|
| Particle Size (μm) | <210 | 210 | 300 | 425 | 600 | 840 | 1190 |
| % of Coated Granulation | 0. | 12.8 | 72.0 | 11.9 | 3.0 | 0.4 | 0 |

In the coated pharmaceutical granulation 12.9% of the coated granules can have a particle size less than 300 μm, 83.8% of the coated granules can have a particle size from 300 μm to 600 μm, and 3.3% of the coated granules can have a particle size from 600 μm to 1190 μm.

Figure 22:
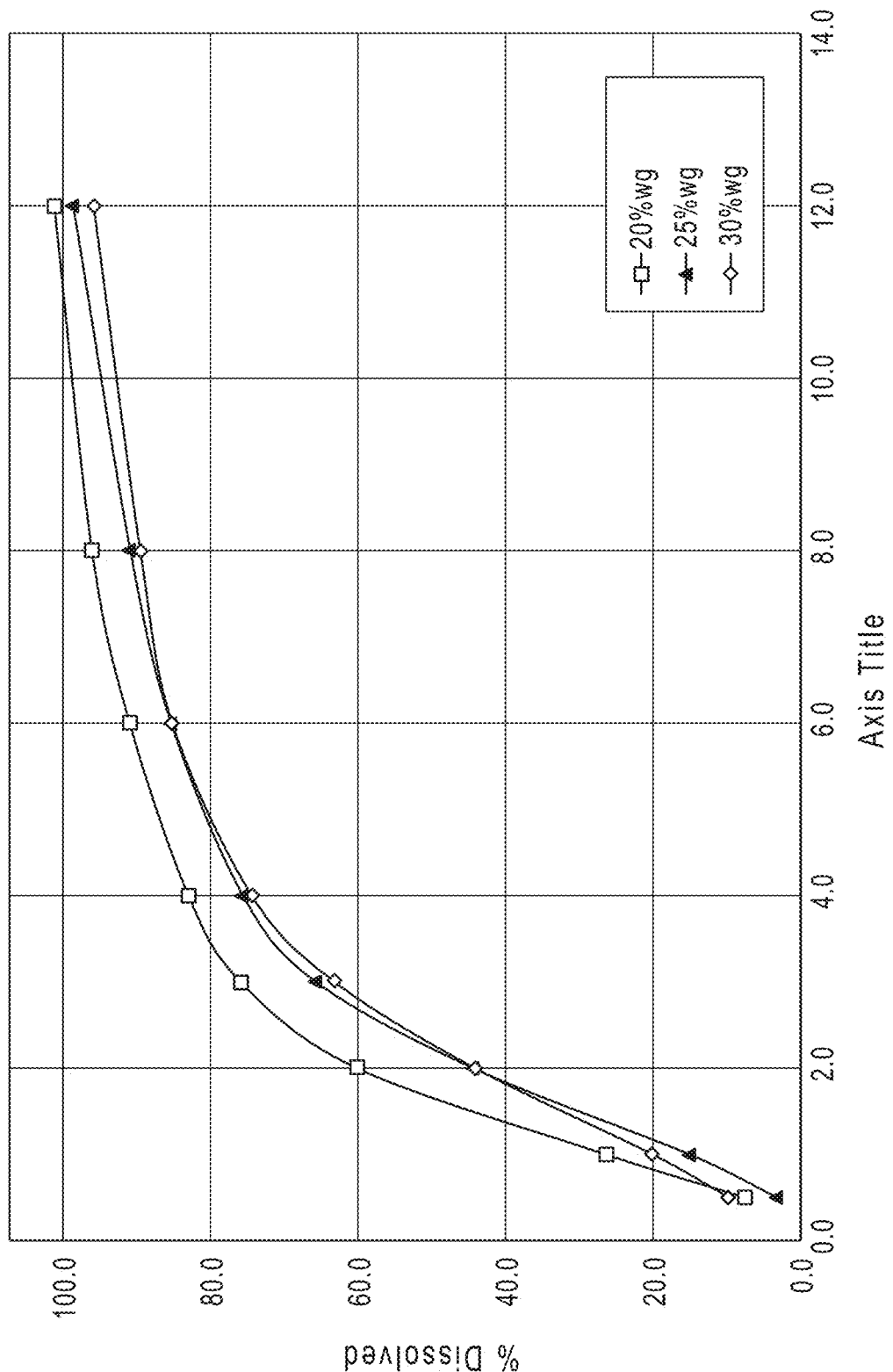
FIG. 22 shows dissolution profiles of an active pharmaceutical ingredient from granules having different % wg of an ethylcellulose/hydroxypropyl cellulose coating as described in Example 10.

The dissolution profile of the granulations was determined using a USP Type 2 dissolution apparatus in a buffered solution at pH 4.5 at a temperature of 37° C. and a paddle speed of 75 rpm. The dissolution profiles are shown in FIG. 22.

Example 11

Water-Based Seal Coated Granulation of 4-((L-Valyl)oxy)butanoic Acid

A seal-coated granulation was prepared by spray coating an uncoated granulation of 4-((L-valyl)oxy)butanoic acid granules.

The uncoated granulation comprising 4-((L-valyl)oxy) butanoic acid was prepared using MicroPX® micro-pelletizing technology (Glatt GmbH). The uncoated granulation had an average granule size (D50) from 225 μm to 275 μm.

The composition used to provide the seal coat contained 14.2 wt % hydroxypropylmethyl cellulose (Pharmacoat® 603), 2.1 wt % talc and 85.6 wt % water, where wt % is based on the total weight of the seal coat composition.

The composition was sprayed-coated onto the uncoated granulation to provide a seal coating having a thickness of 2.23 (+/−0.34) μm.

Example 12

Acetone-Based Seal Coated Granulation of 4-((L-Valyl)oxy)butanoic Acid

A seal-coated granulation was prepared by spray coating an uncoated granulation of 4-((L-valyl)oxy)butanoic acid granules.

The uncoated granulation comprising 4-((L-valyl)oxy) butanoic acid was prepared using MicroPX® micro-pelletizing technology (Glatt GmbH). The uncoated granulation had an average granule diameter (D50) from 225 μm to 275 μm.

The composition used to provide the seal coat contained 5.4 wt % hydroxypropyl cellulose (Klucel® EF), 2.1 wt % talc and 92.5 wt % acetone, where wt % is based on the total weight of the seal coat composition.

The composition was sprayed-coated onto the uncoated granulation to provide a seal coating having a thickness of 1.30 (+/−0.27) μm.

It should be noted that there are alternative ways of implementing the embodiments disclosed herein. Accordingly, the present embodiments are to be considered as illustrative and not restrictive. Furthermore, the claims are not to be limited to the details given herein and are entitled their full scope and equivalents thereof.

What is claimed is:

1. A pharmaceutical granulation for once a day dosing comprising a plurality of coated granules, wherein:
   the coated granules comprise a core and a controlled release coating surrounding the core;
   the core comprises from 90.0 wt % to 99.5 wt % of a compound of Formula (2):

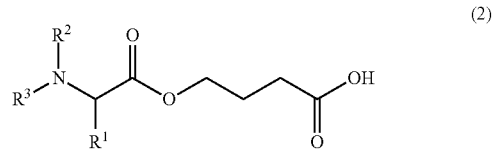

or a pharmaceutically acceptable salt thereof, wherein,
   $R^1$ is selected from hydrogen and $C_{1-6}$ alkyl; and
   each of $R^2$ and $R^3$ is independently selected from hydrogen, $C_{1-6}$ alkyl, $C_{1-6}$ alkoxycarbonyl, and $C_{3-6}$ cycloalkoxycarbonyl;
   wherein wt % is based on the total weight of the core;
   the coated granules are characterized by a particle size distribution (PSD) (D50) from 150 μm to 500 μm, wherein the particle size distribution is determined by laser diffraction;
   the coated granules comprise from 50 wt % to 95 wt % of the compound of Formula (2), wherein wt% is based on the total weight of the coated granules;
   the controlled release coating comprises:
      from 60 wt % to 85 wt % of a matrix polymer, wherein the matrix polymer comprises:
         from 92 wt % to 98 wt % of a water-insoluble polymer; and
         from 2 wt % to 8 wt % of a water-soluble polymer, wherein wt % is based on the total weight of the matrix polymer;
      from 10 wt % to 20 wt % of talc; and
      from 3 wt % to 13 wt % of dibutyl sebacate,
      wherein wt % is based on the total weight of the controlled release coating; and
   the controlled release coating has a thickness from 5 μm to 40 μm.

2. The pharmaceutical granulation of claim 1, wherein the water-insoluble polymer comprises ethylcellulose.

3. The pharmaceutical granulation of claim 1, wherein the water soluble polymer comprises hydroxypropyl cellulose.

4. The pharmaceutical granulation of claim 1, wherein the coated granules comprise:
   from 55 wt % to 90 wt % of the core; and
   from 10 wt % to 45 wt % of the controlled release coating, wherein wt % is based on the total weight of the coated granules.

5. The pharmaceutical granulation of claim 1, wherein the controlled release coating has a thickness from 5 μm to 30 μm.

6. The pharmaceutical granulation of claim 1, wherein the compound of Formula (2) has an aqueous solubility greater than 100 mg/mL.

7. The pharmaceutical granulation of claim 1, wherein the compound of Formula (2) is selected from:
   4-(((tert-butoxycarbonyl)glycyl)oxy)butanoic acid;
   4-(glycyloxy)butanoic acid;
   4-((D-valyl)oxy)butanoic acid;
   4-((L-alanyl)oxy)butanoic acid;
   4-(((ethoxycarbonyl)glycyl)oxy)butanoic acid;
   4-(((isopropoxycarbonyl)glycyl)oxy)butanoic acid;

4-((((cyclohexyloxy)carbonyl)glycyl)oxy)butanoic acid;
4-(((ethoxycarbonyl)-D-valyl)oxy)butanoic acid;
4-((L-valyl)oxy)butanoic acid;
a pharmaceutically acceptable salt of any of the foregoing; and
a combination of any of the foregoing.

8. The pharmaceutical granulation of claim 1, wherein the compound of Formula (2) comprises 4-((L-valyl)oxy)butanoic acid (2a) or a pharmaceutically acceptable salt thereof:

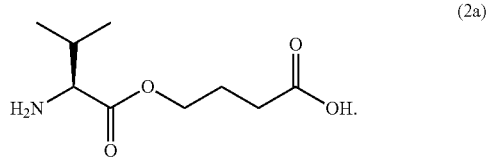

(2a)

9. A pharmaceutical composition comprising the pharmaceutical granulation of claim 1.

10. The pharmaceutical composition of claim 9, wherein the pharmaceutical composition comprises from 500 mg equivalents to 12 g equivalents of γ-hydroxybutyric acid.

11. The pharmaceutical composition of claim 9, wherein the compound of Formula (2) comprises 4-((L-valyl)oxy)butanoic acid (2a) or a pharmaceutically acceptable salt thereof:

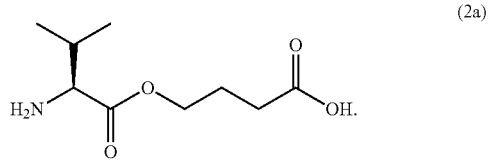

(2a)

12. The pharmaceutical composition of claim 9, wherein the pharmaceutical composition comprises a therapeutically effective amount of the compound of Formula (2) for treating excessive daytime sleepiness associated with narcolepsy, excessive daytime sleepiness associated with Parkinson's disease, excessive daytime sleepiness associated with multiple sclerosis, cataplexy associated with narcolepsy, fatigue in a patient with Parkinson's disease, fatigue in a patient with multiple sclerosis, or fibromyalgia.

13. A method of providing a therapeutically effective amount of γ-hydroxybutyric acid in the systemic circulation of a patent for treating a disease comprising administering to a patient in need of such treatment a therapeutically effective amount of the pharmaceutical composition of claim 9 for treating the disease, wherein the disease is selected from excessive daytime sleepiness associated with narcolepsy, excessive daytime sleepiness associated with Parkinson's disease, excessive daytime sleepiness associated with multiple sclerosis, cataplexy associated with narcolepsy, fatigue in a patient with Parkinson's disease, fatigue in a patient with multiple sclerosis, and fibromyalgia.

14. The pharmaceutical granulation of claim 1, wherein,
the water-soluble polymer comprises ethylcellulose; and
the water-insoluble polymer comprises hydroxypropylcellulose.

15. The pharmaceutical granulation of claim 1, wherein the core is characterized by:
an average sphericity greater than 0.90, wherein sphericity is determined using wet dispersion particle shape methods or by dynamic image analysis; and
a friability value less than 2 wt %, wherein friability is determined using a sonic sifter.

16. The pharmaceutical composition of claim 9, wherein the pharmaceutical composition comprises an oral suspension.

* * * * *